US008652836B2

(12) United States Patent
Hu

(10) Patent No.: US 8,652,836 B2
(45) Date of Patent: Feb. 18, 2014

(54) DEFECTIVE RIBOSOMAL PRODUCTS IN BLEBS (DRIBBLES) AND METHODS OF USE TO STIMULATE AN IMMUNE RESPONSE

(75) Inventor: Hong-Ming Hu, Portland, OR (US)

(73) Assignee: Providence Health System, Portland, OR (US)

( * ) Notice: Subject to any disclaimer, the term of this patent is extended or adjusted under 35 U.S.C. 154(b) by 413 days.

(21) Appl. No.: 11/997,294

(22) PCT Filed: Jul. 27, 2006

(86) PCT No.: PCT/US2006/029404
§ 371 (c)(1),
(2), (4) Date: Jan. 29, 2008

(87) PCT Pub. No.: WO2007/016340
PCT Pub. Date: Feb. 8, 2007

(65) Prior Publication Data
US 2009/0220530 A1    Sep. 3, 2009

Related U.S. Application Data

(60) Provisional application No. 60/703,675, filed on Jul. 29, 2005.

(51) Int. Cl.
*C12N 1/00* (2006.01)
*A61K 51/00* (2006.01)
*A61M 36/14* (2006.01)
*A61K 35/12* (2006.01)

(52) U.S. Cl.
USPC ........ 435/317.1; 424/1.21; 424/573; 530/810

(58) Field of Classification Search
None
See application file for complete search history.

(56) References Cited

FOREIGN PATENT DOCUMENTS

WO    WO 99/03499 A1    1/1999

OTHER PUBLICATIONS

Norbury et al., May 2004, Science. vol. 304: 1318-1321.*
Demaria, published online Nov. 2004, J. Leuk. Biol. vol. 77: 361-368.*
Ding et al., 2007, Am J. Path. vol. 1714: 513-524.*
Lee et al., Jun. 2005, J. Neurosci. vol. 25: 6016-6024.*
Wallis et al., 1968, J. Virol. vol. 2: 953-954.*
Jang et al., 2010, J. Neurchem. vol. 113: 1263-1274.*
Brantley-Sieders et al., 2006, vol. 66: 10315-24.*
Luo et al., 2003, Am. J. Path. vol. 163: 381-385.*
Kemball et al., 2010, J. Virol. vol. 84:12110-24.*
Gerber et al., Jul. 1 2004, Eur. J. Resp. vol. 24: 40-48.*
Hoffmeyer et al., 2005, Canc. cell Int. vol. 5: 1-10.*
Picinini et al., 2001, J. Biochem. vol. 356: 835-841.*
Stomhaug et al., 1998, Biochem J. vol. 335: 217-224.*
Li et al., 2011, Clin. Canc. res. vol. 17: 7047-7057.*
Kloetzel and Ossendrop, "Proteasome and Peptidase Function in MHC-Class-I-Mediated Antigen Presentation," *Curr. Opin. Immunol.*16:76-81, 2004.
Voo et al., "Evidence for the Presentation of Major Histocompatibility Complex Class I—Restricted Epstein-Barr Virus Nuclear Antigen 1 Peptides to CD8+ T Lymphocytes," *J. Exp. Med.* 199:459-470, 2004.
Yewdell et al., "Making Sense of Mass Destruction: Quantitating MHC Class I Antigen Presentation," *Nat. Rev. Immunol.* 3:952-961, 2003.
Schubert et al., "Rapid Degradation of a Large Fraction of Newly Synthesized proteins by Proteasomes," *Nature* 404:770-774, 2000.

* cited by examiner

*Primary Examiner* — Amy Juedes
(74) *Attorney, Agent, or Firm* — Klarquist Sparkman, LLP

(57) ABSTRACT

Methods are disclosed for producing defective ribosomal products (DRiPs) in blebs (DRibbles) by contacting cells with a proteasome inhibitor, and in some examples also an autophagy inducer, thereby producing treated cells. DRibbles can be used to load antigen presenting cells (APCs), thereby allowing the APCs to present the DRiPs and antigenic fragments thereof. Immunogenic compositions that include treated cells, isolated DRibbles, or DRibble-loaded APCs are also disclosed. Methods are also provided for using treated cells, isolated DRibbles, or DRibble-loaded APCs to stimulate an immune response, for example in a subject. For example, DRibbles obtained from a tumor cell can be used to stimulate an immune response against the same type of tumor cells in the subject. In another example, DRibbles obtained from a pathogen-infected cell or cell engineered to express one or more antigens of a pathogen can be used to stimulate an immune response against the pathogen in the subject.

40 Claims, 9 Drawing Sheets

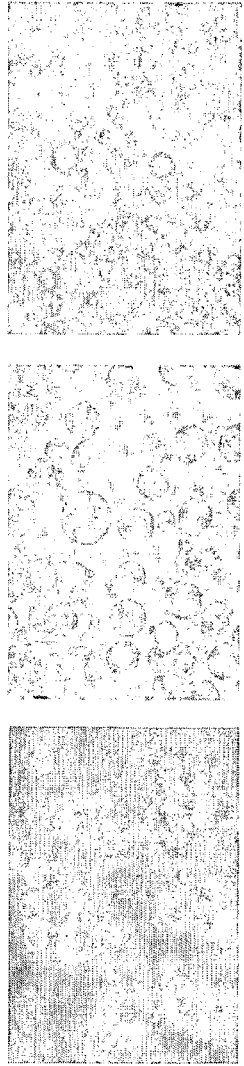
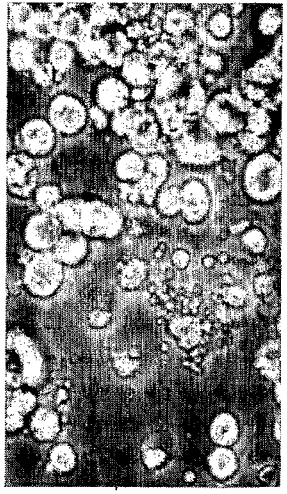
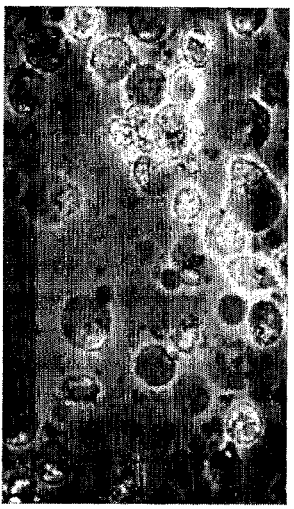

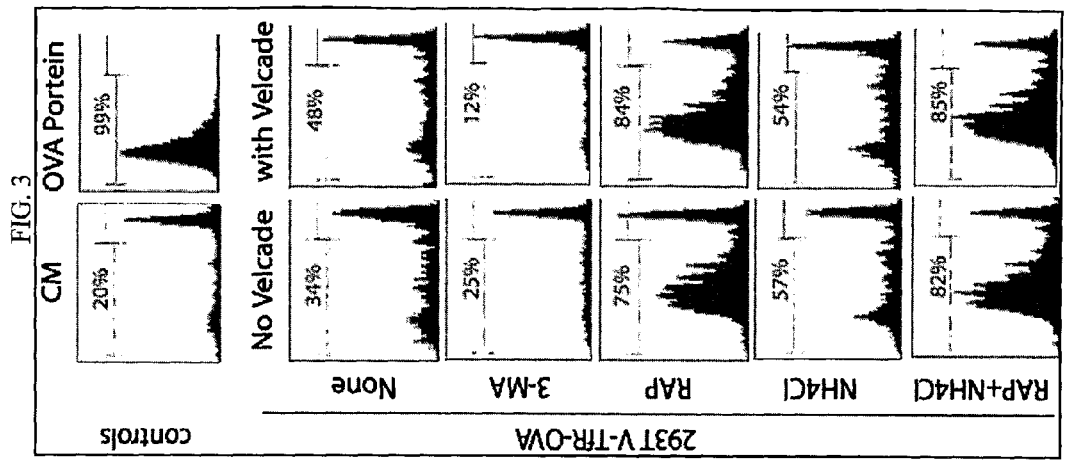
FIG. 3
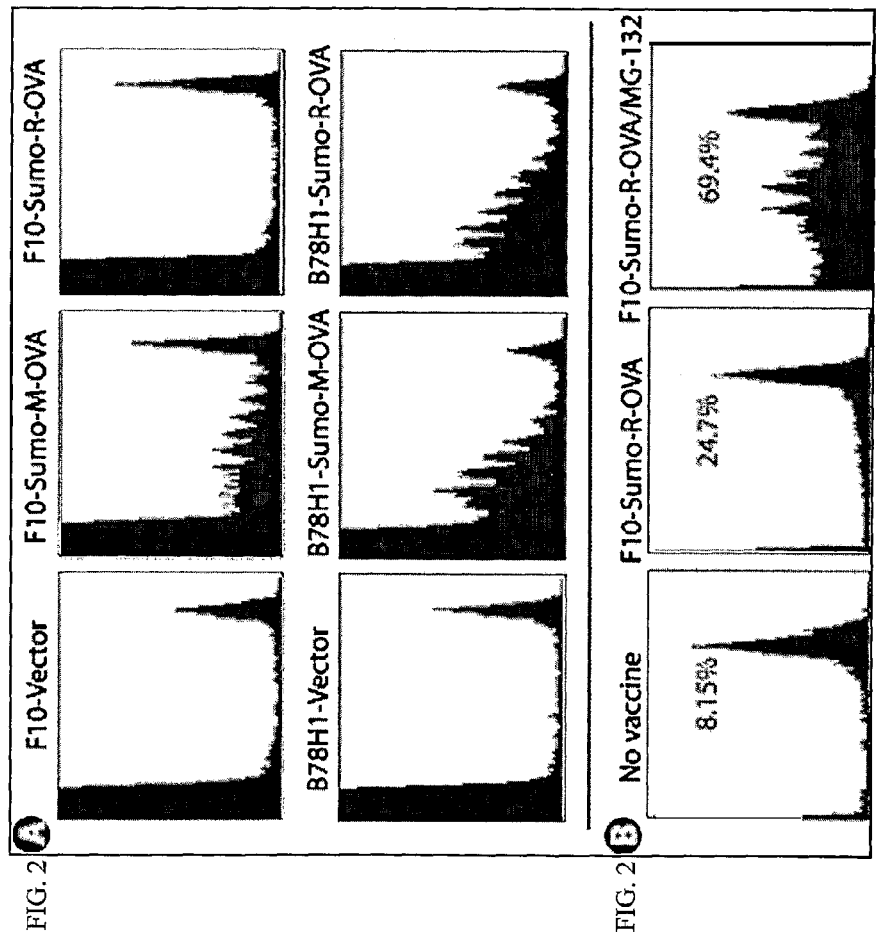
FIG. 2

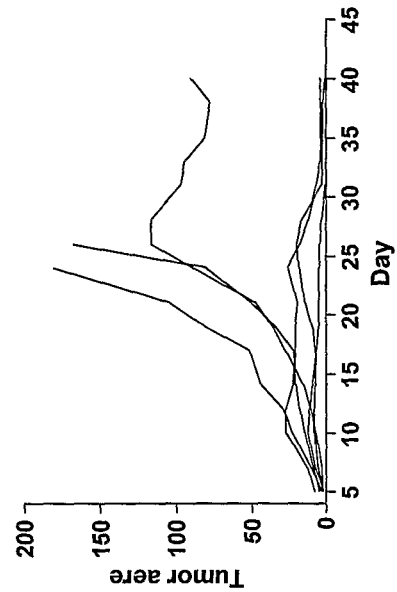
Fig. 10A 3LL/alone
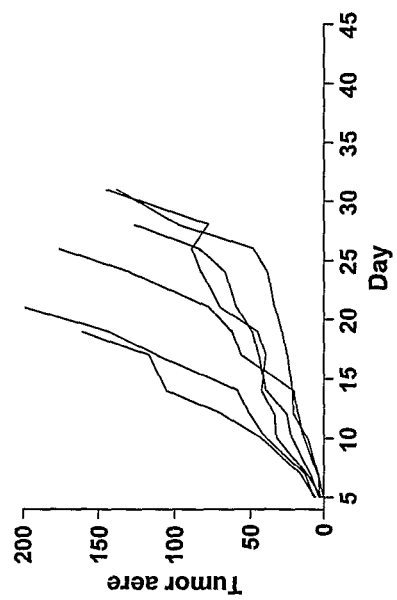
Fig. 10B 6days-3LL/DC-dribble
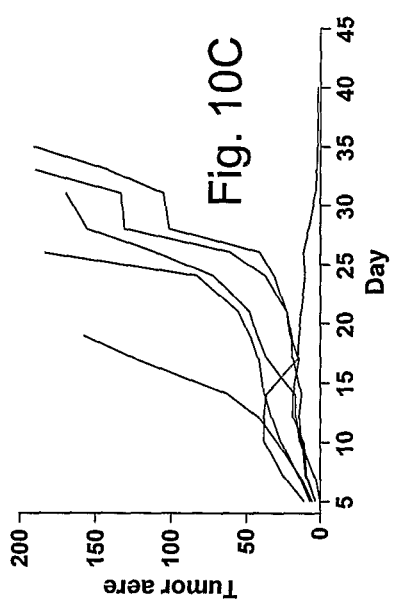
Fig. 10C 9days 3LL/Dribble
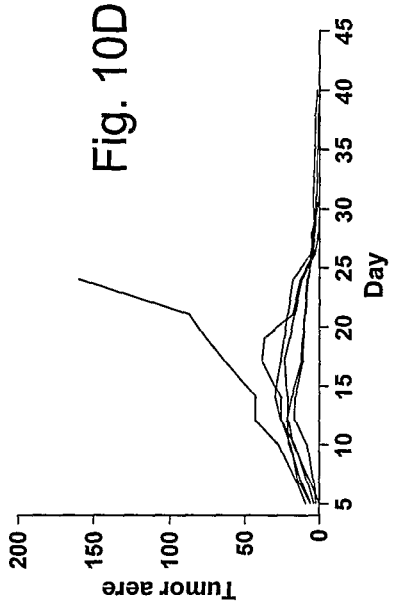
Fig. 10D 12days 3LL/Dribble/aOX40

SEQUENCE LISTING

```
<160> NUMBER OF SEQ ID NOS: 1

<210> SEQ ID NO 1
<211> LENGTH: 20
<212> TYPE: RNA
<213> ORGANISM: Human immunodeficiency virus

<400> SEQUENCE: 1
gcccgucugu ugugugacuc                                              20
```

DEFECTIVE RIBOSOMAL PRODUCTS IN BLEBS (DRIBBLES) AND METHODS OF USE TO STIMULATE AN IMMUNE RESPONSE

CROSS-REFERENCE TO RELATED APPLICATIONS

This application is the U.S. National Stage of International Application No. PCT/US2006/029404, filed Jul. 27, 2006 (published in English under PCT Article 21(2)), which claims the benefit of U.S. Provisional Application No. 60/703,675 filed Jul. 29, 2005, herein incorporated by reference in its entirety.

FIELD

This application relates to methods of stimulating or enhancing an immune response, for example by using defective ribosomal products in blebs (DRibbles), and methods of producing DRibbles from a cell, for example using a proteasome inhibitor.

BACKGROUND

Cross-presentation of exogenous antigens to cytolytic T cells (CTL) by dendritic cells (DC) relies on the major cellular proteolysis machinery, the proteasome, to digest long polypeptides into small fragments, which can associate with cell surface molecules (MHC class I) which form the specific ligands that trigger T-cell activation. In contrast, presentation of exogenous antigens to helper T-lymphocytes (HTL) by dendritic cells primarily depends on the lysosomal pathway; proteases inside lysosomes contribute to the digestion of internalized proteins and digested small peptide fragments are then loaded on MHC class II molecules to activate naïve HTL.

Tumor cells process antigens that can be recognized by T lymphocytes (T cells) and activated cytolytic T cells (CTL) that constantly circulate and seek to destroy tumor cells (Hu, H. M., Chu, Y. & Urba, W. J. Undefined-antigens as vaccines. Cancer Treatment and Research (ed Kheif, S.) 207-226, Kluwer Academic Publishers, New York, 2005). Therefore, methods of treating cancer using cancer immunotherapy have been proposed to generate therapeutic T cells that are reactive to tumor-associated antigens above the threshold level required to mediate regression of established tumors and prevent tumor recurrence.

Unfortunately, despite considerable effort by many investigators for many years, specific active immunization with cancer vaccines has not been very effective in animal models or in clinical trials (Rosenberg et al., Nat. Med. 10:909-15, 2004). The primary obstacle to the success of cancer immunotherapy has been the inability of the vaccine to induce initially a large expansion and then persistence of tumor-reactive CTL (Rosenberg et al., Nat. Med. 10:909-15, 2004). Another obstacle to currently available methods of cancer immunotherapy is that potential tumor rejection antigens are not known for most cancers, with the exception of melanoma, and the dominant tumor rejection antigens are likely tumor or patient-specific.

Although various strategies have been developed in recent years, including gene-modified tumor vaccines, heat shock proteins derived from tumors, dendritic cells loaded with tumor lysates or transfected with tumor derived RNA, fusion of tumor and dendritic cells; and exosomes secreted from tumor cells, their ability to induce a high level of tumor-specific T cells in tumor-bearing hosts has yet to be demonstrated. Therefore, new immunogenic approaches are needed for the treatment of cancer.

SUMMARY

The inventor has determined that reducing or inhibiting cellular protein degradation with a proteasome inhibitor results in cellular accumulation and secretion of defective ribosomal products (DRiPs) and short lived proteins (SLiPs) (as well as immunogenic fragments thereof) into "blebs", structures referred to herein as DRibbles (DRiPs in blebs). It is shown herein that DRibbles released from cells (such as tumor or pathogen infected cells) after proteasome inhibitor-induced autophagy can accumulate DRiPs and SLiPs (and fragments thereof) in autophagy bodies and induce a strong immunity (such as anti-tumor or anti-pathogen) via cross-priming. The disclosed DRibbles can be used in immunotherapy, for example to generate sufficient numbers of tumor- or pathogen-reactive effector/memory T cells in tumor-bearing hosts (or pathogen-infected hosts) above the threshold level required to mediate tumor (or pathogen) regression or prevent tumor (or pathogen) recurrence. Similarly, production of DRibbles in vivo (for example by administration of agents that inhibit proteasome function and agents that induce autophagy) can be used in immunotherapy.

For example, tumor-derived DRibbles, as well as APCs (such as dendritic cells) loaded with tumor-derived DRibbles, can activate tumor-reactive CTL and HTL more efficiently than APCs incubated with live or killed tumor cells, both in vitro and in vivo. In particular examples, administration of DRibbles to a subject (for example as an isolated DRibble population, as a population of cells producing DRibbles, or as DRibble-loaded dendritic cells) increases the generation of CD4 and CD8 cells and promotes the production of inflammatory cytokines or chemokines, such as one or more of IL-6, IL-12, and TNF-α. It also shown in an animal model of lung cancer that dendritic cells (DC) loaded with DRibbles are significantly more effective to mediate regression of established tumors compared to whole tumor cell vaccine that was engineered to produce granulocyte macrophage-colony stimulating factor (GM-CSF). Similarly, it is shown in an animal model of lung cancer that tumor-derived DRibbles in the presence of a chemotherapeutic agent (such as an anti-OX40 antibody) are significantly more effective to mediate regression of well-established tumors compared to the chemotherapeutic agent alone.

Based on these observations, methods of stimulating an immune response against a tumor-specific DRiP (or SLiP) antigen or a pathogen-specific DRiP (or SLiP) antigen are disclosed. In particular examples, such methods induce a rapid expansion of both CD4$^+$ and CD8$^+$ tumor-specific T cells in cancer subjects or induce a large expansion of both CD4 and CD8 pathogen-specific T cells in a subject (such as a subject infected with the pathogen).

Methods are provided for stimulating or enhancing an immune response against one or more DRiPs (or SLiPs), for example an immunogenic DRiP or SLiP fragment, such as tumor-specific DRiPs or pathogen-specific DRiPs. In particular examples, the method includes contacting a cell with a proteasome inhibitor in an amount that does not substantially induce apoptosis of the cell, and under conditions sufficient for the cell to produce DRibbles and allowing the DRiPs to be presented by an antigen presenting cell (APC), thereby stimulating an immune response against one or more DRiPs (such as a DRiP antigen). In some examples, the cells are also contacted with an amount of an agent that induces autophagy, for example rapamycin or culture media that starves the cells (such as HBSS media). In particular examples, the cells are also contacted with an amount of an agent that reduces glycosylation of proteins, for example tunicamycin, sufficient to enhance DRibble production in the presence of the proteasome inhibitor.

The cells can be contacted with the proteasome inhibitor and other agents in vivo, for example by administering the proteasome inhibitor to a subject. In another example, the cells are contacted with the proteasome inhibitor ex vivo (for example in a tissue culture), and the resulting DRibbles contacted with APCs in vivo (for example by administration of a therapeutic amount of the DRibbles to a subject) or the resulting treated cells or DRibbles isolated therefrom contacted with APCs ex vivo and the resulting loaded APCs administered to the subject in a therapeutic amount.

In particular examples, the method includes administering to a subject isolated DRibbles or DRibble-loaded APCs. The DRibbles are obtained from a cell containing the desired DRiPs and fragments thereof, thereby stimulating an immune response against one or more DRiPs in the subject. In some examples, the method includes administering to a subject cells contacted with an amount of proteasome inhibitor (and in some examples also an amount of an agent that induces autophagy) sufficient to inhibit the activity of the proteasome (and in some example induce autophagy) and produce DRibbles by the cells (referred to as treated cells). The cells contain the desired DRiPs, thereby stimulating an immune response against one or more DRiPs in the subject.

In one example, the subject has a tumor and the DRibbles are obtained from a tumor cell of the same type, or the treated cells are of the same type. For example, if the subject has a breast cancer, DRibbles are obtained from a breast cancer cell (such as a breast cancer cell from the same subject, or from another subject, for example a breast cancer cell line) or the treated cells are breast cancer cells. However, non-malignant tumor cells, such as a benign tumor cell, can also be used as a source of DRibbles. In another example, the DRibbles are obtained from a cell infected with a pathogen.

In particular examples, treated cells, isolated DRibbles, or DRibble-loaded APCs are administered in combination with other agents, such as an immunostimulant (such as an adjuvant, for example monophosphoryl lipid A (MPL), CpG, or a cytokine such as granulocyte macrophage-colony stimulating factor (GM-CSF)), an anti-tumor chemotherapeutic agent (such as Taxotere), antibodies against T-cell costimulatory molecules (such as anti-OX40 antibody), agents that inhibit tumor or stromal cell inhibitory ligands (such as agents that inhibit PD-1 signaling), or combinations thereof. In some examples, the subject is administered a lymphodepletion agent prior to administering the treated cells, DRibbles, or DRibble-loaded APCs.

In a specific example, the method is a method of stimulating an immune response against a tumor cell in a subject. For example, the method can include exposing tumor cells to a proteasome inhibitor (and in some example also an agent that induces autophagy) in an amount sufficient for the cell to produce DRibbles, wherein the tumor cells are the same type of tumor cells present in the subject. In some examples, these treated tumor cells are administered to the subject, for example as a whole-cell tumor preparation, thereby stimulating an immune response against one or more tumor DRiPs. In other examples, the resulting DRibbles are isolated, thereby generating a population of isolated DRibbles, and administered to the subject, thereby stimulating an immune response against one or more tumor DRiPs. In some examples, the isolated DRibbles are incubated ex vivo with APCs (such as a dendritic cell) obtained from peripheral blood mononuclear cells (PBMCs) from the subject under conditions sufficient for the APCs to present one or more DRiPs, thereby generating DRibble-loaded APCs. In such an example, the resulting DRibble-loaded APCs are administered to the subject, thereby stimulating an immune response against one or more tumor DRiPs.

Any suitable method of administration can be used, such as subcutaneous (s.c.), intradermal (i.d.), intravenous (i.v.), intraperitoneal (i.p.), or intramuscular (i.m.). In particular examples, the disclosed immunogenic compositions, such as those containing treated cells, isolated DRibbles, or DRibble-loaded APCs are administered in at least two doses, such as at least three doses, over a period of time, such as over a period of at least 180 days.

Methods are provided for producing DRibbles by a cell, for example a mammalian cell. Such methods can be used to stimulate DRibble production, for example increase production of DRibbles by a cell. In particular examples, the method includes contacting a cell with a proteasome inhibitor, such as a reversible proteasome inhibitor, in an amount and under conditions sufficient for producing DRibbles. In some examples, the cell is also contacted with an agent that induces autophagy, such as rapamycin or medium that starves the cells, under conditions sufficient to enhance production of DRibbles by the cell. In some examples, the cell is also contacted with an agent that reduces glycosylation of proteins, such as tunicamycin, under conditions sufficient to enhance production of DRibbles by the cell. The method in some examples further includes harvesting the resulting DRibbles, for example by substantially separating the DRibbles from whole cells and large cell debris. In some examples, DRibbles secreted by the cell are collected. Alternatively (or in addition), intracellular DRibbles can be harvested. In particular examples, harvested DRibbles are isolated to at least 50% purity, such as at least 90% purity.

DRibbles can be produced from any cell from which immunogenic DRiPs are desired. In one example, the cell is a tumor cell, such as a breast cancer cell, a melanoma cell, a renal cell carcinoma cell or a liver cancer cell. In another example, the cell is a cell infected with one or more pathogens, such as a virus, bacterium, protozoa, fungus, or combination thereof. In some examples, the cell is a cell transfected with plasmid or viral vector that includes a nucleic acid molecule encoding one or more pathogenic antigens, such as one or more influenza viral proteins.

In particular examples, the method of producing DRibbles includes contacting a tumor cell with a proteasome inhibitor under conditions sufficient to substantially inhibit protein degradation in a cell, for example for at least 4 hours, such as at least 6 hours, at least 24 hours, or at least 48 hours. In some examples, the method of producing DRibbles further includes contacting a tumor cell with an agent that induces autophagy under conditions sufficient to substantially induce autophagy of the cell, for example for at least 4 hours, such as at least 6 hours, at least 24 hours, or at least 48 hours. If isolation or purification of the DRibbles is desired, the tumor cells can be centrifuged under conditions sufficient to pellet the cells but not the DRibbles (such as low-speed centrifugation). The resulting supernatant containing DRibbles is collected and centrifuged under conditions sufficient to pellet the DRibbles (such as high-speed centrifugation). The pellet containing DRibbles is then collected, for example for loading antigen presenting cells (APCs) or generating an immunogenic composition.

Also provided by the present disclosure are isolated DRibbles produced using the disclosed methods, and immunogenic compositions that include isolated DRibbles.

Methods are disclosed for producing an immunogenic composition. In particular examples, the method includes contacting isolated DRibbles with an APC, such as a dendritic cell (DC), thereby generating an immunogenic composition that includes DRibble-loaded APCs. The method can further include isolating the DRibble-loaded APCs from the DRibbles prior to forming the immunogenic composition. Also provided by the present disclosure are immunogenic compositions produced by such a method.

The foregoing and other objects, features, and advantages of the disclosure will become more apparent from the following detailed description, which proceeds with reference to the accompanying figures.

BRIEF DESCRIPTION OF THE DRAWINGS

FIGS. 1A-C are digital images showing the secretion and isolation of tumor-derived DRibbles. (A) DRibbling of F10 melanoma cells after overnight treatment with proteasome inhibitor; (B) intact tumor cells isolated by low-speed centrifugation; (C) DRibbles isolated by high-speed centrifugation from the supernatant after slow-speed centrifugation.

FIGS. 1D-G are digital images showing the increased production of tumor-derived DRibbles in the presence of proteasome inhibitor and tunicamycin. (D) Untreated 3LL tumor cells; (E) 3LL cells treated with proteasome inhibitor MG-132; (F) 3LL cells treated with tunicamycin; and (G) 3LL cells treated with MG-132 and tunicamycin.

FIGS. 2A and 2B show flow cytometry analysis of cross-presentation of OVA by F10 and B78H1 melanoma cells expressing Sumo-M-OVA or Sumo-R-OVA and the effect of proteasome inhibition on the cross-presentation of OVA from F10-Sumo-R-OVA cells. (A) cross-presentation of OVA by F10 and B78H1 cell lines in vivo. (B) cross-presentation of OVA from F10-Sumo-R-OVA after proteasome inhibition. F78H1-Sumo-M-OVA was used as the control. The histograms show the CFSE-profile of gated CD8+ T cells.

FIG. 3 shows flow cytometry analysis demonstrating that cross-presentation is autophagy-dependent.

FIGS. 10A-D are graphs showing tumor regression induced by administration of DRibble-loaded DC alone or in combination with anti-OX40 antibody in 6-12 day established 3LL lewis lung carcinoma tumor model. Each line represents the data for a single mouse. Mice were injected with $5 \times 10^6$ 3LL tumor cells and either (A) untreated, or treated with DC loaded with DRibbles derived from 3LL tumor cells at (B) day 6, (C) day 9, or (D) day 12. Only mice in day 12 group also received 100 µg anti-mouse OX40 antibody.

DETAILED DESCRIPTION OF SEVERAL EMBODIMENTS

Abbreviations and Terms

Figure 5:
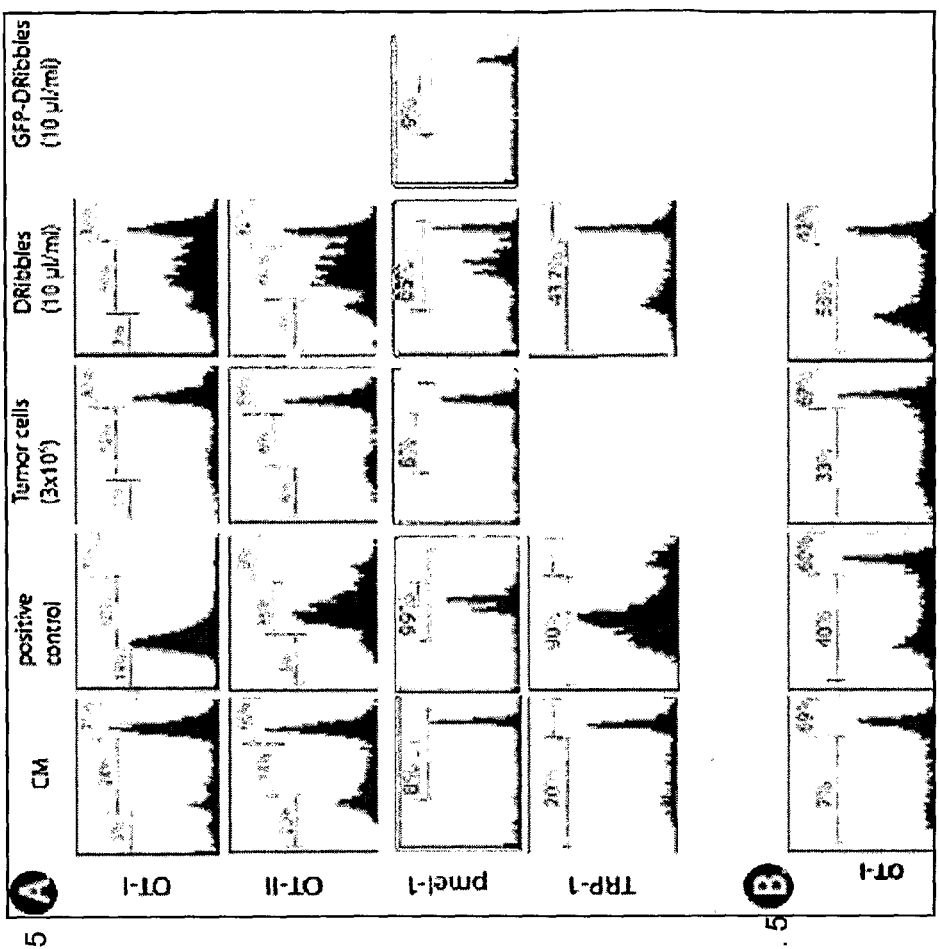
FIGS. 5A and 5B show flow cytometry analysis demonstrating that cross-presentation of DRibbles in vitro and in vivo is more efficient than tumor cells.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an autophagy inducer" includes single or plural autophagy inducers and is considered equivalent to the phrase "comprising at least autophagy inducer." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

| | |
|---|---|
| APC | antigen-presenting cell |
| CM | complete medium |

| | |
|---|---|
| CTL | cytotoxic T lymphocyte |
| DC | dendritic cell |
| DRiPs | defective ribosomal products |
| DRibbles | DRiPs in Blebs |
| ER | endoplasmic reticulum |
| ERAD | ER-associated degradation |
| GM-CSF | granulocyte macrophage-colony stimulating factor |
| HTL | helper T lymphocyte |
| IFN-γ | interferon gamma |
| MHC | major histocompatibility complex |
| PBMC | peripheral blood mononuclear cell |
| PD-1 | programmed death-1 |
| SLiPs | short lived proteins |

Adjuvant: The immunogens disclosed herein (such as treated cells, isolated DRibbles, or DRibble-loaded APCs) can be used in combination with an adjuvant. An adjuvant is an agent that when used in combination with an immunogenic agent augments or otherwise alters or modifies a resultant immune response. In some examples, an adjuvant increases the titer of antibodies induced in a subject by the immunogenic agent. In another example, if the antigenic agent is a multivalent antigenic agent, an adjuvant alters the particular epitopic sequences that are specifically bound by antibodies induced in a subject.

Exemplary adjuvants that can be used with any of the immunogens disclosed herein (such as a tumor- or pathogen infected cell-derived DRibbles) include, but are not limited to, Freund's Incomplete Adjuvant (IFA), Freund's complete adjuvant, B30-MDP, LA-15-PH, montanide, saponin, aluminum salts such as aluminum hydroxide (Amphogel, Wyeth Laboratories, Madison, N.J.), alum, lipids, keyhole lympet protein, hemocyanin, edestin, the MF59 microemulsion, a mycobacterial antigen, vitamin E, non-ionic block polymers, muramyl dipeptides, polyanions, amphipatic substances, ISCOMs (immune stimulating complexes, such as those disclosed in European Patent EP 109942), vegetable oil, Carbopol, aluminium oxide, oil-emulsions (such as Bayol F or Marcol 52), bacterial toxins (such as *B. anthracis* protective antigen, *E. coli* heat-labile toxin (LT), *Cholera* toxin, tetanus toxin/toxoid, diphtheria toxin/toxoid, *P. aeruginosa* exotoxin/toxoid/, pertussis toxin/toxoid, and *C. perfringens* exotoxin/toxoid), bacterial wall proteins and other products (such as cell walls and lipopolysaccharide (LPS)) and combinations thereof.

In one example, the adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199, and GM-CSF or other immunomodulatory cytokines, such as IL-2, IL-7, IL-15 and IL-21.

In one example, the adjuvant includes ssRNA or dsRNA, such as ssRNA single strand oligoribonucleotides (ORN). For example, an adjuvant can include a GU-rich RNA from HIV (such as GCCCGUCUGUUGUGUGACUC; SEQ ID NO: 1; *Science* 303(5663):1526-9, 2004).

In another example, a synthetic adjuvant includes R848 (a TLR7/8 ligand) (3M pharmaceutical) or α-galcer (a NKT cell ligand).

Administration: To provide or give a subject an agent, such as an immunogenic or proteasome inhibitor composition disclosed herein, by any effective route. Exemplary routes of administration include, but are not limited to, oral, injection (such as subcutaneous, intramuscular, intradermal, intraperitoneal, and intravenous), sublingual, rectal, transdermal, intranasal, vaginal and inhalation routes.

Antibody: A molecule including an antigen binding site which specifically binds (immunoreacts with) an antigen. Includes immunoglobulin molecules and immunologically active portions thereof. Immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Antigen: A substance that can stimulate the production of antibodies or a T-cell response in a mammal, including compositions that are injected or absorbed into a mammal. An antigen reacts with the products of specific humoral or cellular immunity, including those induced by heterologous immunogens. The term "antigen" includes all related antigenic epitopes. In one example, an antigen is a DRiP or a SLiP (or an immunogenic fragment thereof), or a DRibble containing DRiPs or SLiPs. A target antigen is an antigen against which an immune response is desired, for example to achieve a therapeutic effect, such as tumor regression or treatment of an infection.

Antigen-presenting cell (APC): A cell that carries on its surface antigen bound to MHC class I or class II molecules and presents the antigen in this context to T cells. APCs include, but are not limited to, monocytes, macrophages, dendritic cells, B cells, and Langerhans cells. Among these cells, dendritic cells and B cells are regarded as professional APC.

Antigen-specific T cell: A $CD8^+$ or $CD4^+$ lymphocyte that recognizes a particular antigen. Generally, antigen-specific T cells specifically bind to a particular antigen presented by MHC molecules, but not other antigens presented by the same MHC.

Autophagy: A cellular recycling pathway in which both cytoplasm and organelles are engulfed within double-membrane vesicles, autophagosomes, and fused with lyosomes for degradation. Autophagy plays a role in cell survival and death and has been implicated in development, aging, neurodegeneration, and cancer, as well as in the innate defense against intracellular pathogens, acquired immunity (such as MHC II restricted antigen processing of endogenous antigens), and virus replication.

The rate of autophagy increases when the cell is contacted with an autophagy inducer. For example, autophagy increases when cells are subjected to nutrient deprivation, for example by incubation in HBSS media, and also when it receives stimuli that result in organelle proliferation. For example, contacting cells with agents that inhibit blocking proteasome function for prolonged periods can induce autophagy (for example by incubation of cells in 20-1000 nM Velcade). Similarly, agents such as rapamycin, tamoxifen, IFN-γ and vinblastine can induce autophagy. In one example, cells are incubated under ischemic conditions that result in induction of autophagy by the cells.

Cancer: Malignant neoplasm that has undergone characteristic anaplasia with loss of differentiation, increased rate of growth, invasion of surrounding tissue, and is capable of metastasis.

Chemotherapy: In cancer treatment, chemotherapy refers to the administration of one or more agents to kill or slow the reproduction of rapidly multiplying cells, such as tumor or cancer cells. In a particular example, chemotherapy refers to the administration of one or more anti-neoplastic agents to significantly reduce the number of tumor cells in the subject, such as by at least 10%, at least 20%, or at least 50%. Cytotoxic anti-neoplastic chemotherapeutic agents include, but are not limited to: 5-fluorouracil (5-FU), azathioprine, cyclophosphamide, antimetabolites (such as Fludarabine), and other antineoplastics such as Etoposide, Doxorubicin, methotrexate, Vincristine, carboplatin, cis-platinum and the taxanes (such as taxol).

Decrease: To reduce the quality, amount, or strength of something.

In one example, a therapy decreases a tumor (such as the size of a tumor, the number of tumors, the metastasis of a tumor, or combinations thereof), or one or more symptoms associated with a tumor, for example as compared to the response in the absence of the therapy. In a particular example, a therapy decreases the size of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein.

In one example, a therapy decreases the incidence of pathogen infection, or one or more symptoms associated with pathogen infection, for example as compared to the absence of the therapy. In a particular example, a therapy decreases the incidence of pathogen infection, or one or more symptoms associated with pathogen infection if the incidence or symptoms of pathogen infection are decreased subsequent to the therapy, such as a decrease of at least 10%, at least 20%, at least 50%, or even at least 90%. Such decreases can be measured using the methods disclosed herein.

Dendritic cell (DC): An antigen presenting cell that possess the ability to stimulate naïve T cells, by recognizing, processing and presenting foreign antigens to the T-cells. One particular example of a dendritic cell is a Langerhans cell, a species of dendritic cell resident in skin.

DRiPs (Defective ribosomal products): Peptides that result from errors in translation, or from properly translated but misfolded proteins, that were subjected to quality control systems such as ER-associated protein degradation (ERAD). DRiPs are produced entropically, due to the imperfections inherent to protein synthesis and folding. DRiPs may account for one-third of newly synthesized proteins that are degraded by proteasomes within 30 minutes of their synthesis. DRiPs provide a major source of peptides associated with MHC class I molecules. In some examples, reference to DRiPs includes immunogenic fragments thereof.

DRibbles (DRiPs in Blebs): The DRiP or SLiP-filled structure formed by cells, the formation of which can be enhanced when cells are exposed to a proteasome inhibitor. Such structures, such as vesicles, are in some examples secreted by the proteasome inhibitor-exposed cells, thereby permitting isolation of DRibbles from the culture supernatant, for example using centrifugation. In particular examples, DRibbles are autophagy bodies.

Epitope: An antigenic determinant, such as a chemical group or peptide sequence that elicits a specific immune response. An antibody binds a particular antigenic epitope, or a T-cell reacts with a particular antigenic epitope bound to a specific MHC molecule. In some examples, an epitope has a minimum sequence of 6-10 amino acids, such as 6, 7, 8, 9, or 10 amino acids for MHC class I, or even longer for MHC class II (such as a maximum sequence of about 100 amino acids). In a particular example, an epitope is present in a tumor-associated or pathogen-associated antigen.

Enhance: To improve the quality, amount, or strength of something.

In one example, a therapy enhances the immune system if the immune system is more effective at fighting infection or tumors, as compared to immune function in the absence of the therapy. For example, a therapy can enhance the immune system if the survival time of the subject is prolonged, if the size of a tumor in the subject decreases, if metastasis of a tumor decreases in the subject, if an infection is treated in a subject, or combinations thereof, in the presence of the therapy.

In a particular example, a therapy enhances the immune system if the amount of IFN-γ secreted by tumor-specific T-cells increases subsequent to the therapy, such as an increase of at least 10%, at least 20%, at least 50%, or even at least 90%. Such enhancement can be measured using the methods disclosed herein, for example determining an amount of INF-γ secretion using an ELISA assay or flow cytometry.

In a particular example, a therapy enhances the immune system if the number of lymphocytes increases subsequent to the therapy, such as an increase of at least 10%, at least 20%, at least 50%, or even at least 90%. Such enhancement can be measured using methods known in the art for example determining the number of lymphocytes before and after the therapy using flow cytometry.

In another particular example, a therapy enhances production or secretion of DRibbles from a cell, such as a tumor or a pathogen infected cell, such as an increase of at least 10%, at least 20%, at least 50%, or even at least 90%. Such enhancement can be measured using methods known in the art for example determining an amount of DRibbles before and after the therapy.

In yet another example, a therapy enhances the frequency of tumor-specific T cells in a subject, such as an increase of at least 20%, at least 30%, at least 50%, or at least 90%. In a particular example, in the absence of a therapy, the frequency of tumor-specific T cells is undetectable or less than 0.1%, while in the presence of an effective therapy the number of T cells is at least 0.1%, such as at least 100%, wherein the percentage is relative to the total number of T cells in a sample, such as a biological sample obtained from a mammal.

Harvest: To collect. For example, when harvesting secreted DRibbles, the method can include separating the DRibbles from cells, for example by centrifugation.

Immune response: A change in immunity, for example a response of a cell of the immune system, such as a B-cell, T-cell, macrophage, monocyte, or polymorphonucleocyte, to an immunogenic agent in a subject. The response can be specific for a particular antigen (an "antigen-specific response"), such as a tumor-specific or pathogen-specific DRiP or SLiP. In a particular example, an immune response is a T cell response, such as a CD4$^+$ response or a CD8$^+$ response. In another example, the response is a B-cell response, and results in the production of specific antibodies to the immunogenic agent.

In some examples, such an immune response provides protection for the subject from the immunogenic agent or the source of the immunogenic agent. For example, the response can protect a subject, such as a human or veterinary subject, from infection by a pathogen, or interfere with the progression of an infection by a pathogen. In another example, the response can treat a subject having a tumor, for example by interfering with the metastasis of the tumor. An immune response can be active and involve stimulation of the subject's immune system, or be a response that results from passively acquired immunity.

In a particular example, an increased or enhanced immune response is an increase in the ability of a subject to fight off a disease, such as a pathogen infection or a tumor.

Immunity: The state of being able to mount a protective response upon exposure to an immunogenic agent. Protective responses can be antibody-mediated or immune cell-mediated, and can be directed toward a particular pathogen or tumor (such as a pathogen or tumor specific DRiP). Immunity can be acquired actively (such as by exposure to an immunogenic agent, either naturally or in a pharmaceutical composition, such as a composition that includes DRibbles) or passively (such as by administration of antibodies or in vitro stimulated and expanded T cells).

Immunogen: An agent (such as a compound, composition, or substance) that can stimulate or elicit an immune response by a subject's immune system, such as stimulating the production of antibodies or a T-cell response in a subject. Immunogenic agents include, but are not limited to, DRiPs and SLiPs, such as those present in DRibbles. One specific example of an immunogenic composition is a vaccine (such as a vaccine that includes DRibbles).

Immunogenicity: The ability of an immunogen to induce a humoral or cellular immune response. Immunogenicity can be measured, for example, by the ability to bind to an appropriate MHC molecule (such as an MHC Class I or II molecule) and to induce a T-cell response or to induce a B-cell or antibody response, for example, a measurable cytotoxic T-cell response or a serum antibody response to a given epitope. Immunogenicity assays are well-known in the art and are described, for example, in Paul, *Fundamental Immunology*, 3rd ed., 243-247 (Raven Press, 1993) and references cited therein.

Immunologically Effective Dose: A therapeutically effective amount of an immunogen (such as DRibbles or cells treated with agents that promote Dribble formation) that will prevent, treat, lessen, or attenuate the severity, extent or duration of a disease or condition, for example, a tumor, infection by a pathogen, or an infectious disease.

Immunostimulant: The immunogens disclosed herein can be used in combination with an immunostimulant. An immunostimulant is an agent that can stimulate an immune response against an antigen. One example is an adjuvant. Other particular examples include a costimulatory antibody of T-cell proliferation and survival, such anti-CTLA-4 (madarex) or anti-OX-40 antibody.

Infection: Invasion and multiplication of pathogens in a subject, which can cause local cellular injury due to competitive metabolism, toxins, intracellular replication, or antigen-antibody response.

Infectious disease: Any disease caused by an infectious pathogen. In a particular example, it is a disease caused by at least one type of infectious pathogen. In another example, it is a disease caused by at least two different types of infectious pathogens. Infectious diseases can affect any body system, be acute (short-acting) or chronic (long-acting), occur with or without fever, strike any age group, and overlap each other.

Interferon-gamma (IFN-γ): A protein produced by T lymphocytes in response to specific antigen or mitogenic stimulation. Includes naturally occurring IFN-γ peptides and nucleic acid molecules and IFN-γ fragments and variants that retain full or partial IFN-γ biological activity. Sequences for IFN-γ are publicly available (for example, exemplary IFN-γ mRNA sequences are available from GenBank Accession Nos: BC070256; AF506749; and J00219, and exemplary IFN-γ protein sequences are available from GenBank Accession Nos: CAA00226; AAA72254; and 0809316A).

Methods of measuring functional IFN-γ are known, and include, but are not limited to: immunoassays. For example, the public availability of antibodies that recognize IFN-γ permits the use of ELISA and flow cytometry to detect cells producing IFN-γ. Another method is a cyotoxicity assay that measures the level of killing of tumor targets by activated T cells (for example see Hu et al., *J. Immunother.* 27:48-59, 2004, and Walker et al., *Clin. Cancer Res.* 10:668-80, 2004).

Isolated: An "isolated" biological component (such as a portion of hematological material, such as blood components, or a portion of a cell, such as a DRibble) has been substantially separated or purified away from other biological components of the organism (or cell) in which the component naturally occurs.

An isolated cell is one which has been substantially separated or purified away from other biological components of the organism in which the cell naturally occurs. For example, an isolated peripheral blood mononuclear cell (PBMC) is a population of PBMCs which are substantially separated or purified away from other blood cells, such as red blood cells or polynuclear cells.

Isolated DRibbles are those which have been substantially separated or purified away from other biological components, such as whole cells or large cell debris.

Lymphodepletion agent: A chemical compound or composition capable of decreasing the number of functional lymphocytes in a mammal when administered to the mammal. One example of such an agent is one or more anti-neoplastic chemotherapeutic agents. In a particular example, administration of a lymphodepletion agent to a subject decreases T-cells by at least 50%. In particular examples, lymphodepletion agents are administered to a subject prior to administration of an immunogen (such as an immunogenic composition that includes DRibbles) to enhance the CTL and HTL expansion and persistence after administration of the immunogen.

Malignant: Cells which have the properties of anaplasia invasion and metastasis.

Neoplasm: Abnormal growth of cells.

Pathogen: A disease-producing agent. Examples include, but are not limited to microbes such as viruses, bacteria, fungi, and protozoa, for example influenza, *Listeria*, and HIV. In some examples, pathogens are used to infect cells, and DRibbles produced therefrom.

Pharmaceutical agent or drug: A chemical compound or composition capable of inducing a desired therapeutic or prophylactic effect when administered to a subject, alone or in combination with another therapeutic agent(s) or pharmaceutically acceptable carriers. In a particular example, a pharmaceutical agent treats a tumor, for example by reducing the size of the tumor (such as the volume of the tumor or reducing the number of tumor cells), reducing metastasis of the tumor, or combinations thereof. In a particular example, a pharmaceutical agent treats (such as prevents) an infection by a pathogen, such as a virus.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic agents, such as one or more immunogenic compositions provided herein.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Programmed death-1 (PD-1): A receptor expressed on the surface of activated lymphocytes, which functions as a negative regulator for immune function to suppress the activated lymphocyte. Tumor cells can utilize PD-1 to escape from the host immune responses. The interactions of the PD-1 ligands PD-L1 (also known as B7-H1) and PD-L2 (also known as B7-DC) with the PD-1 receptor function to limit, terminate, and/or attenuate T cell responses, and may regulate T cell tolerance. Inhibition of the negative regulatory signal mediated by PD-1 may promote the immune response against tumor cells.

Inhibitors of PD-1 function are known, such as antibodies and siRNA molecules specific for PD-1 (such as PD-1 anti-human PD-1) or PD-L1 or PD-L2. For example, the inhibitors of PD-1 biological activity (or its ligands) disclosed in U.S. Pat. Nos. 7,029,674; 6,808,710; or U.S. Patent Application Nos: 20050250106 and 20050159351 can be used in the methods provided herein.

Proteasome: A macromolecular complex present in the nucleus and cytosol of cells that degrades proteins, such as those that have been tagged for elimination, for example damaged or misfolded proteins, and proteins tagged by ubiquitination.

Proteasome inhibitor: An agent that can reduce and in some examples eliminate the proteasome-mediated catabolic pathway that degrades intracellular proteins, such as ubiquitinated proteins. In particular examples, such proteasome inhibitors block the MHC class I antigen processing pathway. Proteasome inhibitors can be reversible (such as MG132) or irreversible (such as lactacystin and epoxomicin).

Particular examples of proteasome inhibitors are peptidyl boronic acid ester and acid compounds. Exemplary proteasome inhibitors include, but are not limited to: carbobenzyloxy-L-leucyl-L-leucyl-L-leucinal (MG-132), carbobenzyloxy-L-leucyl-L-leucyl-L-norvalinal (MG-115), epoxomicin, N-benzyloxycarbonyl-L-leucyl-L-leucyl-L-leucyl boronic acid (MG-262), N-benzyloxycarbonyl-Ile-Glu(O-t-butyl)-Ala-leucinal (PSI; and its epoxide), N-Acetyl-Leu-Leu-norleucinal (MG-101, ALLN, or calpain inhibitor I), MLN519, N-pyrazinecarbonyl-L-phenylalanine-L-leucineboronic acid (bortezomib, PS-341, or Velcade®), lactacystin (Calbiochem-Novobiochem Co., La Jolla, Calif.), PS-273, N-acetyl-Leu-Leu-Met (ALLM or calpain inhibitor II), N-tosyl-Lys chloromethyl ketone (TLCK), N-tosyl-Phe chloromethyl ketone (TPCK), pyrrolidine dithiocarbamate (PDTC), [2S,3S]-trans-epoxysuccinyl-L-leucylamido-3-methylbutane ethyl ester (EST), and pentoxyfilline (PTX).

Purified: The term "purified" does not require absolute purity; rather, it is intended as a relative term. Thus, for example, a purified cell is one in which the cell is more pure than the cell in its natural environment, such as within an organism. Similarly, a purified DRibble is one in which the DRibble is more pure than the DRibble in its natural environment, such as within a cell or culture medium.

In particular examples, purified populations of DRibbles refers to populations of DRibbles that are at least 75% pure, at least 80% pure, at least 90% pure, at least 95% pure, at least 97% pure, at least 98% pure, or at least 99% pure. In one example, a substantially purified population of DRibbles is composed of at least 95% DRibbles, that is, the population of DRibbles includes less than about 5% of whole cells or large cell debris. The purity of a DRibble population can be measured based on size or by ability to stimulate a particular immune response (for example, as measured by an ELISA assay), as compared to a control.

Short lived protein (SLiP): A normal protein having a short half life, which in particular examples is immunogenic and recognized by T cells. In one example, a SLiP is translated with unconventional initiation codons, such as CUG instead of AUG. SLiPs have been identified in viruses (for example HIV and other retroviruses) and tumor cells. One particular example of a SLiP is a DRiP. In some examples, reference to SLiPs includes immunogenic fragments thereof.

Specifically binds: To substantially or completely selectively bind with a single binding affinity for a particular antigen/epitope with which it immunoreacts. Examples include antigens and T cells that selectively immunoreact with a target antigen (such as a tumor- or pathogen-specific DRiP or SLiP). In a particular example of specific binding, a T cell receptor on a target antigen-specific T cell specifically recognizes and reacts with a target antigen presented on an APC, such as an MHC complex, wherein the binding is a non-random binding reaction between the T cell receptor and a target antigenic determinant. In a specific example, the desired binding specificity of a target antigen-specific T cell is determined from the reference point of the ability of the T cell receptor on the target antigen-specific T cell to bind to an APC presenting the target antigen, but not an unrelated antigen, and therefore distinguish between two different antigens.

Stimulate proliferation: To increase the growth or reproduction of cells, for example to increase the number of antigen-specific T cells, such as in a subject administered DRibbles or tumor cells treated with an amount of proteasome inhibitor sufficient to produce DRibbles.

Subject: Living multi-cellular vertebrate organisms, a category that includes human and non-human mammals (such as laboratory or veterinary subjects).

Therapeutically effective amount: An amount of an agent that alone, or together with a pharmaceutically acceptable carrier or one or more additional therapeutic agents, induces the desired response. A therapeutic agent, such as an immunogenic composition that includes DRibbles, is administered in therapeutically effective amounts that stimulate a protective immune response, for example against a target antigen.

Effective amounts a therapeutic agent can be determined in many different ways, such as assaying for an increase in an immune response, for example by assaying for improvement of a physiological condition of a subject having a disease (such as a tumor or pathogen infection). Effective amounts also can be determined through various in vitro, in vivo or in situ assays.

Therapeutic agents can be administered in a single dose, or in several doses, for example weekly, monthly, or bimonthly, during a course of treatment. However, the effective amount of can be dependent on the source applied, the subject being treated, the severity and type of the condition being treated, and the manner of administration.

In one example, it is an amount sufficient to partially or completely alleviate symptoms of an infectious disease within a subject, or to decrease infection by a pathogen. Treatment can involve only slowing the progression of the disease temporarily, but can also include halting or reversing the progression of the disease permanently, as well as preventing disease in the first place. For example, a pharmaceutical preparation can decrease one or more symptoms of infectious disease, for example decrease a symptom by at least 20%, at least 50%, at least 70%, at least 90%, at least 98%, or even at least 100%, as compared to an amount in the absence of the pharmaceutical preparation.

In another example, it is an amount sufficient to partially or completely alleviate symptoms of a tumor in a subject. Treatment can involve only slowing the progression of the tumor temporarily, but can also include halting or reversing the progression of the tumor permanently. For example, a pharmaceutical preparation can decrease one or more symptoms of the tumor (such as the size of the tumor or the number of tumors), for example decrease a symptom by at least 20%, at least 50%, at least 70%, at least 90%, at least 98%, or even at least 100%, as compared to an amount in the absence of the pharmaceutical preparation.

Transduced: A transduced cell is a cell into which has been introduced a nucleic acid molecule (such as a vector encoding a pathogen antigen) by molecular biology techniques. The term transduction encompasses all techniques by which a nucleic acid molecule can be introduced into a cell, including transfection with viral vectors, transformation with plasmid vectors, and introduction of naked DNA by electroporation, lipofection, and particle gun acceleration. Such methods are routine in the art.

Treated cell: A cell that has been contacted with a desired agent in an amount and under conditions sufficient for the desired response. In one example, a treated cell is a tumor or pathogen-infected cell that has been incubated with a proteasome inhibitor under conditions sufficient for the cell to produce DRibbles, and can further include incubating the cell with an autophagy inducer under conditions for the cell to undergo autophagy.

Treating a disease: "Treatment" refers to a therapeutic intervention that ameliorates a sign or symptom of a disease or pathological condition, such a sign or symptom of infectious disease or a tumor. Treatment can also induce remission or cure of a condition, such as an infectious disease or a tumor. In particular examples, treatment includes preventing a disease, for example by inhibiting the full development of a disease, such as preventing development of an infectious disease or a tumor (such as a metastasis). Prevention of a disease does not require a total absence of infectious disease or a tumor. For example, a decrease of at least 50% can be sufficient.

Tumor: A neoplasm. Includes solid and hematological tumors.

Examples of hematological tumors include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelogenous leukemia, and chronic lymphocytic leukemia), myelodysplastic syndrome, and myelodysplasia, polycythemia vera, lymphoma, (such as Hodgkin's disease, all forms of non-Hodgkin's lymphoma), multiple myeloma, Waldenstrom's macroglobulinemia, and heavy chain disease.

Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, lung cancer, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, meningioma, neuroblastoma and retinoblastoma).

Tumor-associated antigens (TAAs): A tumor antigen which can stimulate tumor-specific T-cell-defined immune responses or antibodies to tumor cells. In one example, a TAA is a target antigen, wherein the target antigen is present in a tumor in the subject to be treated.

Tunicamycin: An antibiotic that blocks glycosylation of newly-synthesized proteins by preventing the transfer of the 14 residue core oligosaccharide from a dolichol phosphate donor molecule to certain asparagines (Asn) residues on the proteins. Another antibiotic agent that blocks glycosylation, and can therefore be used to enhance DRibble production, is Brefeldin A.

Under conditions sufficient for: A phrase that is used to describe any environment that permits the desired activity.

In one example, includes culturing cells (such as tumor cells or cells infected with a target pathogen) in the presence of a proteasome inhibitor sufficient to allow the desired activity. In particular examples, the desired activity is the production of DRibbles by the treated cell. In other particular examples, the desired activity further includes secretion of DRibbles by the cell.

In another example, includes culturing APCs in the presence of DRibbles sufficient to allow the desired activity. In particular examples, the desired activity is presentation of a DRiP antigen by an APC, such as a TAA or pathogen antigen, for example a viral-associated antigen (VAA).

In another example, includes administering treated cells, isolated DRibbles, or DRibble-loaded APCs to a subject sufficient to allow the desired activity. In particular examples, the desired activity is binding between an APC presenting a DRiP or SLiP antigen and a primed T cell.

Unit dose: A physically discrete unit containing a predetermined quantity of an active material calculated to individually or collectively produce a desired effect such as an immunogenic effect. A single unit dose or a plurality of unit doses can be used to provide the desired effect, such as an immunogenic effect.

Vaccine: An immunogenic composition that can be administered to a mammal, such as a human, to confer immunity, such as active immunity, to a disease or other pathological condition. Vaccines can be used prophylactically or therapeutically. Thus, vaccines can be used reduce the likelihood of infection or to reduce the severity of symptoms of a disease or condition or limit the progression of the disease or condition (such as a tumor).

In one example, a vaccine includes isolated DRibbles obtained from a tumor or pathogen-infected cell. In another example, a vaccine includes a treated cell (such as a whole cell tumor composition that has been treated with a proteasome inhibitor).

Vector: A nucleic acid molecule as introduced into a host cell, thereby producing a transformed host cell. A vector can include nucleic acid sequences that permit it to replicate in a host cell, such as an origin of replication. A vector can also include one or more selectable marker genes and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. In a particular example, a vector includes a nucleic acid molecule that encodes one or more pathogen antigens, such as a *Listeria* peptide.

Viral-associated antigen (VAAs): A viral antigen which can stimulate viral-specific T-cell-defined immune responses.

Methods of Stimulating an Immune Response

Antigen intake by APCs occurs via phagocytosis of cell-associated or particular antigens, pinocytosis of soluble proteins, and receptor-mediated endocytosis. The majority of internalized antigens utilize the proteasome-dependent ER-associated protein degradation pathway (ERAD) for cross-presentation. However, certain antigens can be processed by endosomal proteases and cross-presented via the vacuolar pathway and operated independently of transporter associated proteins (TAPs) and proteasomes. It is shown herein that when cellular protein degradation is reduced or inhibited with a proteasome inhibitor, cells accumulate and secrete DRiPs into "bleb" structures (DRibbles). It is proposed that this inhibition of the proteasome induces autophagy and secretion of short-lived proteins (DRiPs and SLiPs) into autophagy bodies termed DRibbles. Unexpectedly, the inventor has observed that these DRibbles containing DRiPs and SLiPs (as well as immunogenic fragments thereof) act as precursors or stimulators for cross-presentation. Cross-presented antigens are ideally expressed at high levels and are stable and have a long half-life. In contrast, DRiPs and SLiPs are short-lived proteins, and even if they are synthesized at high levels they are rapidly destroyed (for example by tumor cells) before they can be delivered to DC for cross-presentation. Therefore, inhibiting proteasome-mediated degradation of DRiPs and SLiPs can greatly increase cross-presentation of these short-lived proteins by host professional APC, such as DC, for example to tumor cells or cells infected with a pathogen.

Based on these observations, the present application provides methods of stimulating an immune response against one or more DRiPs or other SLiPs, such as immunogenic fragments thereof. The disclosed methods can use DRiPs or SLiPs (as well as immunogenic fragments thereof) for cross-priming. In particular examples, the method includes contacting a cell with one or more proteasome inhibitors, for example in an amount that does not substantially induce apoptosis of the cell, under conditions sufficient for the cell to produce DRibbles, and then allowing the DRiPs to be presented by an APC, thereby stimulating an immune response against one or more DRiPs. It is proposed that DRibbles are autophagy bodies released from cells (such as a tumor cell or a cell infected with a target pathogen) upon prolonged proteasome inhibition. The cell can be contacted with one or more proteasome inhibitors in vivo, for example by administration of the one or more proteasome inhibitors to the subject to be treated. In other examples, the cell is contacted with one or more proteasome inhibitors ex vivo. For example, a tumor or pathogen infected cell can be incubated with one or more proteasome inhibitors ex vivo, and the treated cells, or DRibbles isolated from the treated cells, administered to the subject in therapeutically effective amounts. Alternatively, a tumor or pathogen infected cell can be incubated with one or more proteasome inhibitors ex vivo, DRibbles isolated from the treated cells, incubating the DRibbles with APC, and administering the treated APCs to the subject in therapeutically effective amounts.

The cells can be contacted with the one or more proteasome inhibitors alone, or in combination with one or more other agents. For example, the cells can also be contacted with one or more agents that reduce, or even inhibit glycoslylation, such as nucleoside translocase I inhibitors. Examples of such agents include, but are not limited to mureidomycin, liposidomycin, antibiotics such as tunicamycin and Brefeldin A, or combinations thereof. In particular examples, contacting the cell with both a proteasome inhibitor and an agent that reduces glycoslylation, increases production of DRibbles by the cell relative to either agent alone. In another or additional example, the cells are also contacted with an immunostimulant, such as an adjuvant (such as a CpG, MLA) or a cytokine, for example GM-CSF. In another or additional example, the cells are also contacted with an autophagy inducer in an amount sufficient to induce autophagy of the cells. Such agents induce autophagy by the cells. Examples of autophagy inducers include culture media that starves cells (such as HBSS) and rapamycin. In another or additional example, the cells are also contacted with an agent that inhibits lysosome mediated protein degradation, such as $NH_4Cl$.

Contacting a cell with one or more proteasome inhibitors (alone or in combination with other agents described herein) can be performed in vivo or ex vivo. For example, if the cell is present in a subject, contacting the cell with the proteasome inhibitor can include administering a therapeutically effective amount of the proteasome inhibitor to the subject, thereby stimulating an immune response to one or more DRiP antigens. In particular examples, the proteasome inhibitor is administered to the subject in an amount that does not significantly result in apoptosis of the cell, such as a sub-lethal dose of the proteasome inhibitor.

In another example, the cell is contacted with one or more proteasome inhibitors (alone or in combination with other agents described herein) ex vivo. For example, cells in culture, such as a tumor cell or cell infected with a pathogen, can be incubated in the presence of one or more proteasome inhibitors (alone or in combination with other agents described herein) under conditions sufficient to substantially reduce protein degradation by the cell, thereby producing DRibbles. The produced DRibbles can be administered to a subject in therapeutic amounts to stimulate an immune response against one or more DRiPs (or SLiPs), or can be used to load APCs as described herein. Alternatively, the treated cells can be directly administered to the subject (without first isolating the DRibbles) in an amount sufficient to stimulate an immune response in the subject against DRiPs, for example as a whole cell tumor immunogenic composition.

Similarly, allowing the DRiPs to be presented by an APC can be performed in vivo or ex vivo. For example, DRibbles produced ex vivo, for example in tissue culture, can be incubated with APCs (such as DC) ex vivo under conditions sufficient to permit the APCs to load the DRibbles and present DRiPs. The DRibble-loaded APCs that can present DRiPs can be administered to a subject in an amount sufficient to stimulate an immune response in the subject against the DRiPs. In another example, the DRibble-loaded APC are cultured with T cells from the subject under conditions sufficient to stimulate and expand tumor-reactive T cells. The resulting tumor-reactive T cells can be administered to a subject at a dose sufficient to treat a tumor or pathogen infection in the subject. In another example, DRibbles produced ex vivo are administered to a subject to stimulate an immune response against one or more DRiPs (or SLiPs). If the DRibbles are produced in vivo, for example by administration of a proteasome inhibitor to a subject, the DRiPs are presented by an APC in vivo. Similarly if cells treated with a proteasome inhibitor are administered to the subject, DRiPs are presented by an APC in vivo.

In particular examples, the method is a method of stimulating an immune response against a tumor in a subject. In such examples, the method can further include administration of therapeutically effective amounts of agents to the subject that reduce or inhibit the activity of tumor or stromal inhibitory molecules, such as programmed death 1 (PD-1) and its ligands PD-1L1 and PD-1L2. For example, such agents can be administered in an amount that significantly increases the number of tumor-infiltrating T cells (for example an increase of at least 20% or at least 50%), thereby enhancing treatment of a tumor. In a specific example, the method includes administration to the subject therapeutically effective amounts of antibodies or siRNA molecules specific for PD-1, PD-1L1, PD-1L2, or combinations thereof, which significantly increase the number of tumor-infiltrating T cells. In a particular example, the method includes administration to the subject therapeutically effective amounts of antibodies or siRNA molecules specific for PD-1, PD-ILL, PD-1L2, or combinations thereof. In other or additional examples, the method can also include significantly reducing the number of functional lymphocytes in the subject, prior to administration of a proteasome inhibitor, or an immunogenic composition that includes DRibbles or DRibble-loaded APCs. For example, one or more lymphodepletion agents can be administered to the subject to reduce the number of functional lymphocytes present in the subject. In another or additional example, the method includes reconstituting the immune system of the lymphodepleted subject, for example by administration of functional lymphocytes previously obtained from the subject. In yet another example, the method includes obtaining blood cells from the subject prior to administration of a lymphodepletion agent.

Stimulating an Immune Response Against a Tumor

In particular examples, the method is a method of stimulating an immune response against a tumor, such as tumor-derived DRiPs. Non-limiting tumors include benign tumors such as pituitary adenomas and gastrointestinal adenomatous polyps. Exemplary malignant tumors, include, but are not limited to: breast cancer, lung cancer, renal cell carcinoma, or liver cancer. In a particular example, the tumor is a breast cancer.

Although tumor cells produce DRiPs, the DRiPs are not efficiently cross-presented due to their rapid degradation by proteasomes. Because most tumor cells express MHC class I but not class II molecules on their surface, and because cross-presentation favors long-lived proteins and misses DRiPs and SLiPs, a much larger array of antigen repertoire presented by tumor cells are not cross-presented by APCs. In contrast, DRibbles produced by tumor cells due to contact with a proteasome inhibitor (for example in combination with an autophagy inducer) are loaded by APCs, thereby permitting cross-presentation of tumor-derived DRiPs by the APCs.

Therefore, in particular examples the method includes administration of a therapeutically effective amount of a proteasome inhibitor (alone or in combination with other agents, such as an autophagy inducer, tunicamycin, $NH_4Cl$, an immunostimulant, or combinations thereof) to a subject in an amount sufficient to produce DRibbles by the tumor cells (such as a breast cancer cell, lung cancer cell, renal cancer cell, or liver cancer cell, or a benign tumor cell), thereby stimulating an immune response against one or more tumor-derived DRiPs. In particular examples, the proteasome inhibitor is administered at a sub-lethal dose, such as an amount that does not cause significant apoptosis of the tumor by the proteasome inhibitor. In some examples, the method further includes administration of a therapeutically effective amount of an autophagy inducer, such as rapamycin or its analog CCI-779, vinblastine, tamoxifen, IFN-γ. In yet additional examples, the method further includes administration of therapeutically effective amounts of an agent that reduces or inhibits tumor or stromal cell inhibitory molecules, such as PD-1.

In another example, the method includes generating DRibbles or DRibble-loaded APCs ex vivo, and then administering isolated DRibbles or DRibble-loaded APCs to a subject in an amount sufficient to stimulate an immune response against one or more tumor-derived DRiPs. In such examples, DRibbles are generated from a tumor cell of the same type as is present in the subject, for example using the methods described above. For example, if the subject has breast cancer, DRibbles are produced from a breast cancer cell. In some examples, the tumor cells used to produce DRibbles are obtained from the subject to be treated. Therefore, in some examples, the method can include obtaining a sample that includes tumor cells from the subject prior to administration of an immunogenic composition to the subject. The method can further include culturing the tumor cells under conditions sufficient to permit viability, growth, or expansion of the tumor cells. However, as noted above, not all primary tumor cells grow well in culture. As a result, in some examples the tumor cells used to produce DRibbles are obtained from a tumor cell line of the same cell type as the tumor in the subject.

In a particular example, the method is a method of stimulating an immune response against a tumor cell in a subject. In some examples, the method includes exposing tumor cells to a proteasome inhibitor ex vivo under conditions sufficient to produce DRibbles by the tumor cells, wherein the tumor cells are the same type of tumor cells present in the subject. In some examples, the tumor cells are also incubated with an autophagy inducer. In some examples, the tumor cells are obtained from the same subject to be treated. The resulting treated tumor cells can be administered to the subject at a therapeutic dose, for example alone or in the presence of an adjuvant or other immunostimulatory agent, or an anti-tumor agent, thereby stimulating an immune response against one or more DRiPs. Alternatively, DRibbles are isolated from the treated tumor cells and administered to the subject at a therapeutic dose, for example alone or in the presence of an adjuvant or other immunostimulatory agent, or an anti-tumor agent, thereby stimulating an immune response against one or more DRiPs. In some examples, the resulting DRibbles are incubated with an APC obtained from peripheral blood mononuclear cells (PBMCs) from the subject under conditions sufficient for the APC to present one or more DRiPs, thereby generating DRibble-loaded APCs. The resulting DRibble-loaded APCs are administered to the subject at a therapeutic dose (alone or in the presence of another therapeutic agent, such as an immunostimulatory agent or an anti-tumor agent), thereby stimulating an immune response against one or more DRiPs.

The disclosed methods can be used to treat a subject having one or more tumors. For example, administration of a proteasome inhibitor, treated tumor cells, isolated DRibbles, or DRibble-loaded APCs, can reduce one or more symptoms of a tumor, such as the size of a tumor, the number of tumors, or prevent metastasis of a tumor.

Lymphodepletion and Reconstitution

In addition to the initial activation of tumor-reactive T cells, a long-term persistence of these activated T cells in vivo can be obtained. For example, to increase the initial expansion and late persistence of tumor-reactive CTL and HTL, prior to administration of a therapeutically effective amount of a proteasome inhibitor, treated tumor cells, isolated DRibbles, DRibble-loaded APCs, or combinations thereof (such as an immunogenic composition containing two or more of these agents), subjects can be administered one or more agents, that alone, or in combination, substantially lymphodeplete the subject. The lymphodepletion agents are administered under conditions sufficient to achieve lymphodepletion in the subject. In particular examples, a subject is substantially lymphodepleted if the number of lymphocytes in the subject decreases by at least 50%, such as at least 90%, following administration of the lymphodepletion agent.

In particular examples, significantly reducing the white blood cell count in a subject having a tumor prior to administration of a proteasome inhibitor or vaccination with treated tumor cells, isolated DRibbles, or DRibble-loaded APCs, elicits a stronger immune response and more tumor cells are destroyed than if no lymphodepletion agent were administered.

In one example, a lymphodepletion agent is an anti-neoplastic chemotherapeutic agent, such as one or more antineoplastic chemotherapeutic agents. Such agents and dosages are known, and can be selected by a treating physician depending on the subject to be treated. Examples of lymphodepletion agents include, but are not limited to fludarabine, cyclophosphamide, or combinations thereof.

In particular examples, the method further includes lymphodepleting subjects, followed by reconstituting the immune system of the subject. For example, prior to lymphodepletion and administration of a proteasome inhibitor or other immunogenic composition, blood cells (such as monocytes and macrophages) are obtained from the subject, for example by using leukapheresis. The isolated cells can be frozen until a time appropriate for introducing the cells into the subject. For example, thawed lymphocytes can be administered to the subject at the same time as the immunogenic composition is administered, or shortly before or after administration of the proteasome inhibitor or other immunogenic composition. Such reconstitution of the immune system can in particular examples enhance stimulation of the immune system.

Stimulating an Immune Response Against a Pathogen

In particular examples, the method is a method of stimulating an immune response against a pathogen, such as pathogen-derived DRiPs. Examples of pathogens include, but are not limited to, viruses, bacteria, protozoa, and fungi, such as HIV, influenza, and *Listeria*.

Therefore, in particular examples the method includes administration of a therapeutically effective amount of a proteasome inhibitor (for example in combination with a therapeutically effective amount of an autophagy inducer), treated pathogen-infected cells, isolated DRibbles, DRibble-loaded APCs, or combinations thereof, to a subject, thereby stimulating an immune response against one or more pathogen-derived DRiPs. Production of treated pathogen-infected cells, isolated DRibbles, or DRibble-loaded APCs can be achieved using the methods described above for tumors, except that cells infected with the target pathogen are used. For example, DRibbles can be produced from a cell infected with one or more desired pathogens (or transduced with a vector encoding one or more pathogen-specific antigens) using the methods described above. In examples where the DRibbles are produced ex vivo, the cell contacted with the proteasome inhibitor can depend on the pathogen of interest. Ideally, the cell is one that can be infected by the pathogen.

In a particular example, a therapeutically effective amount of a proteasome inhibitor (alone or in combination with other agents, such as an autophagy inducer or an agent that reduces glycoslation of proteins in a cell, such as tunicamycin or Brefeldin A) is administered to a subject having an infection. For example, the amount of proteasome inhibitor administered (for example in combination with an autophagy inducer) can be one sufficient to permit production of DRibbles by pathogen-infected cells of the subject, thereby stimulating an immune response against a pathogen in the subject.

The disclosed methods can be used to treat a subject, for example by preventing infection of the subject by a pathogen, or by treating an existing infection in the subject, such as an infectious disease. In one example, treatment of the subject is prophylactic, for example to prevent future infection or future infectious disease in the subject. In another example, treatment includes reducing one or more symptoms associated with an infectious disease, such as reduction of vomiting, diarrhea, fever or chills, or increasing the number of functional lymphocytes.

In examples where treated pathogen-infected cells, isolated DRibbles, or DRibble-loaded APCs are administered to a subject, the DRibbles or DRibble-loaded APCs used will depend on the infectious disease to be treated. That is, the DRibbles or DRibble-loaded APCs used will correspond to the infectious disease to be treated. Particular examples of infectious diseases caused by a bacterium include, but are not limited to, tuberculosis (caused by *Mycobacterium tuberculosis*); heartworm (caused by *Dirofilaria immitis*); gastric disorders (caused by *Helicobacter pylori*); intestinal disorders (such as those caused by *Escherichia coli*); pulmonary disorders (such as those caused by *Haemophilus influenzae*) and pneumoniae (such as those caused by *Streptococcus pneumoniae, Staphylococcus aureus, Pseudomonas aeruginosa*, and *Klebsiella pneumoniae*).

Particular examples of infectious diseases caused by a virus include, but are not limited to, cytomegalovirus (CMV) pneumonia, enteritis and retinitis; Epstein-Barr virus (EBV) lymphoproliferative disease; chicken pox/shingles (caused by Varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); cervical cancer (caused by human papillomavirus); and hepatitis A, B or C.

Particular examples of infectious diseases caused by a protozoa include, but are not limited to, malaria (caused by *Plasmodium falciparum*); trypanosoma and Chagas' disease (caused by *Trypanosoma cruzi*), toxoplasma; leishmaniasisa and kalaazar (caused by *Leishmania*); giardiasis (caused by *Giardia*); *Cryptosporidium*; balantidiasis (caused by *Balantidium coli*); strongyloidiasis (caused by *Strongyloides stercoralis*); roundworms such as *Trichuris*, hookworm, and Strongyloides; and capillariasis (caused by *Capillariasis*).

Particular examples of infectious diseases caused by a fungus include, but are not limited to, thrush (caused by *Candida albicans*); cryptococcemia (caused by *Cryptococcus*); histoplasmosis (caused by *Histoplasma*), and aspergillosis (caused by *Aspergillus* spp.).

APCs

APCs are cells that present surface antigens bound to MHC class I or class II molecules to T cells. APCs include, but are not limited to, monocytes, macrophages, dendritic cells (DC), B cells, and Langerhans cells. In a particular example, APCs are DC. Methods of obtaining or generating APCs from a subject are known in the art. In one example, APCs are obtained from a blood sample from a mammal. For example, monocytes obtained from blood sample can be cultured to generate DC.

In particular examples, APCs (or precursors thereof) are obtained from the subject in whom an immune response is to be stimulated prior to administering an immunogenic composition. For example, the method can include isolating peripheral blood mononuclear cells (PBMCs) from the subject, wherein the PBMCs are used to obtain or generate APCs. In particular examples, DRibbles isolated from a cell (such as a tumor cell or a cell infected with a pathogen) contacted with an amount of a proteasome inhibitor sufficient to inhibit proteasome activity are incubated with APCs under conditions sufficient for the APC to present one or more DRiPs, thereby generating DRibble-loaded APCs. DRibble-loaded APCs can be administered to a subject (such as a subject having a tumor or infection), thereby stimulating an immune response against one or more DRiPs. Alternatively, the treated cells or isolated DRibbles from the treated cells can be administered to the subject (thus allowing the cells or DRibbles to contact the APCs in vivo), thereby stimulating an immune response against one or more DRiPs.

Administration

Any mode of administration can be used for administering a therapeutic agent, such as a proteasome inhibitor, autophagy inducer, treated cells, isolated DRibbles, DRibble-loaded APCs, and other compositions (such as lymphodepletion agents) disclosed herein. Proteasome inhibitors, autophagy inducers, treated cells, isolated DRibbles, DRibble-loaded APCs, and other compositions are administered to a subject in therapeutically effective amounts. Those skilled in the art, such as a treating physician, can determine an appropriate route of administration. In one example, administration of an immunogenic composition is subcutaneous or intradermal. In another example administration of a lymphodepletion agent is intravenous.

Proteasome inhibitors, autophagy inducers, as well as the disclosed treated cells, isolated DRibbles and DRibble-loaded APCs, are administered to a subject in a therapeutically effective amount. In particular examples, a therapeutically effective amount of proteasome inhibitor, autophagy inducers, treated cells, isolated DRibbles or DRibble-loaded APCs (or combinations thereof), is administered in a single unit dose. In another example, a therapeutically effective amount of proteasome inhibitor, autophagy inducers, treated cells, isolated DRibbles or DRibble-loaded APCs is administered in at least two unit doses, such as at least three unit doses, four unit doses, or five unit doses, over a period of at least 60 days, at least 90 days, at least 180 days, or at least 365 days.

Methods of Producing DRibbles

The present disclosure provides methods for producing DRibbles. Such methods can be used to stimulate, and in some examples enhance, production of DRibbles by a cell. DRibbles can be produced from any type of cell that produces DRiPs or SLiPs, such as mammalian cells. Examples of such cells include, but are not limited to, tumor cells and cells infected with one or more pathogens.

In particular examples, the method includes contacting (such as incubating) the target cell with a sufficient amount of a proteasome inhibitor under conditions sufficient for producing DRibbles, such as conditions that substantially inhibit protein degradation in the cell. For example, the cell can be contacted with the proteasome inhibitor for at least 4 hours, at least 6 hours, at least 12 hours, at least 18 hours, or at least 24 hours, such as 4-24 hours, 6-24 hours, 12-24 hours, or 12-18 hours. In some examples, the method further includes contacting (such as incubating) the target cell with a sufficient amount of an autophagy inducer under conditions sufficient for inducing autophagy of the cell. For example, the cell can be contacted with the autophagy inducer before, during, or after the proteasome inhibitor. In a specific example, the cell can be contacted with the proteasome inhibitor for at least 4 hours (such as at least 6 hours or at least 24 hours) followed by contact with the autophagy inducer for at least 4 hours, such as at least 12 hours or at least 18 hours.

The cell can also be contacted with other agents, such as sufficient amounts of both a proteasome inhibitor and one or more agents that decrease glycoslation of proteins (for example nucleoside translocase I inhibitors such as mureidomycin, tunicamycin, liposidomycin, or combinations thereof), under conditions sufficient to stimulate or even enhance production of DRibbles by the cell. In one example, the cell is contacted with sufficient amounts of a proteasome inhibitor (such as at least 20 nM Velcade), an autophagy inducer (such as rapamycin or HBSS) and $NH_4Cl$ under conditions sufficient to stimulate or even enhance production of DRibbles by the cell.

DRibbles can be produced in vivo, ex vivo, or by a combination of both in vivo and ex vivo methods. For example, DRibbles can be produced in vivo by administration of a therapeutically effective amount of one or more proteasome inhibitors (alone or in combination with other agents, such as an autophagy inducer or tunicamycin) to a subject, for example in an amount sufficient for producing DRibbles (such as an amount that substantially inhibits protein degradation in a tumor cell or a cell infected with a pathogen). As described above, the amount of proteasome inhibitor administered is in particular examples a dose that does not significantly induce apoptosis of a cell, such as a tumor cell. In another example, DRibbles are produced ex vivo by incubating a sufficient amount of one or more proteasome inhibitors (alone or in combination with other agents, such as an autophagy inducer or tunicamycin) with cells growing in culture, for example in an amount sufficient for producing DRibbles (such as an amount that substantially inhibits protein degradation in the cell).

In some examples, the method further includes harvesting the DRibbles produced by the cell. For example, DRibbles produced by a cell can be separated from the cells and then collected. In particular examples, separation of DRibbles from cell and cell debris results in a population of isolated DRibbles, such as a population that is at least 50% pure, such as at least 90% pure, at least 95% pure, or at least 99% pure.

One particular exemplary method of producing a purified population of DRibbles ex vivo includes contacting a cell with a sufficient amount of a composition that includes a proteasome inhibitor under conditions sufficient to substantially inhibit protein degradation in the cell, such as an incubation of about 6-24 hours. The cells are subsequently incubated under conditions sufficient to induce autophagy in the cell, such as an incubation of about 6-24 hours with an autophagy inducer. The resulting cells and DRibbles are centrifuged under conditions that pellet the cells but not the DRibbles. The supernatant containing the DRibbles is centrifuged under conditions sufficient to pellet the DRibbles. The resulting pellet containing a purified population of DRibbles is collected. The DRibbles can be used immediately, or cryopreserved for later use.

DRibbles from Tumor Cells

In one example, DRibbles are produced by tumor cells, such as cells from a hematological or solid tumor. Such DRibbles can be used to stimulate an immune response against the tumor, directly or indirectly (see below). In one example, tumor-derived DRibbles are produced in vivo, thereby stimulating an immune response against the tumor in the subject. In another example, tumor-derived DRibbles are produced ex vivo, and the tumor-derived DRibbles administered directly to a subject, or used to load APCs that are administered to a subject, thereby stimulating an immune response against the tumor in the subject. In some examples the DRibbles are not isolated, but instead a whole tumor cells that have been treated with the proteasome inhibitor (and in some examples also an autophagy inducer) and are thus producing DRibbles is administered to the subject as an immunogenic composition, wherein the number of cells administered is sufficient to induce an immune response, and in some examples cause regression of a tumor in the subject.

In a particular example, the cell is a mammalian tumor cell, such as a mammalian cancer cell. In a specific example, the cell is a human cancer cell. In some examples, a tumor cell is obtained from the subject to be treated, and DRibbles generated from these cells ex vivo. Tumor cells can be obtained from a subject using methods known in the art, such as from a surgically extracted tumor, or from a biopsy sample (such as a needle aspirate of the tumor). For example, tumor cells can be obtained from the subject and grown as a primary culture using tissue culture methods known in the art. Ideally, primary tumor cells can grow and expand well in culture, or the tumor sample obtained is large such that sufficient numbers of cells (such as at least 1 million cells) can be used for DRibble generation. Examples of tumors that grow well in culture, or tend to produce large-sized tumors having numerous cells, such that primary cultures can be used, include, but are not limited to leukemia, lymphoma, melanomas, lung cancers, ovarian cancer, gastric and colon carcinoma, and renal cell carcinomas.

However, some primary tumor cells are difficult to grow or expand in culture. In such examples, an established cell line for the same type of tumor as is present in the subject can be used, or DRibbles can be produced in vivo. Examples of tumors, whose cells are difficult to grow in culture, include but are not limited to: breast and prostate cancers. For example, if the subject has a breast cancer with cells that do not grow well in culture, DRibbles can be generated from a breast cancer cell line established from another subject. Examples of such cell lines are known in the art, such as MDA-MB-231 for breast cancer (see Example 22 below) and PC3 and LNCap for prostate cancer.

DRibbles from Infected Cells

In another example, DRibbles are produced from a mammalian cell infected with one or more pathogens, or a cell infected with vector (such as a plasmid or viral vector) that includes a nucleic acid molecule encoding a pathogenic antigen. Such DRibbles can be used to stimulate an immune response against the pathogen, directly or indirectly (see below). In one example, DRibbles obtained from infected cells are produced in vivo, thereby stimulating an immune response against the pathogen in the subject. In another example, DRibbles obtained from infected cells are produced ex vivo, and the DRibbles administered directly to a subject, or can be used to load APCs that are administered to a subject, thereby stimulating an immune response against the pathogen in the subject. In some examples the DRibbles are not isolated, but instead a whole pathogen-infected cells that have been treated with a proteasome inhibitor (and in some examples also an autophagy inducer) and are thus producing DRibbles is administered to the subject as an immunogenic composition, wherein the number of cells administered is sufficient to induce an immune response, and in some examples treat an infection in the subject or provide prophylactic protection against the pathogen.

Exemplary pathogens include, but are not limited to: viruses, bacteria, fungi, protozoa, and combinations thereof. For example, viruses include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polio viruses); Rhinoviridae (Rhinoviruses)); Hepativiridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); and Coronaviruses (examples of which include SARS coronaviruses, such as the Urbani strain). Exemplary negative-strand RNA viruses include, but are not limited to: Orthomyxyoviruses (such as the influenza virus), Rhabdoviruses (such as Rabies virus), and Paramyxoviruses (examples of which include measles virus and respiratory syncytial virus).

Viruses also include DNA viruses. DNA viruses include, but are not limited to: Herpesviruses (such as Varicella-zoster virus, for example the Oka strain; cytomegalovirus; and Herpes simplex virus (HSV) types 1 and 2).

Another group of viruses includes Retroviruses. Examples of retroviruses include, but are not limited to: human immunodeficiency virus type 1 (HIV-1), such as subtype C, HIV-2; equine infectious anemia virus; feline immunodeficiency virus (FIV); feline leukemia viruses (FeLV); simian immunodeficiency virus (SIV); and avian sarcoma virus.

Another type of pathogen is bacteria. Bacteria can be classified as gram-negative or gram-positive. Exemplary gram-negative bacteria include, but are not limited to: *Escherichia coli* (K-12 and O157:H7) and *Shigella dysenteriae*. Exemplary gram-positive bacteria include, but are not limited to: *Bacillus anthracis, Staphylococcus aureus*, pneumococcus, gonococcus, *Streptococcal meningitis*, and *Mycobacterium tuberculosis*.

Protozoa and fungi are also types of pathogens. Exemplary protozoa include, but are not limited to, *Plasmodium, Leishmania, Acanthamoeba, Giardia, Entamoeba, Cryptosporidium, Isospora, Balantidium, Trichomonas, Trypanosoma, Naegleria*, and *Toxoplasma*. Exemplary fungi include, but are not limited to, *Candida albicans, Cryptococcus, Coccidiodes immitis*, and *Blastomyces dermatitidis*.

To produce infected-cell-derived DRibbles ex vivo, pathogens can be used to infect cells (for example in vitro), and the infected cells used to produce DRibbles. The particular cell type infected can depend on the pathogen used. Methods of infecting cells with particular pathogens are known. Generally, methods include incubating a cell capable of infection by the pathogen, under conditions sufficient for the pathogen to infect the cell. In particular examples, pathogens are incubated with cells at 37° C. in culture medium for at least 30 minutes, such as at least 60 minutes. Pathogens that did not infect the cells can be removed by washing the cells. Although particular examples are provided herein, one skilled in the art will appreciate that other combinations of cells and pathogens can be used.

In one example, *Mycobacterium tuberculosis* bacteria can be used to infect macrophages (such as macrophages obtained from PBMCs), for example using the methods described in (Li et al., *Infect. Immun.* 70:6223-30, 2002). In another example *Plasmodium* protozoa (such *Plasmodium falciparum*) are used to infect erythrocytes or hepatocytes. In another example *Histoplasma* or *Cryptococcus* fungi are used to infect megakaryocytes. In another example, HIV is used to infect epithelial cells or lymphocytes.

The infected cells are then be incubated with a sufficient amount of proteasome inhibitor (alone or in the presence of other agents, such as an autophagy inducer or tunicamycin), for example under conditions sufficient to substantially inhibit protein degradation, thereby permitting the cell to generate DRibbles.

Proteasome Inhibitors

Proteasome inhibitors are known in the art, and include those which are reversible or irreversible. Particular examples of proteasome inhibitors include, but are not limited to, MG132, ALLN, and PS341 (Velcade®). Such inhibitors are used at concentrations and under conditions that substantially inhibit protein degradation in the cells, such as inhibit such degradation by at least 90%, thereby permitting formation of DRibbles by the cells. In particular examples, proteasome inhibitors are used at a sub-lethal dose, such as concentrations that do not significantly induce apoptosis of cells, such as do not induce apoptosis in more than 10% of the cells, for example as compared to an amount of apoptosis in the absence of the proteasome inhibitor. For example, this is in contrast to amounts of proteasome inhibitors currently administered to subjects having a tumor, wherein the proteasome inhibitor is administered to cause apoptosis of the tumor cells. In contrast, the concentrations of proteasome inhibitors used in the present application are lower than these amounts, such that the tumor cells produce DRibbles, and can be subsequently killed by tumor-specific T cells.

In a particular example, DRibbles are generated by contacting cells with one or more proteasome inhibitors for at least 6 hours (such as at least 8 hours, at least 12 hours, or even at least 16 hours, for example overnight treatment). Appropriate concentrations and incubation conditions can be determined using known methods by those skilled in the art.

Autophagy Inducers

Autophagy inducers are known in the art. Particular examples of autophagy inducers include, but are not limited to, nutrient deprivation of cells (for example by incubation in HBSS), incubation of cells under ischemic conditions, tamoxifen, rapamycin (such as 1 nM-100 nM), vinblastine (such as 5-100 mg/kg body weight vinblastine sulfate, for example 50 mg/kg body weight vinblastine sulfate), and IFN-γ (such as 10-1000 U/ml). Such inducers are used at concentrations and under conditions that substantially induce autophagy in the cells, thereby permitting formation of autophagy bodies by the cells. Methods of determining whether autophagy has been induced are known in the art, and particular methods are provided herein (for example see Examples 2 and 6).

In a particular example, DRibbles are generated by contacting cells with one or more proteasome inhibitors for at least 6 hours (such as at least 48 hours), followed by contacting the cell with one or more autophagy inducers for at least 6 hours (such as at least 18 hours). Appropriate concentrations and incubation conditions can be determined using known methods by those skilled in the art.

Harvesting DRibbles

Harvesting DRibbles can include separating DRibbles from the cells, for example by collecting secreted DRibbles, by lysing cells and collecting intracellular DRibbles, or combinations thereof.

For example, DRibbles secreted by the cell into the cell culture medium can be isolated. In one example, centrifugation is used. For example, cells and the culture medium are centrifuged under conditions sufficient to pellet whole cells and large cell debris, but not the DRibbles (for example by low-speed centrifugation). The pellet of whole cells can be used to obtain intracellular DRibbles (see below). The resulting supernatant containing DRibbles is centrifuged under conditions sufficient to pellet the DRibbles (such as high-speed centrifugation).

In one example the DRibble pellet obtained using low- and high-speed centrifugation described above is further purified by ultracentrifugation in a Percoll colloidal density gradient. For example, the pellet can be layered on top of a discontinuous gradient of 21 ml of 33% Percoll in PBS on top of 7 ml of 22.5% Nycodenz in PBS (1.127 g/ml), and centrifuged for 30 minutes at 72,000 g in a SW28 rotor. Autophagy bodies will be banded at the lower interface, while apoptotic bodies or release mitochondria will be pelleted on the bottom of tube. Other light membranes, such ER and debris of plasma membrane, will be banded in the upper interface. It is expected that DRibbles are autophagy bodies.

Intracellular DRibbles can also be obtained, for example by lysing the cell and substantially separating the DRibbles from other cell debris.

In particular examples, the resulting substantially isolated population of DRibbles are at least 70% pure, such as at least 80% pure, at least 90% pure, at least 95% pure, or even at least 99% pure. DRibbles can be used immediately, or cryopreserved (for example at −20° C. or at −80° C.) until use. In one example, isolated DRibbles are preserved in the presence of DMSO.

Isolated DRibbles

The present disclosure also provides isolated DRibbles generated using the disclosed methods. In particular examples an isolated population of DRibbles is substantially purified, such as at least 70% pure, at least 80% pure, at least 90% pure, or even at least 95% pure. Such DRibbles can be an immunogenic composition. In one example, an isolated population of DRibbles is frozen, for example in the presence of at least 10% DMSO.

Isolated DRibbles can be part of a kit. For example, a kit can include one or more containers of DRibbles obtained from tumor cells, and well as one or more other containers that include one or more chemotherapeutic or lymphodepletion agents such as fludarabine, cyclophosphamide, or combinations thereof.

In one example, the kit includes isolated DRibbles and an agent that inhibits tumor or stromal cell inhibitory molecules such as PD-1. For example, such a kit could include isolated DRibbles and antibodies or siRNAs that recognize one or more of PD-1, PD-1L1, or PDl-L2.

Immunogenic Compositions

Immunogenic compositions and methods of producing such compositions are provided by the present application. Immunogenic compositions are those that can stimulate or elicit an immune response by a subject's immune system, such as stimulating the production of a T-cell response in the subject, for example a T-cell response against a TAA or a pathogen-associated antigen (such as a VAA). Exemplary immunogenic compositions include vaccines. In one example, an immunogenic composition includes tumor or pathogen infected cells treated with an amount of a proteasome inhibitor sufficient to stimulate DRibble production by the cell, isolated DRibbles, DRibble-loaded APCs, or combinations thereof.

The disclosed immunogenic compositions can include other agents, such as one or more pharmaceutically acceptable carriers, immunostimulants (such as an adjuvant), anti-neoplastic chemotherapeutic agents, or combinations thereof. Adjuvants include agents that can augment the resultant immune response. Adjuvants are known in the art, and particular examples include, but are not limited to Freund's Incomplete Adjuvant (IFA), Freund's complete adjuvant, bacterial toxins, and nucleic acid molecules. One particular example of an immunostimulant is a cytokine, such as GM-CSF. In one particular example, the adjuvant is an ssRNA, such as an ssRNA single strand oligoribonucleotides.

In one example, an immunogenic composition is generated by producing a population of treated cells using the methods described herein (for example incubation with a proteasome inhibitor and an autophagy inducer), and then preparing a composition that includes the treated cells.

In one example, an immunogenic composition is generated by producing a population of isolated DRibbles using the methods described herein, and then preparing a composition that includes the isolated DRibbles.

In one example, methods of generating an immunogenic composition include contacting a population of isolated DRibbles with an APC, thereby generating an immunogenic composition that includes DRibble-loaded APCs. In particular examples, the DRibble-loaded APCs are isolated from the DRibbles, for example by washing the loaded APCs, and the isolated DRibble-loaded APCs form an immunogenic composition.

EXAMPLE 1

Preparation of DRibbles Using Proteasome Inhibitor

This example describes methods used to stimulate production of DRibbles from tumor cells. One skilled in the art will appreciate that other tumor cells can be used, such as a tumor cell obtained from a subject having a solid or liquid tumor. Similarly, other proteasome inhibitors can be used, such as incubation with 20-1000 nM Velcade for 6 to 48 hours. One skilled in the art will also appreciate that similar methods can be used to produce DRibbles from cells infected with one or more target pathogens, such as HIV.

Female C57BL/6 (H-$2^b$) mice (Jackson Laboratory, ME) aged 8-12 weeks were used. B16F10 and 3LL are spontaneous mouse melanoma and lewis lung carcinoma cell lines from female C57BL/6 mice, respectively. RM1 is a mouse prostate carcinoma derived from embryonic prostate epithelium. RM1-Ova is a RM1 cell line that expressing ovalbumin by stable transfection with a plasmid encoding ovalbumin.

Tumor cell lines were cultured on plastic in complete medium (CM), RPMI 1640 (BioWhittaker, Walkersville, Md.) supplemented with 0.1 mM nonessential amino acids, 1 mM sodium pyruvate, 2 mM L-glutamine, 50 µg/ml gentamicin sulfate, and µM 2-ME (Aldrich, Milwaukee, Wis.) and 10% FBS (Life Technologies, Grand Island, N.Y.). Tumor cells were harvested two to three times per week by trypsinization and maintained in T-150 culture flasks.

To prepare tumor-derived DRibbles, one T-150 flask of cultured tumor cells at about 80% confluence (about 30 million cells per flask) were treated for 24 hours with reversible proteasome inhibitor MG132 (5 µg/ml) or ALLN (5 µg/ml) to block proteasome-mediated degradation of ubiquitinated proteins. As shown in FIG. 1A, incubation of tumor cells in the presence of ALLN induced formation of prenuclear vacuoles and secretion of DRiPs containing blebs (DRibbles). Culture supernatant was collected in a 50 ml conical tube 48 hours later, and whole tumor cells and large cell debris removed by a low speed centrifugation (250 g for 10 minutes) (FIG. 1B). The resulting supernatant was further centrifuged at a high speed (10,000 g for 15 minutes) to pellet DRibbles. The pellets (containing the DRibbles, see FIG. 1C) were washed once by re-suspending in PBS (20 ml) and pelleting at high speed as above. The washed pellets were resuspended in 300 µl PBS (10 µl DRibble=1 million cells) and snap frozen in liquid nitrogen and kept at −80° C. in small aliquots until use.

A combination of MG-132 (5 µg/ml) and tunicamycin (5 µg/ml) significantly increased DRibble production (FIG. 1G), as compared to either MG-132 (FIG. 1E) or tunicamycin (FIG. 1F) alone, or no treatment (FIG. 1D). 3LL tumor cells were treated as described above, except that in some examples tunicamycin (5 µg/ml) alone or in combination with MG-132 was incubated with the tumor cells.

The size of DRibbles was determined using the Malvern Zetasizer Nano instrument (Particle Technology Lab, Ltd., Downers Grove, Ill.). Based on the intensity-weighted distribution, the average size of DRibbles was about 230 nM, significantly larger than exosomes (70 nM). This indicates that DRibbles are not exosomes.

EXAMPLE 2

Proteasome Inhibitors Induce Autophagy

This example describes methods of used to demonstrate that incubation of tumor cells in the presence of a proteasome inhibitor results in autophagy.

The autophagy inhibitor 3-methyladenosine (3-MA) and the autophagy inducer rapamycin were used to modulate autophagy and observe their effect on human 293T tumor cells expressing V-GFP-TfR-OVA fusion (a peptide containing mutated ubiquitin, GFP (green fluorescent protein), the transmembrane domain of transferrin receptor and chicken ovalbumin). In addition 10 mM $NH_4Cl$ was used to inhibit lysosome mediated protein degradation. Cells expressing V-GFP-TfR-OVA were either untreated, treated with 10 mM 3-MA for 24 hours, treated with 10 mM 3-MA and 1 µM Velcade for 24 hours, 50 nM rapamycin for 24 hours, 50 nM rapamycin and 1 µM Velcade for 24 hours, 10 mM $NH_4Cl$ for 24 hours, or with 1 µM Velcade and 10 mM $NH_4Cl$ for 24 hours. Cell lysates were prepared by resuspending pelleted cells in SDS containing sample lysis buffer and subjected to western blot analysis with anti-GFP antibody.

Compared to untreated control cells, both full-length and short fragments of fusion proteins were increased by 3-MA treatment, and combination of both 3-MA and Velcade resulted in greater effect on the stabilizing of short fragments. Thus, both the proteasome and autophagy are involved in the degradation of DRiPs and SLiPs. Velcade treatment slightly increased the amount of short fragments in the presence of rapamycin, indicating most DRiPs are likely degraded by autophagy in the absence of functional proteasomes. An even greater stabilizing effect of shorter fragments was induced by $NH_4Cl$ and $NH_4Cl$ plus Velcade, indicating that autophagy and the proteasome degrade DRiPs. However, it was unexpected that Velcade together $NH_4Cl$ failed to rescue rapamycin-induced degradation of both full-length proteins and DRiPs. As shown in the Examples below, the degradation products of intact proteins and DRiPs found in DRibbles are the more efficient substrate for cross-presentation even though intact proteins or DRiPs could also serve as the substrates. Therefore, it appears that autophagy results in the accumulation of DRiPs and the pre-digestion of DRiPs into smaller fragments, permitting presentation to APCs.

To confirm whether Velcade induced autophagy, Western blot analysis of LC-3 was performed. LC3 is an autophagy marker; it converts from its LC3-I-nonlipidated form to the PE-conjugated form LC3-II. 293T were treated with 1 µM Velcade overnight and total cell lysates were subjected to Western blot analysis with anti-LC3 polyclonal antibody. While only the LC3-I form was detected from control cells, proteasome inhibition resulted in both increase of LC3-I and newly generated LC3-II, demonstrating that Velcade induced autophagy in 293T cells.

These results demonstrate that inhibition of proteasome function induces accumulation of DRiPs and activity of cell autophagy.

EXAMPLE 3

Inhibiting Proteasome Function Increases Cross-Presentation of Short-Lived Proteins This example describes methods used to demonstrate that blocking degradation of short-lived OVA resulted in increased cross-presentation in vivo. In the presence of native degradation mechanisms, long-lived but not short-lived proteins were efficiently cross-presented in vivo.

Cell lines that expressed either long-lived or short-lived forms of OVA that were capable of stimulating B3Z OVA-specific hybridoma cells, were used to determine whether they could cross-present ovalbumin (OVA) to naive OT-I Tg T cells. A ubiquitin-like molecule, Sumo was fused with N-terminal truncated OVA (41-386). The constructs contain the dominant CD4 and CD8 epitopes and their presentation was monitored by OT-II and OT-I TCR Tg T cells. The cDNA coding the fusion proteins (Sumo-M-OVA and Sumo-R-OVA, where M-OVA has a half-live of at least 4 hours and R-OVA has a half-live of less than 10 minutes) was cloned into the bicistronic lentiviral vector pWPI and transfected into 293T cells to generate lentiviral supernatants. The GFP expression is under control of IRES in the same expression cassette as the Sumo-X-OVA fusion proteins. OVA expression in 293T cells transfected with Sumo-R-OVA is approximately ten-fold lower than in Sumo-M-OVA transfected cells. Viral supernatant was used to transduce B16F10 and B78H1 melanoma cells. More than 70% of tumor cells were transduced as judged by GFP expression.

Five million naive spleen cells from OT-I mice were labeled with CFSE before adoptive transfer into B6 mice followed by inoculation of 1×10$^6$ live tumor cells (F10 or B78H1 cells) transduced with either the Sumo-M-OVA or Sumo-R-OVA lentiviral vector. MG-132 (5 µM) was added to tumor cells for 24 hours before irradiation to block proteasome activity and degradation of R-OVA. Ten days post tumor injection, spleens were harvested and CFSE fluorescence on gated CD8$^+$ T cells was determined by flow cytometry.

As shown in FIG. 2A, vector alone transduced tumor cells (both F10 and B78H1) failed to induce CFSE dilution. Sumo-M-OVA transduced tumor cells of both types caused significant proliferation of OT-I T cells. The response to Sumo-R-OVA was different for the different tumor cells, likely due to the different half-life of R-OVA in F10 and B78H1 tumor cells as seen for R-GFP. As shown in FIG. 2B (far right panel), blocking proteasome function of F10-Sumo-R-OVA cells resulted in dramatic increase the efficiency of cross-presentation of OVA.

These results demonstrate that the half-life of protein antigens is important for cross-presentation but not direct presentation of tumor antigens. Therefore, inhibiting proteasome function in cells (such as tumor cells or cells infected with a target pathogen) can prevent degradation of short-lived proteins (such as DRiPs and SLiPs) and lead to their efficient cross-presentation.

EXAMPLE 4

Inhibiting Proteasome Function of RMA Tumor Cells Increases Cross-Presentation of Gag-Specific T Cells In Vivo This example describes methods used to demonstrate that inhibition of proteasome function in RMA tumor cells can increase cross-presentation of the gag protein.

An example of the failure of cross-presentation of short-lived proteins is the gag of MuLV, a dominant antigen for retrovirally induced tumors (FBL-3, RMA, MBL-2, RBL-5). The dominant epitope is derived from the leader peptide of an alternative translated larger product of the gag gene (gPr75$^{gag}$) with unconventional CUG as the initiation codon for its translation. While FBL-3 or RMA-S/DC fusion cells induce tumor-specific T-cell immunity, TAP-deficient RMA cells (RMA-S) fail to do so. Initiation at CUG results in Leu as the N-terminal amino acid of gPr75$^{gag}$ protein. Leu is a type 1 primary destabilizing residue and is subject to rapid degradation mediated by ubiquitin-proteasome pathway after their synthesis.

To demonstrate that gag-specific T cells could be primed when degradation of gPr75$^{gag}$ was blocked, RMA tumor cells (10 million) were injected into mice with or without treatment with proteasome inhibitor, 5 µM MG 132 for 24 hours. Seven days later, spleen cells were restimulated with either irrelevant D$^b$ binding peptide or the dominant epitope of gag in the presence of blocker of ER/Golgi (brefeldin A) for 6 hours. The percentage of CD8 T cells produced intracellular IFN-γ was then determined by intracellular staining and flow cytometry analysis with antibodies against CD3, CD8, and IFN-γ.

Without proteasome inhibitor treatment, CD8 T cells from RMA immunized mice produced only background level of IFN-γ (0.44%), whereas treatment with MG 132 induced a significantly higher percentage of IFN-γ-producing cells (1.74%) over the background (0.29%).

Therefore, inhibiting proteasome function of tumor cells (or cells infected with a target pathogen) can reduce or prevent degradation of short-lived proteins (such as DRiPs and SLiPs) thereby promoting their efficient cross-presentation in vivo.

EXAMPLE 5

Role of Autophagy in Cross-Presentation

This example describes methods used to demonstrate the role of autophagy in cross-presentation.

293T tumor cells expressing V-GFP-TfR-OVA were treated as described in Example 2, and used as the source of antigens for cross-presentation in vitro after irradiation (15,000 rad). One million tumor cells were incubated with two million DC for 6 hours before the addition of CFSE labeled naïve T cells from OT-I transgenic mice that recognize peptides derived from OVA protein. The OT-I division as indicated by dilution of CFSE label was used as the readout.

As shown in FIG. 3, cross-presentation was severely curtailed by 3-MA treatment of tumor cells whether or not Velcade was included to accumulate more DRiPs. In contrast, the autophagy inducer rapamycin greatly increased the cross-presentation of tumor cells even though the antigen level detected by Western blot (Example 2) was much lower than that of untreated control cells. NH₄Cl increased protein level and induced a moderate increase of cross-presentation. Rapamycin in the presence of NH₄Cl induced highest level of cross-presentation while the antigen level was found to lowest.

These results indicate that autophagy activity of tumor cells (or a cell infected with a target pathogen) is involved for cross-presentation.

Therefore, DRiPs and SLiPs can be degraded by both proteasome and autophagy systems, and their cross-presentation can be increased by reducing proteasome activity and increasing autophagy.

EXAMPLE 6

DRibbles are Secretory Autophagy Bodies

This example describes methods used to demonstrate that DRibbles are autophagy bodies released from cells. As shown in the Examples above, incubation of cells with a proteasome inhibitor induces autophagy, and the size and morphology of DRibbles resembles autophagosomes found in cells undergo active autophagy.

293T tumor cells were transfected with plasmids encoding Ub-M-GFP-OVA, GFP-LC3 fusion protein, or GFP-LC3 and tdTomato-Ub proteins. Transfected cells were treated with 1 µM Velcade 24 hours later. GFP-OVA or GFP-LC3 fusion proteins were used to visualize the antigens or autophagy membrane in the DRibbles using fluorescence microscopy. Co-tranfection of GFP-LC3 and tdTomato-Ub fusion plasmids was used to visualize accumulation of ubiquitinated DRiPs inside LC3 decorated DRibbles.

Velcade treatment led to formation of cell-associated punctate positive for GFP-OVA or GFP-LC3. Many of these punctate structures were either free particles or loosely attached to cells. When tdTomato-Ub (an orange variant of dsRED fluorescent protein) was used to tag ubiquitinated proteins, ubiquintinated proteins were found to encapsulate in GFP-LC3 positive vesicles. These results indicate that DRibbles are secretory autophagy bodies.

Characterization of DRibble proteins by Western blot analysis also indicates that DRibbles are secretory autophagy bodies that contain ubiquinated proteins. Lysates (10 µg) were prepared from DRibbles generated from 293T cell lines expressing different versions of GFP-OVA fusion proteins after Velcade treatment. The lysates were probed with antibodies against GFP, LC3, calrecticulin, HSP90α (cytosolic), and ubiquitin.

Velcade treatment resulted in large amount GFP-OVA fusion protein in the DRibbles). A greater amount of short fragments of fusion proteins was found in DRibbles generated from cells treated with Velcade. Other ubiquitinated proteins were also present as detected with anti-Ub antibody. Consistent with the notion that DRibbles are autophagy bodies, only processed LC3-II proteins were detected from lysates of DRibbles. In addition, HSP90α, HSP94 (Grp94), and calreticulin were detected in DRibbles.

In summary, prolonged inhibition of proteasome function and activation of autophagy result in the release of autophagy bodies (DRibbles), which contain intact proteins, DRiPs, HSP90, calreticulin, ubiqintinated proteins, and processed LC3-II.

EXAMPLE 7

Dendritic Cells Uptake DRibbles and Release Proinflammatory Cytokines

This example describes methods used to allow uptake of isolated DRibbles by DC, and the analysis of cytokines produced by such DC.

DC were generated by hydrodynamic injection of plasmid DNA encoding Flt3 ligand and GM-CSF. Mice were injected i.v. with 2 µg plasmid DNA encoding Flt3 ligand in 2 ml HBSS at day 1 and followed by i.v. injection of same amount of plasmid DNA encoding GM-CSF 10 days later. DC were harvested from spleens of injected mice on day 15. Typically, 30-50% of spleen cells were DC (CD11c and MHC II positive).

DRibbles were prepared from 293T cells using the methods described in Example 1. DRibbles (3 µl/ml) were incubated with 1×10⁶ DC cells for 2 hours. In some examples, 10 µg/ml of anti-CD40 antibody alone or in combination with IFN-γ (100 ng/ml) was incubated with the DC cells. The resulting DRibble-loaded DC were analyzed for cytokine secretion using ELISA.

Figure 4:
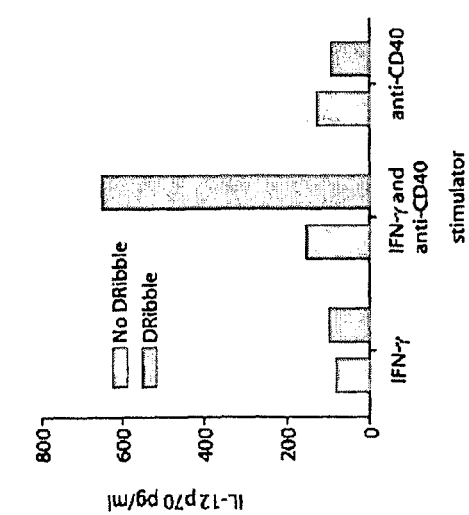
FIG. 4 is a bar graph showing that DRibble-loaded DC secrete IL-12 p70 in the presence of anti-CD40 and IFN-γ.

DRibbles stimulated DC to release IL-6 and IL-12 p40 (FIG. 4), but not IL-10 and IL-12 p70, in a dose-dependent fashion. IL-12 p70 was only produced by DRibble stimulated DC in the presence of both anti-CD40 antibody (10 µg/ml) and IFN-γ (100 ng/ml). The production of IFN-α and IL-12 p40 by DC after ingestion of tumor cells or vesicles/DRibbles derived from transfected tumor cells may represent an approach that mimics natural infections. Results of experiments also indicates that endocytosis of DRibbles by DC may utilize the calrecticulin/LRP interaction.

In summary, DRibbles activate DC to release proinflammatory cytokines and may be internalized by DC via scavenger receptors. The production of IL-12 p70 by DC can be modulated with anti-CD40 antibody and IFN-γ. In addition, agents that provide strong cognate help from TRP-1 TCR transgenic T cells or NKT cells with α-GalCer can be used to enhance cytokine production.

EXAMPLE 8

DRibbles Provide a Source of Antigen for Cross-Presentation

This example describes methods used to compare the ability of DRibbles and whole tumor cells to provide antigen for cross-presentation in vitro and in vivo.

DRibbles were generated by treating 293T cells expressing Sumo-M-OVA, gp100, or TRP-1 with 0.05 µM Velcade for 24 hours and loaded into DC using the methods described in Example 7. For comparison, the amount of DRibbles loaded is derived from the same number of tumor cells loaded onto DC. OVA and gp100 proteins, or TRP-1 peptide were used for the positive controls. DC alone (CM) and DRibbles generated from 293T cells expressing GFP vector were used as negative controls. After washing, DC were used to stimulate CFSE-labeled naïve T cells from OT-I and OT-II TCR Tg mice (for OVA models), pmel-1 (for gp100 model), or TRP-1 TCR Tg mice in vitro or in vivo after adoptive transfer. The CFSE profile of T cells was determined at day 5 (in vitro) and day 7 (in vivo).

As shown in FIG. 5A, DC loaded with DRibbles, but not irradiated whole tumor cells, induced significant CFSE dilution of OT-I, OT-II, pmel-1, and naive T cells. In addition, DRibbles from 293T cells transfected with TRP-1 plasmid DNA were able to promote proliferation of CD4 naive T cells from transgenic mice whose TCR are specific for TRP-1 melanoma antigen.

As shown in FIG. 5B, DC loaded with DRibbles generated from 293T cells transduced with GFP vector or culture with DRibbles alone without DC did not induce any CFSE dilution above the level observed in complete media control alone (CM), indicating DRibble-induced T-cell proliferation is antigens-specific.

To compare the relative efficiency of cross-presentation of OVA, tumor cells, and DRibbles in vivo, transgenic OT-I naive T cells were labeled with CFSE and adoptively transferred into B6 mice, mice were then vaccinated with DC loaded with OVA (10 µg/ml), tumor cells (3:1 tumor to DC), DRibbles prepared from 293T cells that express M-OVA (10 µl=$10^6$ cells=5 µg total protein). At day 7 post vaccination, the CFSE dilution indicated that DRibbles were at least as good as OVA, and better than tumor cells to induce division of naive OT-I T cells in vivo (FIG. 5B).

A titration was performed to compare the efficiency of DRibbles and purified OVA protein in the cross-presentation assay with both OT-I and pmel-I models. DC loaded with 1 µl/ml DRibbles, that equal to $10^5$ tumor cells or 0.5 µg/ml total proteins, was significantly better than 1 µg/ml purified OVA protein. The amount of OVA in whole lysate of transduced 293T cells was about 10 ng/$10^6$ cells. It is likely that the absolute amount OVA in DRibbles will not exceed 1 ng/µl DRibbles. Since 1 µl of DRibbles was better than 1 µg soluble OVA protein, DRibbles were at least 1000 fold more efficient than soluble OVA as the source of antigen for cross-presentation. In the gp100/pmel-1 system, 3 µl DRibbles (0.6 µg proteins in this DRibble preparation) were as good as 3 µg recombinant gp100 protein at promoting proliferation of naive pmel-1 T cells. DRibbles isolated from cells transfected with melanoma antigen were also found to be superior to whole tumor cells or recombinant protein to stimulate melanoma-specific T cells.

In summary, cross-presentation of DRibbles was more efficient than whole tumor cells or purified proteins to both CD4 and CD8 T cells.

EXAMPLE 9

Sensitization of T Cells using GM-CSF

This example describes methods of sensitizing naïve tumor-reactive T cells with DRibble-loaded DC, using the DRibbles generated in Example 1.

Bone marrow derived dendritic cells (DC) were prepared as follows. Bone marrow cells from C57BL/6 (H-$2^b$) mice were cultured in granulocyte-colony stimulating factor (GM-CSF) containing complete media according to a previously published protocol (*J. Exp. Med.* 176(6):1693-70, 1992). Briefly, a single cell suspension of bone marrow was made from femurs of mice and cultured at 1 million cells per ml of complete media containing 50 ng/ml recombinant murine GM-CSF (PeproTech) in Petri dishes for bacteria. On days 3 and 6, fresh GM-CSF supplemented media were added to the dishes, and nonadherent and loosely adherent cells that are usually more than 50% of $CD11c^+$ dendritic cells were harvested at day 9 and frozen in 10 million cells aliquots in liquid nitrogen until use. Generally DCs generated by this process will include both immature and mature DCs as judged by flow cytometry analysis for their expression of MHC II and costimulatory molecules (CD80 and CD86).

Naïve tumor-reactive T cells were sensitized with DRibble-loaded dendritic cells as follows. Frozen DCs were thawed and cultured at 2 million cells per ml of complete media (CM). DCs were loaded with DRibbles and activated at the same time by adding 10 µl/ml of DRibbles, 50 ng/ml GM-CSF, and 1 µg/ml of MPL (monophosphoryl lipid A, a nontoxic derivative of lipid A) for 6 hours. As a control, another group of DCs was also incubated with irradiated F10 tumor cells ($2\times10^6$ DC and $4\times10^6$ F10 cells) for 6 hours.

DC (2 million) were then washed and used to stimulate 20 million spleen cells from naïve mice in 10 ml CM in a culture tube in an up-right position for 2-3 days. Naïve spleen cells were stimulated with bone-marrow derived DC alone, or DC pre-incubated with F10 tumor cells, or with F10 tumor-derived DRibbles ($2\times10^6$ DC and 10 µg DRibbles, $4\times10^6$ F10 equivalent) for two days. The culture tube was then centrifuged and cells were washed once with HBSS. After washing, fresh CM with 10 ng/ml IL-7 and 5 ng/ml IL-15 were added to cells to expand the sensitized T cells in a horizontal position for another 3 to 6 days. Fresh media with same amount of IL-7 and IL-15 were added at day 3 if needed.

EXAMPLE 10

Sensitization of T Cells Using Flt3

This example describes a method that can be used to generate DC using Flt3 ligand. This method can be used as an alternative to the method described in Example 9.

DC are generated by hydrodynamic injection of plasmid DNA encoding Flt3 ligand and GM-CSF. A mammal is injected i.v. with 0.5-100 µg (such as 1-20 µg) plasmid DNA encoding Flt3 ligand in 2 ml HBSS at day 1 and followed by i.v. injection of same amount of plasmid DNA encoding GM-CSF 10 days later. DC can be harvested, for example from spleens of injected mammals on day 15.

DC generated with Flt3 ligands contain at least four major populations ($CD11b^+$ myeloid DC, $B220^+$ pDC, $CD8^+$ lymphoid DC, and an unknown triple negative DC). In an in vitro cross-presentation assay, DRibbles were cross-presented by all four different subsets of DC and all of them efficiently stimulated OT-I and OT-II responses.

To determine which subsets of DC responsible for cross-presentation in vivo, DiD labeled OVA-DRibbles can be injected i.d. into naive mice. Twenty four hours later, draining lymph nodes are harvested and subjected to multiple color flow cytometry analysis with antibodies against CD11c, CD11b, B220, CD8, F4/80, CD40, and CD80. A 9 color panel can be used to interrogate the different subsets of DC generated by Flt3 ligands using Dako CyAm flow cytometer. DiD positive DC can be also sorted and used to stimulate OT-I and OT-II T cells in vitro to confirm their cross-presentation ability after isolation. DC from mice injected with control 293T DRibbles can be used as the negative control.

EXAMPLE 11

Tumor-Specific Response of Dribble-Stimulated and Expanded T Cells

This example describes methods used to measure the tumor-specific response to DRibble-stimulated and expanded T cells. One skilled in the art will recognize that other methods of measuring IFN-γ can be used, and that other indicators of immune response can be measured.

Figure 7A:
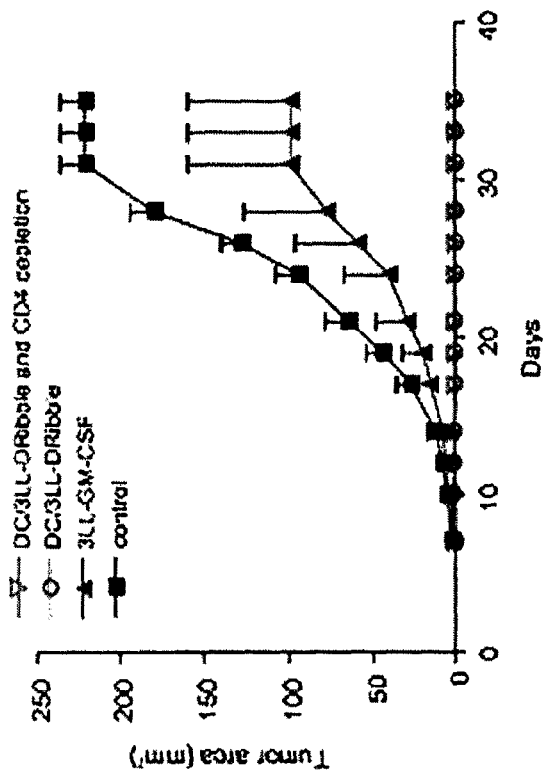
FIGS. 7A and 7B are bar graphs showing that DRibble-primed T cells are tumor-specific. Naive spleen cells were stimulated with DC-loaded with (A) F10-DRibble or (B) 3LL-DRibble and expanded with IL-7 and IL-15 for 5 days and resultant T cells restimulated with irradiated F10, 3LL or mouse prostate carcinoma cells (MPR4, MPR5, RM1 or RM1-OVA).

To measure tumor-specific production of IFN-γ, T cells ($2\times10^5$) that were stimulated and expanded with DRibble-loaded DC (see Example 9) were restimulated with irradiated tumor cells (3,000-30,000 cells) for 24 hours. Tumor cells included the F10 melanoma, Lewis lung tumor (3LL), MCA fibrosarcoma, or mouse prostate carcinoma cells (MPR4 and 3). In tests where multiple tumor cells were used, 104 tumor cells were used (FIGS. 7A and B). To induce MHC class II expression in F10 and 3LL cells, tumor cells were transfected with a plasmid or a retroviral vector containing a MHC class II transactivator (CIITA). T cells cultured alone with CM were used as the control. Restimulation was done in triplicate wells in a 96 well plate. For example, $10^5$ T cells were mixed with $10^4$ tumor cells in 200 µl of CM and cultured for 18 hours. The supernatants were collected and the levels of IFN-γ determined by ELISA (ebioscience, CA).

Figure 6:
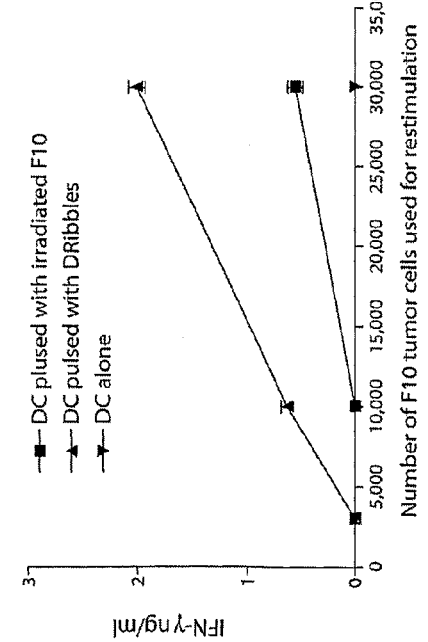
FIG. 6 is a graph showing a greater amount of IFN-γ production by tumor-specific cells restimulated with dendritic cells pulsed with DRibbles derived from tumor cells than with tumor cells themselves.

As shown in FIG. 6, DC loaded with melanoma DRibbles induce tumor CD8 T cells in vitro. Because the greatest T-cell activation was induced when DCs were incubated with DRibbles, compared to apoptotic bodies, exosomes, and freeze thaw lysate of tumor cells, this indicates that DRibbles contain the precursors for cross-presentation.

Figure 7B:
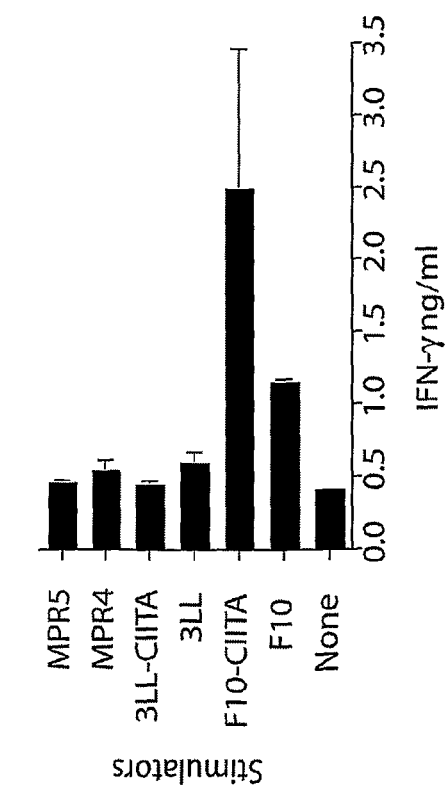

As shown in FIGS. 7A and B, this effect was tumor-specific as strong production of IFN-γ was observed in the presence of F10 cells when DRibble derived from F10 tumor cells was used for T-cell stimulation, but not for other tumor cells (FIG. 7A). Conversely, DRibble derived from 3LL tumor cells only stimulated and expanded 3LL-specific T cells (FIG. 7B).

EXAMPLE 12

Tumor Regression after Administration of DRibble-Loaded Dendritic Cells

This example describes methods used to show the in vivo effects of administration of DRibble-loaded DC to a mammal having a tumor. One skilled in the art will appreciate that similar methods can be used for other tumors, or to treat other mammals. In addition, similar methods can be used to administer DRibbles instead of DRibble-loaded DC to a mammal.

To demonstrate the therapeutic efficacy of vaccination with DRibble-loaded dendritic cells, a subcutaneous tumor model was used. Naive C57BL6 mice injected with $4\times10^5$ cultured 3LL tumor cells subcutaneously (s.c.) near the mammary glands were divided into four groups (5 mice per group). Control mice received 5 mg/kg docetaxel i.p. at day 3; the second group of mice were treated docetaxel at day 3 (5 mg/kg i.p) and s.c. administration of irradiated 3LL tumor cells that produce mouse GM-CSF ($2\times10^6$ cells, 1 µg GM-CSF/$10^6$ cells/24 hour) on day 5; the third group received docetaxel on day 3 (5 mg/kg i.p) and $2\times10^6$ dendritic cells loaded with DRibbles derived from $2\times10^6$ 3LL tumor cells activated with 1 µg/mL MPL for 6 hours were injected s.c. on both flanks (one million per site) on day 5; the fourth group received the same vaccine as group 3 and additional anti-CD4 depletion GM-CSF-producing antibody on day 5.

At the dose of 3LL cells injected, tumors were usually palpable at 5-7 days post inoculation. Tumor growth was measured with digital calipers every two or three days. Tumor area was calculated by multiplying the largest tumor dimension with the smallest dimension.

Figure 8A:
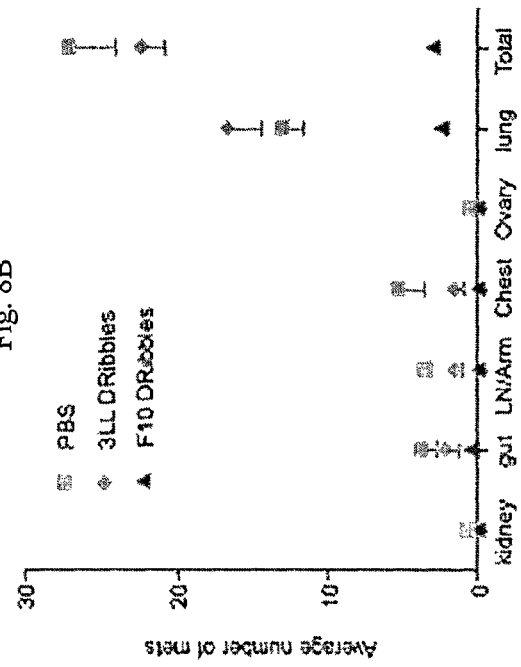
FIG. 8A is a graph showing complete regression of 3-day tumors induced by administration of dendritic cells (DC) loaded with DRibbles.

As shown in FIG. 8A, DC loaded with 3LL-DRibble induced complete tumor regression with or without CD4 help, while the GM-CSF gene modified whole tumor cell vaccine exhibited significantly less efficacy (could only delay tumor growth). Surviving mice also resisted a second tumor challenge; CD8 T cells were found to be the main effector T cells that mediated the protection.

Figure 8B:
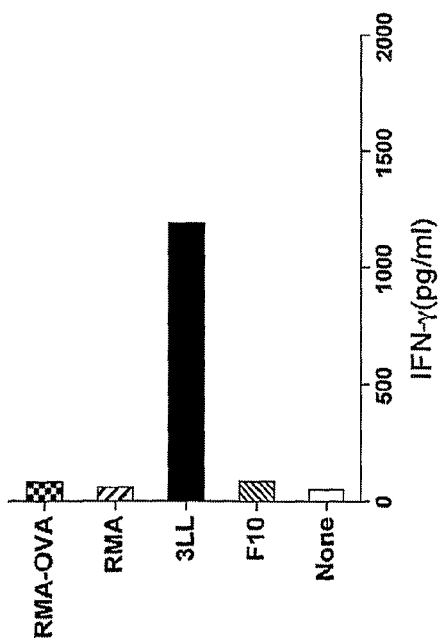
FIG. 8B is a graph showing reduction in metastasis of 4-day F10 melanoma tumors by administration of DC loaded with F10 DRibbles, but not 3LL DRibbles.

To demonstrate that the effect of the DRibbles is specific and can reduce metastasis of a tumor, mice bearing disseminated F10 melanoma were administered DC loaded with F10 DRibbles or 3LL DRibbles. C57B6 mice were administered $2\times10^5$ of F10 melanoma cells i.v. F10 melanoma cells disseminate throughout the body after i.v. injection. Metastases are found in kidney, gut, lymph nodes, chest wall, ovary, and lungs. Four days later, DC loaded with DRibbles ($2\times10^6$ DC cells) derived from F10 or 3LL were administered i.v. As shown in FIG. 8B, administration of F10 DRibbles, but not 3LL DRibbles, significantly reduced formation of metastases in these organs (the difference in lungs and total metastases was significant, p<0.05 by t-test). These data demonstrate that DRibble-induced responses are tumor-specific.

In summary, administration of DRibble-loaded DC can mediate tumor regression more efficiently than whole tumor vaccines. It is expected that administration of DRibbles (such as 10-100 µg DRibbles) will mediate tumor regression and increase survival time. In order to increase the efficacy of DRibbles, the optimal dose of DRibbles or Dribble-loaded DC cells can be identified using methods routine in the art.

EXAMPLE 13

Treatment of Advanced Tumors with DRibble-Loaded DC

This example describes methods used to treat advanced tumors. One skilled in the art will appreciate that similar methods can be used to treat other advanced tumors in a mammal. In addition, similar methods can be used to administer DRibbles instead of DRibble-loaded DC to a mammal.

To treat mice with more advanced tumor burden, 6-9 days after administration of the 3LL cells ($5\times10^4$ cells), mice were divided into four different groups (6-7 mice per group). Group 1 (3LL/alone), the control group, did not receive any treatment, group 2 received 150 µg anti-OX40 antibody (an antibody that recognizes OX40, which has been used as anti-lung cancer agent, for example see Kjaergaard et al., *J. Immunol.* 167:6669-77, 2001), group 3 received 3LL-DRibble-loaded dendritic cells, and group 4 received 3LL-DRibble loaded dendritic cells plus 150 µg anti-OX40 antibody (i.p.) shortly after vaccination (to booster the vaccine induced immune response).

Figure 9:
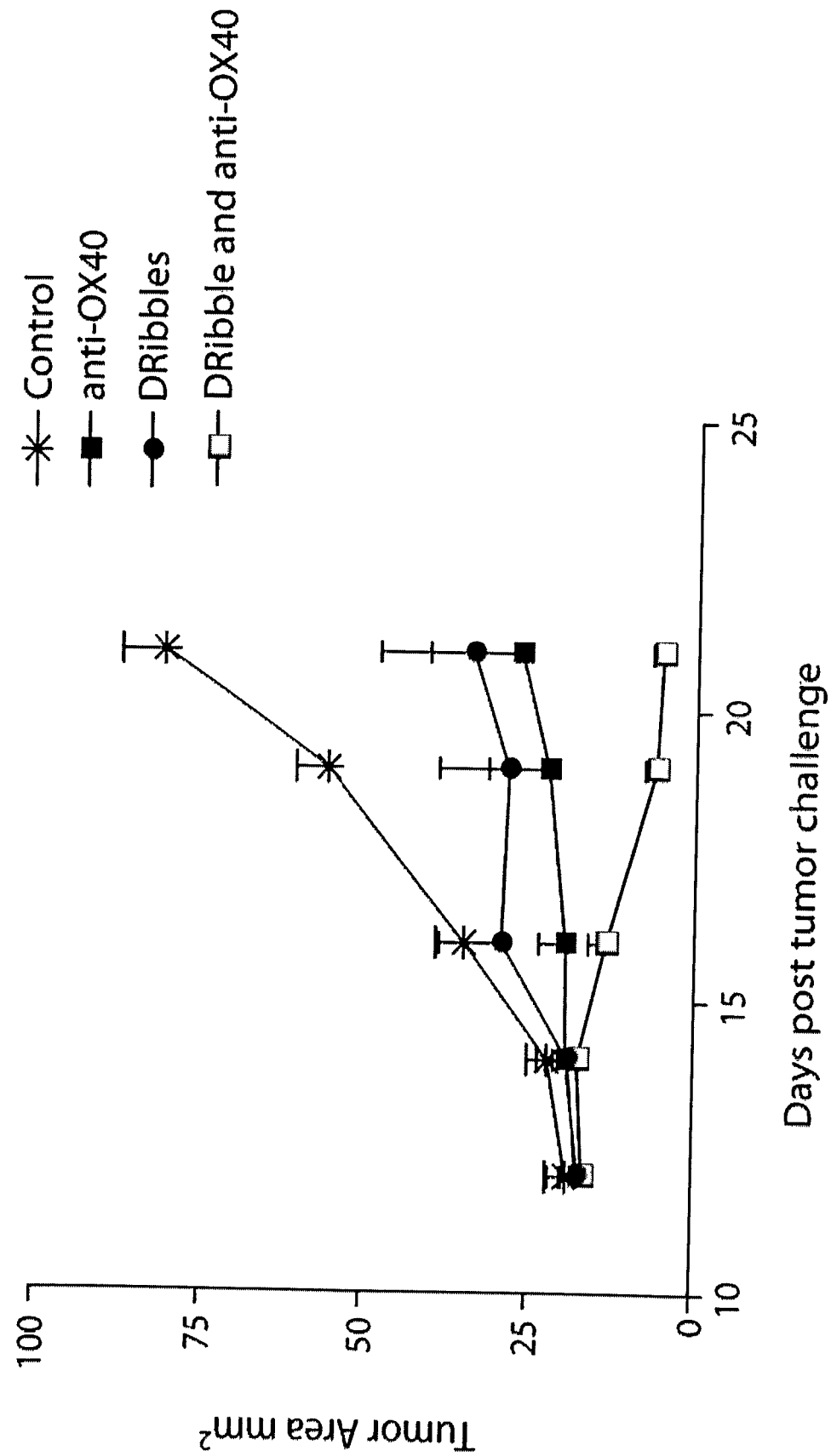
FIG. 9 is a graph showing complete tumor regression induced by administration of DRibble-loaded DC in combination with anti-OX40 antibody in an 8 day established tumor model.
Figure 11A:
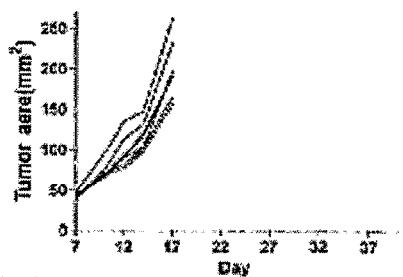
FIGS. 11A-D are graphs showing tumor regression in EMT-6 tumor model (breast carcinoma cell line derived from BALB/c mice). Mice were injected with $2 \times 10^5$ EMT-6 tumor cells. Taxotere (5 mg/kg) was administrated into mice at day 7 post tumor injection. At day 8, control mice received (A) no other treatment; (B) 100 µg anti-mouse OX40 antibody; (C) DC loaded with DRibbles derived from EMT-6 tumor cells; or (D) a combination of DC loaded with DRibbles derived from EMT-6 tumor cells plus anti-OX40 antibody. Each group consisted of eight mice, each line represents one mouse.
Figure 11B:
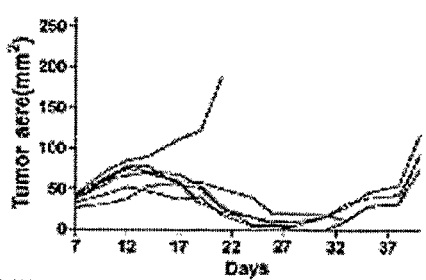
Figure 11C:
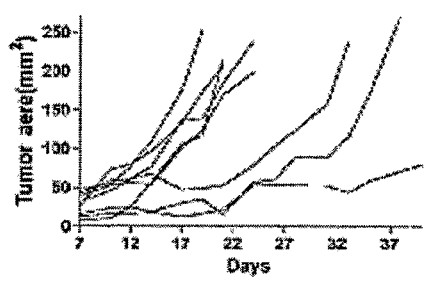
Figure 11D:
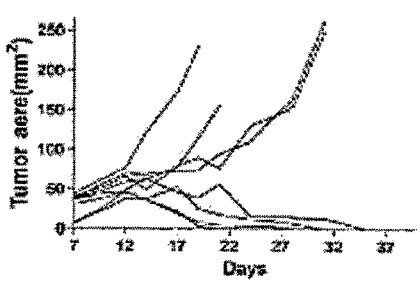

As shown in FIG. 9, 8 day established 3LL tumors in mice regressed in mice receiving DC pulsed with DRibbles derived from 3LL cells in combination with costimulatory anti-OX40 antibody. As shown in FIGS. 6A-C, administration of DRibble-loaded DC cure half of mice (3 of 6) bearing 6 day established tumors and one of six mice bearing 9 day tumors. In addition, 12 day established 3LL tumors in mice treated with DRibble plus anti-OX40 antibody (12 day tumor model) was effective to eliminate tumors in 6 of 7 mice (FIG. 10D).

B6 mice were injected with $2\times10^5$ 3LL cells subcutaneously (s.c.). Mice were vaccinated at day 12 post tumor injection with DRibble-loaded DC cells ($2\times10^6$ tumor cell equivalent), CpG and poly I:C (2.5 µg/ml) loaded on bone marrow derived DC ($1\times10^6$/ml 6 hours at 37° C.). CpG and poly I:C activate TLR9 and TLR3, respectively. Balb/c mice were injected with $2\times10^5$ EMT-6 cells (mammary carcinoma) s.c. Taxotere (5 mg/kg) was administrated into mice at day 7 post tumor injection. At day 8, mice received no other treatment (control); 100 µg anti-mouse OX40 antibody; DC loaded with DRibbles derived from EMT-6 tumor cells ($2\times10^6$ cells); or a combination of DC loaded with DRibbles derived from EMT-6 tumor cells plus anti-OX40 antibody.

As shown in FIGS. 11A-G, mice having advanced tumors administered DRibble-loaded DCs had significantly prolonged survival compared to control mice did not receive vaccine (p<0.05) (Kaplan-Meier plots and Log rank sum tests) and cured approximately 20% of mice. Concurrent triggering of TLR 3 and TLR 9 by intracellular targeting of poly I:C and CpG, respectively resulted in production of IL-12 and IFN-α by conventional DC, but also led to more efficient cross-presentation of tumor-associated antigens derived from tumor cells.

EXAMPLE 14

Treatment of Tumors with Dribbles and a PD-1 Inhibitor

This example describes methods that can be used to treat a tumor by administration of DRibbles (for example as treated cells producing DRibbles, isolated DRibbles alone, or as DRibble-loaded DC) and an agent that reduces or inhibits PD-1 signaling. In a particular example, the tumor is a large or well-established tumor. Although particular inhibitors of PD-1 signaling are described, one skilled in the art will recognize that other agents can be used, such as siRNA molecules specific for PD-1, PD-1L1, and L2.

As shown in the examples above, DRibble-based compositions are superior to whole tumor cell vaccine to induce T-cell mediated antitumor immunity. Although DRibble-based vaccines alone mediated regression of small tumors, large well-established tumors were only delayed and only a minority of mice were completely cured (see Example 13). This could result from immune suppressive mechanisms in the tumor microenvironment, such as the expression of tumor or stromal cell inhibitory ligands, for example PD-1 ligand. Consistent with PD-1's suppressive role in tumor sites, cells dissociated from the large well-established F10 tumors (including tumor cells, stromal fibroblast, and APC) expressed high levels of PD-1L1 (B7H1). Most cells in a tumor digest expressed a low level of PD-1L2 (B7DC), while a small subset of cells expressing a high level of PD-1L2 (these are likely tumor associated dendritic cells or macrophages).

Antibodies against PD-1, PD-1L1, and L2 can be used to block PD-I signaling. Mice bearing 10-12 day established F10 tumor (tumors will be around 50-100 mm$^2$) will be irradiated and adoptively transferred with pmel-1 and TRP-1 TCR T cells as described in Example 8 and then administered DRibbles (for example subcutaneously or intradermally) derived from 293 T cells expressing gp100 and TRP-1 proteins. Vaccination will be repeated 3 and 6 days later, and antibodies are administered i.p. 3 days post the last vaccination. Both number of pmel-1 and TRP-1 TCR T cells in blood will be monitored, and their ability to produce IFN-γ will be measured by peptide stimulation and intracellular staining. Tumors will be harvested and digested. The number of pmel-1 and TRP-1 T cells in tumors will be determined and the ability to produce IFN-γ will be also measured.

It is expected that the use of antibodies that inhibit PD1 activity (such as anti-PD-L1) will increase both the number and functionality of tumor-infiltrating T cells, thereby enhancing treatment of tumors, for example by prolonging survival time. In addition, it is expected that DRibble alone or DC loaded with DRibble will induce strong proliferation of pmel-1 and TRP-1 T cells in tumor-bearing mice, thereby significantly prolonging survival of tumor-bearing mice.

EXAMPLE 15

Generation of DRibbles Using Proteasome Inhibitor and Autophagy Inducer

This example describes methods that can be used to generate DRibbles in the presence of both a proteasome inhibitor and an autophagy inducer. One skilled in the art will appreciate that other tumor cells can be used, such as a tumor cell obtained from a subject having a solid or liquid tumor. Similarly, other proteasome inhibitors and other autophagy inducers can be used. One skilled in the art will also appreciate that similar methods can be used to produce DRibbles from cells infected with one or more target pathogens, such as HIV.

As disclosed in Examples 2-5 and 20, treatment of cells with both a proteasome inhibitor and an autophagy inducer enhanced cross-presentation of DRiPs and SLiPs, indicating that such an approach can be used to increase the yield of DRibbles. For example, induction of autophagy after proteasome inhibition, for example in combination with blockade of lysosome acidification with NH$_4$Cl, increased the cross-presentation activity of whole tumor cells.

Tumor cells (for example of the same tumor type present in a subject to be treated) or cells infected with a pathogen are incubated in the presence of a proteasome inhibitor (such as a reversible proteasome inhibitor) under conditions that permit inhibition of proteasome activity while maintaining maximal cell viability as well as under conditions that induce autophagy. Incubation in the proteasome inhibitor and the autophagy inducer can occur sequentially or concurrently. In one example, the cell is incubated with the proteasome inhibitor prior to the autophagy inducer. In another example, the cell is incubated with the proteasome inhibitor after to the autophagy inducer.

In some examples, lysosome mediated protein degradation is also inhibited (for example with 10 mM NH$_4$Cl). In some examples, the cells are also incubated in the presence of an agent that decreases or inhibits apoptosis, such as an inhibitor of caspase activation. The pan caspase inhibitor (Z-VAD-fmk such as 5 μM) can be used to inhibit caspase activation in the presence of the proteasome inhibitor.

Exemplary conditions include incubation of cells in at least 20 nM Velcade (such as 20-1000 nM Velcade) for 6-48 hours. Before, during, or after, the cells are incubated under conditions that induce autophagy, such as overnight incubation with 1 nM-100 nM rapamycin, with 10-1000 U/ml IFN-γ, with 5-100 mg/kg body weight vinblastine sulfate, or under nutrient deprivation (such as HBSS). In a specific example, cells are incubated in the presence of a proteasome inhibitor for at least 6 hours (such as at least 48 hours), followed by an overnight nutrition starvation to induce autophagy. In another example, cells are incubated in HBSS for 2 hours (nutrition starvation) before the addition of a proteasome inhibitor (such as Velcade) (for a total incubation of 24-48 hours).

The treated cells can be administered directly to a subject. Alternatively, the resulting DRibbles can then be isolated, for example using the centrifugation methods described in Examples 1 or 16, and then administered to a subject or used to stimulate APC cells ex vivo.

EXAMPLE 16

Isolation of DRibbles by Gradient Ultracentrifugation

This example describes gradient ultracentrifugation methods that can be used to isolate DRibbles from cells, such as tumor cells or cells infected with a pathogen. In particular examples, such methods result in a population of DRibbles that is more pure than is obtained using differential centrifugation.

Dribbles are pelleted and the resulting pellet fractionated by ultracentrifugation in a Percoll colloidal density gradient, for example using the method for purification of autophagosomes from homogenized cells (Stromhaug et al., *Biochem. J.,* 335(Pt 2), 217-24, 1998). Briefly, DRibbles are pelleted from cleared supernatant of cells (such as target tumor cells or cells infected with a target pathogen) after treatment with at least a proteasome inhibitor (such as 1 µM Velcade for 6-48 hours) by high speed centrifugation. In some examples, the cells have been incubated with other agents, such as those that induce autophagy, block lysosome acidification, reduce apoptosis, or combinations thereof. The pellet is washed with PBS twice and resuspended in 5 ml of PBS and layered on top of a discontinuous gradient of 21 ml of 33% Percoll in PBS on top of 7 ml of 22.5% Nycodenz in PBS (1.127 g/ml), and centrifuged for 30 minutes at 72,000 g in a SW28 rotor. Autophagy bodies will be banded at the lower interface, while apoptotic bodies or release mitochondria will be pelleted on the bottom of tube. Other light membranes, such ER and debris of plasma membrane, will be banded in the upper interface. As it is expected that DRibbles are autophagy bodies released from cells in the presence of one or more proteasome inhibitors, in some examples, the autophagy bodies are isolated (and can then be used in the methods disclosed herein).

Equal amount of proteins from three fractions can be subjected to Western blot analysis using antibodies against GFP (marker for antigen), LC3 (autophagosome marker), HSP90 and GAPDH (cytosolic hsp and enzyme), calreticulin and Grp94 (ER hsp), Grp78 (mitochondria hsp), ly-HSP73 and Cathepsin B (lysosomal hsp and protease), and proteasome subunits (20S and 19S) and proteasome activator (REG and PA200). Equal amount of proteins from total cell lysate can be used to determine whether any enrichment of particular components.

In addition, each of the three fractions can be used as antigen source for cross-presentation assay, to determine whether the cross-presentation activity is only found in the fraction of autophagy bodies.

EXAMPLE 17

Whole Cell Tumor Immunostimulatory Agents

This example describes methods that can be used to generate a whole-cell tumor immunostimulatory composition, which can be used as an alternative (or in addition to) DRibbles or DRibble-loaded DC cells. One skilled in the art will appreciate that similar methods can be used to prepare whole cell pathogen immunostimulatory agents, for example by using cells infected with a pathogen or a vector that encodes a pathogen antigen, instead of a tumor cell.

Whole tumor cells are incubated with a proteasome inhibitor, such as Velcade, and in some examples also an autophagy inducer. Tumor cells can be obtained from the subject to be treated, or can be obtained from another source of the same tumor type (such as from a tissue culture cell or another subject). Methods of obtaining and culturing tumor cells are routine in the art.

Tumor cells are incubated in the presence of a proteasome inhibitor (such as a reversible proteasome inhibitor) under conditions that permit inhibition of proteasome activity while maintaining maximal cell viability and in some example also under conditions that induce autophagy. Incubation in the proteasome inhibitor and the autophagy inducer can occur sequentially or concurrently. In one example, the cell is incubated with the proteasome inhibitor prior to the autophagy inducer. In another example, the cell is incubated with the proteasome inhibitor after to the autophagy inducer.

In a specific example, tumor cells are incubated with a proteasome inhibitor for at least 2 hours, such as at least 6 hours, for example 2-6 hours, followed by overnight incubation under conditions that induce autophagy in the cells. In some examples, lysosome mediated protein degradation is also inhibited (for example with 1-50 mM $NH_4Cl$, such as 10 mM $NH_4Cl$). In some examples, the cells are also incubated in the presence of an agent that decreases or inhibits apoptosis, such as an inhibitor of caspase activation. The pan caspase inhibitor (Z-VAD-fmk, such as 5 µM Z-VAD-fmk) can be used to inhibit caspase activation in the presence of the proteasome inhibitor.

Exemplary conditions include incubation of cells in at least 20 nM Velcade (such as 20-1000 nM Velcade) for at least 6 hours. Before, during, or after, the cells are incubated under conditions that induce autophagy, such as overnight incubation with 1-100 nM rapamycin, with 10-1000 U/ml IFN-γ, with vinblastine sulfate, or under nutrient deprivation (such as HBSS). In a specific example, cells are incubated in the presence of a proteasome inhibitor for at least 6 hours (such as at least 48 hours), followed by an overnight nutrition starvation to induce autophagy. In another example, cells are incubated in HBSS for 2 hours (nutrition starvation) before the addition of a proteasome inhibitor (such as Velcade) (for a total incubation of 24-48 hours).

The treated cells can be administered directly to a subject in an amount sufficient to induce an immune response, such as an amount sufficient to treat a tumor in the subject. In one example, 20-300 million treated cells are administered, for example in the presence of other agents such as an immunostimulant or an inhibitor of PD-1 (see Example 14).

EXAMPLE 18

Cross-Presentation of DRibble-Loaded DC or DRibble Alone to T Cells

This example describes methods that can be used to demonstrate that isolated DRibbles can induce a large expansion of melanoma-specific T cells in a lymphodepleted subject, thereby mediating tumor regression.

Naive $CD45.1^+$ congenic B6 mice are inoculated with F10 melanoma cells ($2 \times 10^5$) and irradiated at day 6 (500 rads). The next day, irradiated mice are adoptively transferred with $10^4$-$10^5$ naive $GFP^+$ pmel-1 T cells alone or combination with same number of naive T cells from TRP-1 TCR transgenic mice and vaccinated with $2 \times 10^6$ DC, $2 \times 10^6$ DC pulsed with peptide (positive controls), recombinant proteins, and $2 \times 10^6$ DC loaded with different amount of DRibbles (1-100 µg) generated from 293T cells expressing both gp100 and TRP-1 proteins at day 7, 10, and 12. Vaccination will be repeated two weeks later.

The number of pmel-1 T cells and TRP-1 will be followed by flow cytometry. The growth of tumor will be measured three times a week. The pmel-1 T cells will be followed by GFP and CD8 antibody, while the TRP-1 TCR T cells will be followed by CD45.2 and CD8 antibodies.

Figure 12A:
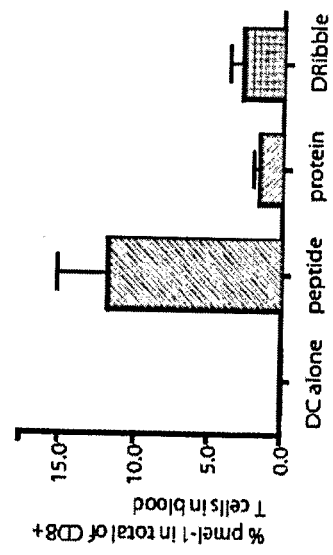
FIGS. 12A and B are graphs showing that Gp100-DRibbles (A) expanded pmel-1 T cells in tumor-bearing mice and (B) suppressed F10 tumor progression.
Figure 12B:
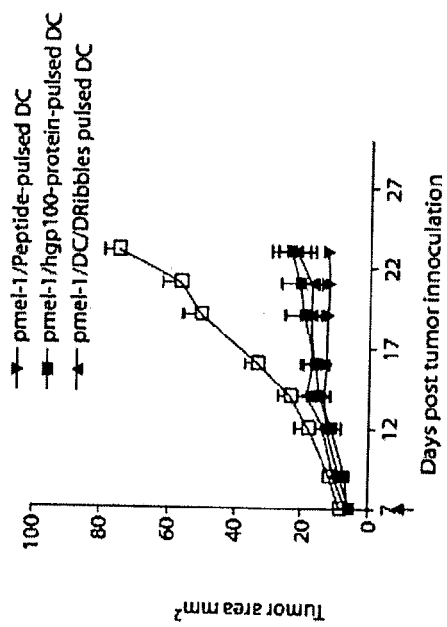

The ability of recombinant gp100 proteins, endogenous antigens from melanoma, or 293T cells transfected with gp100 and TRP-1 to cross-prime adoptively transferred pmel-1 and TRP-1 T cells can be determined. As shown in FIG. 12A, DRibble-pulsed DC (10 µl/ml) were at least as good as purified gp100 protein (10 µg/ml) to stimulate pmel-1 T cells expansion in mice bearing s.c. F10 tumors. In addition, the vaccine efficacy of DC loaded with DRibble alone, DRibble plus α-GalCer (NKT ligand), DC loaded with DRibbles in the presence of anti-CD40 and IFN-γ can be determined.

Figure 13:
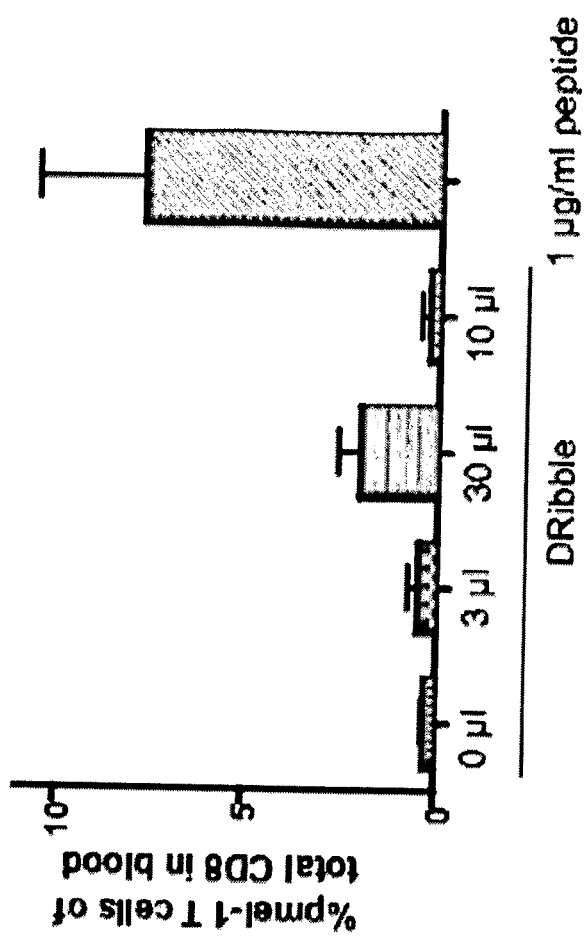
FIG. 13 is a bar graph showing that DRibbles alone can stimulate expansion of pmel-1 T cells in mice.

FIG. 13 demonstrates that intradermally administered isolated DRibbles can be targeted to DC in vivo and stimulate naive T cell proliferation without exogenous DC.

To identify the optimal amount of DRibbles administered, different amount of gp100/TRP-1-DRibbles will be delivered to mice that adoptively transferred with naive transgenic T cells via different routes (such as i.v., i.d., s.c.). Proliferation of CFSE-labeled pme-1 and TRP-1 TCR naive T cells can be monitored using routine methods and those provided herein. The dose and route that result in the greatest T-cell expansion in vivo can be used in mice bearing F10 tumors (or other subjects having a tumor). Tumor growth and T-cell responses will then be followed as above.

EXAMPLE 19

Cross-Presentation of Proteins

This example describes methods that can be used to compare the efficiency of cross-presentation of long- and short-lived proteins synthesized by tumor cells in vivo. It is expected that long-lived, but not short-lived proteins, are cross-presented efficiently by DC in vivo.

Tumor models that express gp33 of LCMV and melanoma antigen gp100 can be generated. Two forms of gp33 and gp100 will be generated, one having a long-half life, the other having a short-half-life. The $D^b$ restricted gp33 eptiope (KAVYNFATM) is recognized by T cells from P14 TCR transgenic mice (Taconic, Germantown, N.Y.). TCR Tg mice for melanoma gp100 are commercially available.

Cell lines 293T, B78H1, and βKOS (a fibrosarcoma cell line generated from β2m knockout mice) can be used. 293T is human kidney cell line and higher level of antigen expression is usually observed as compared to other cell lines. Activation of mouse T cells is via cross-presentation. B78H1 (defective TAP and N-end rule, thus no proteasome-mediated degradation of short-lived proteins targeting N-end rule and peptide translocation into ER), βKOS (β2m knockout, thus no complex formation of MHC class I and peptide in ER) can be used as Ag donor cells to determine whether substrates of proteasome, products of the proteasome, peptides translocated into ER, or MHC I/peptide complexes are the source material for cross-presentation. Effective cross-presentation of these model antigens will be measured by CFSE dilution of adoptively transferred naive TCR Tg T cells into mice bearing tumors that express these model antigens.

Cell lines expressing OVA, gp100, and TRP-1 are generated using routine methods. Irradiated 293T-M-GFP-OVA or 293T-R-GFP-OVA will be used as the Ag donor cells (or with the non-293T cells). Tumor cells are irradiated before s.c. injection into congenic mice that have been previously adoptive transferred with 1-5 million naive TCR Tg T cells. As an indication of cross-presentation, CFSE dilution of Tg T cells from vaccinated lymph nodes (LN) and spleen is monitored by flow cytometry at day 5 and 14 post tumor injection. CD8 T cells from OT-I, P14, and pmel-1 mice will be used to investigate the MHC I restricted cross-presentation, while CD4 T cells from OT-II and TRP-1 TCR Tg mice will be used to examine the MHC II restricted cross-presentation.

To demonstrate that inhibition of proteasome-mediated degradation of short-lived proteins will increase their cross-presentation, the following methods can be used. Tumor cells expressing short half-life versions of model antigens are treated with 0.05 μM Velcade for 6, 12, 24, 48, and 72 hours and irradiated. These tumor cells will be used as Ag donor cells for cross-presentation assays as described above.

To demonstrate the role of endogenous DC in the cross-presentation of tumor-derived proteins in vivo, the following methods can be used. Tg mice with a CD11c promoter-driven diphtheria toxin (DT) will be used to deplete endogenous DC transiently after tumor inoculation. Such a model is available from the Jackson laboratory (B6.FVB-Tg (CD11c-DTR-EGFP) 57Lan/J). To confirm TAP1-dependent cross-presentation, TAP1-deficient mice will be used as the recipient mice.

It is expected that in vivo cross-presentation will be dependent on endogenous DC and cross-presentation of MHC I, but not II antigens, dependent on TAP1 of dendritic cells but not on TAP of tumor cells.

EXAMPLE 20

HSP90 is Involved in Autophagy of DRiPs and SLiPs

This example describes methods used to demonstrate the role of HSP90 in autophagy of DRiPs and SLiPs.

Most if not all of misfolded or abnormal proteins are degraded by proteasomes. In the presence of HSP90 inhibitors such as geldanamycin or radiciol (17-AAD), misfolded or truncated proteins (DRiPs) are targeted to the proteasome for their degradation in a process that involves the co-chaperone CHIP, or other E3 ubiquitin ligases.

To demonstrate the role of HSP90s are in the cross-presentation of tumor-derived antigen, 293T cells expressing V-GFP-TfR-OVA fusion protein were treated with 1 μM Velcade (6 hours), 10 μM radiciol (17-AAD, an HSP90 inhibitor) (16 hour), 17-AAD (16 hour) and Velcade (last 6 hours of 16 hour) and the levels of fusion proteins in equal amount (10 μg lysate) of each sample were analyzed by western blot with anti-GFP antibody. Cross-presentation is analyzed as described in Example 5.

Velcade dramatically increased while HSP90 inhibitor reduced short-fragments of GFP-TfR-OVA fusion proteins. Treatment with 17-AAD followed by Velcade restored the accumulation of these shorter fragments. These results indicate that HSP90-associated short fragments were efficient proteasome substrates and these short fragments are likely bona fide DRiPs.

When 17-AAD treated cells were used as the source for cross-presentation, the cross-presentation was reduced. Surprisingly, the addition of Velcade rescued DRiPs but not cross-presentation. An even more pronounced inhibitory effect of 17-AAD was observed in Velcade treated cells compared to nontreated cells, the same phenomena was observed with autophagy inhibitor, 3-MA. This result indicates that HSP90s are involved in the autophagy of DRiPs. Inhibition of proteaseome function in the presence of Velcade rescued DRiPs and failed to induce autophagy, mimicking the effect of 3-MA and Velcade and thus failed to accumulate DRiPs in autophagosome and subsequent release as DRibbles.

To identify HSP90α as the carrier for cross-presentation substrate, siRNA against HSP90α can be used to transfect 293T cells expressing V-GFP-TfR-OVA fusion protein. Cells are treated with Velcade and DRibbles will be prepared from the supernatant using the methods described herein. siRNAs against luciferase and HSP90β will be used as the negative controls. The effect of HSP90s knock down on autophagy will be determined by western blot analysis of LC3 and punctate formation of GFP-LC3 or tdTomato-LC3 in transfected cells. DRiPs will be examined by western blot analysis. GFP-Ub or tdTomato-Ub fusion proteins can be used to tag aggregated ubiqintinated proteins and examine the effect of inhibition of HSP90 on Ub-positive aggregates by confocal microscope analysis. Isolated DRibbles from cells with HSP90 knock down will be used as the source of antigens for cross-presentation assay in vitro with OT-I and OT-II cells. It is expected that HSP90α but not HSP90β is involved in the autophagy of ubiquitinated DRiPs and accumulation and release of DRiPs in DRibbles from proteasome inhibited tumor cells.

EXAMPLE 21

Role of Folded Intact Proteins in the Cross-Presentation of DRiPs and SLiPs This example describes methods that can be used to determine the contribution of folded intact proteins or aggregated DRiPs in the cross-presentation of DRiPs. Both folded intact proteins and aggregated DRiPs are found in DRibbles and both of them can be cross-presented.

To determine the relative contribution of these two different protein fractions in the cross-presentation, digitonin will be used to permeablize DRibbles to release soluble GFP fusion proteins while leaving misfolded DRiPs inside DRibbles due to insoluble nature to digitonin. Such methods have been used to detect both autophagy of cytosolic enzyme, GAPDH (Lorenz et al., *Nat. Methods* 3: 205-10, 2006). DRibbles generated from 293T expressing M-GFP-OVA or V-GFP-TfR-OVA will be treated with 20 μM digitonin for on ice for 10 minutes. After permeablization, DRibbles will then pelleted against and both supernatant and pelleted will be subjected to western blot analysis to determine the release of soluble antigens and other components. Because V-GFP-TfR-OVA is a membrane bound protein, it is expected that no loss will be observed upon digitonin treatment while cytosolic M-GFP-OVA will be lost. After digitonin treatment, DRibbles will be used for cross-presentation assay. It is expected that only minimal loss of cross-presentation activity if DRiPs are the major antigen donors.

EXAMPLE 22

Treatment of Metastatic Breast Cancer

Despite the recent development of several new active chemotherapy and hormone therapy drugs, metastatic breast cancer remains, in more than 90% of cases, an incurable disease. This example describes methods that can be used to treat metastatic breast cancer, by administration of isolated DRibbles, DCs loaded with tumor-derived DRibbles, or with tumor cells producing DRibbles (for example due to contact with a proteasome inhibitor, autophagy inducer, or both). One skilled in the art will appreciate that similar methods can be used to treat any type of tumor, by treating such tumor cells using the methods disclosed herein. In addition, one skilled in the art will appreciate that other APCs can be used as an alternative to DCs. Furthermore, one skilled in the art will appreciate that treated tumor cells producing DRibbles or DRibbles isolated from such cells can be administered to the subject instead of administering DRibble-loaded DC. One skilled in the art will appreciate that the subjects can receive other therapies, such as administration of a PD-1 inhibitor.

Figure 14:
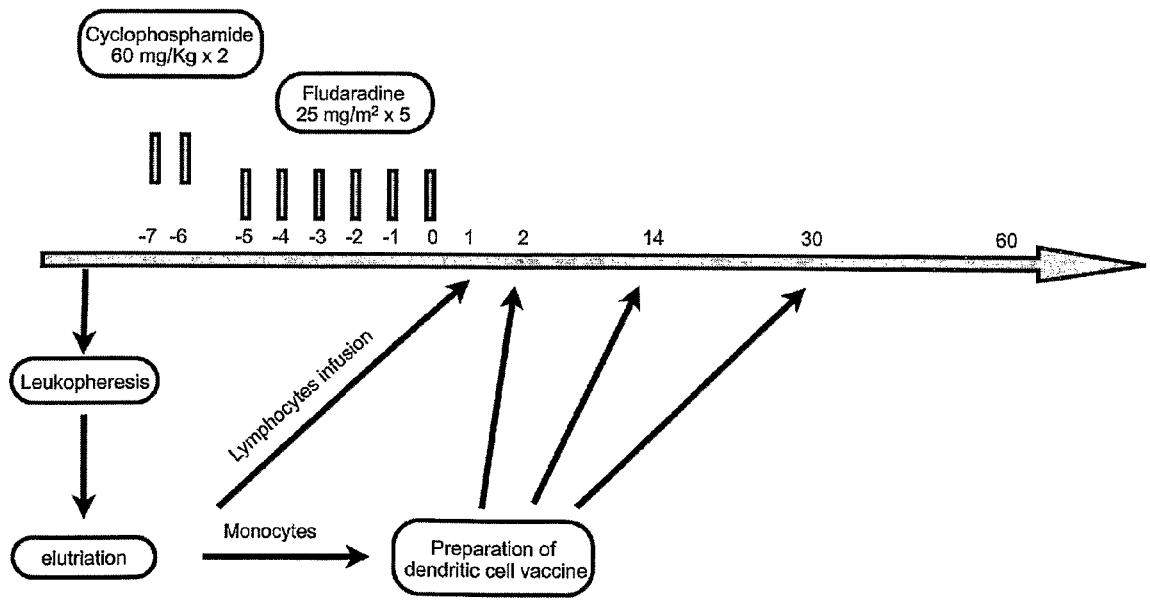
FIG. 14 is a schematic drawing showing methods that can be used to prepare and treat a mammal having a tumor by administration of DC loaded with tumor-derived DRibbles.
Figure 11E:
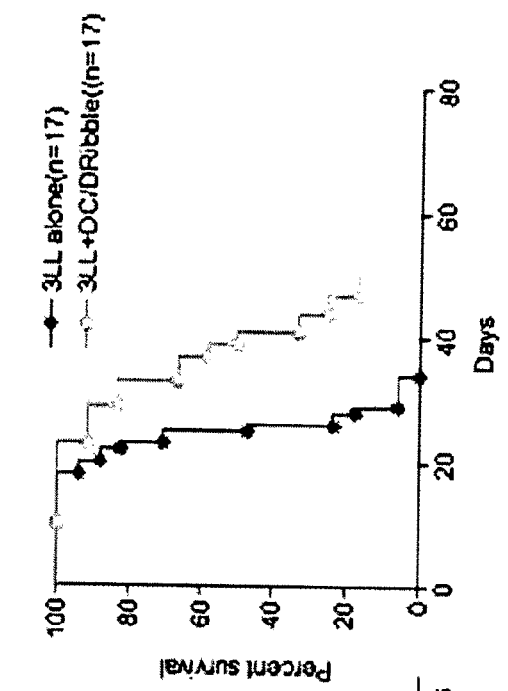
FIGS. 11E-G are graphs showing prolonged survival induced by administration of DRibble-loaded DC in 6-12 day established 3LL lewis lung carcinoma tumor model. Each line represents the data for a single mouse in (E) and (F).
Figure 11F:
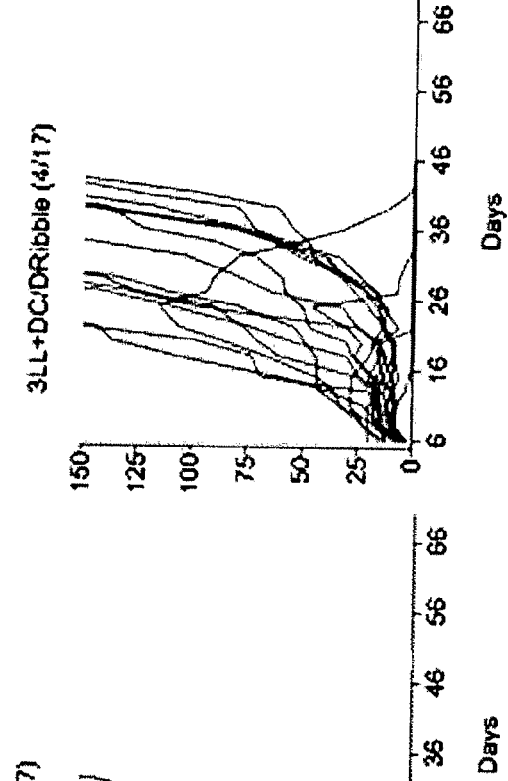
Figure 11G:
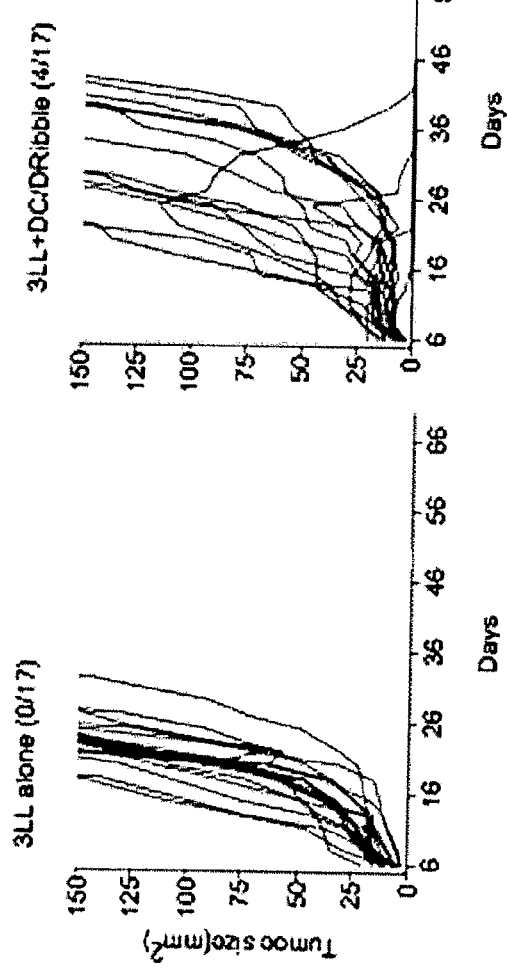

Generally, the method includes vaccinating subjects with previously untreated metastatic breast cancer with autologous DCs loaded with DRibbles derived from a breast cancer cell line (or with isolated DRibbles or treated breast cancer cells producing DRibbles), following the induction of non-myloablative lymphodepletion, plus reconstitution with an autologous peripheral blood mononuclear cell (PBMC) infusion. The general scheme is shown in FIG. 14.

For example, a small amount of the breast tumor is surgically removed, grown in culture, and frozen for later measurement of the subject's immune response against their tumor cells before and after treatment. The subject also has leukapheresis. The resulting WBC are frozen and later returned to the subject. Some of the cells can be used to generate DCs. After collecting tumor cells and the leukapheresis, subjects are treated with therapeutically effective amounts of fludarabine and cyclophosphamide chemotherapy infusion into a vein. On the sixth day the subject's frozen white blood cells are infused into the subject intravenously. The following day, the vaccine containing DRibble-loaded APCs (or isolated DRibbles or treated tumor cells producing DRibbles) is administered, for example in up to four injections under the skin in the abdomen. X-rays and scans are done at least every 13 weeks to monitor the tumors.

Subject Criteria

Subjects (20-24 subjects) having stage 1V breast cancer and who have received no chemotherapy or radiation in prior 18 months are selected (prior hormone and antibody therapy is acceptable). Ideally, subjects are ≥18 years old, have a life expectancy of greater than 3 months, and have an ECOG performance status≤2 (Karnofsky≥60%; see Table 1).

TABLE 1

Performance Status Criteria

| ECOG Performance Status Scale | | Karnofsky Performance Scale | |
| --- | --- | --- | --- |
| Grade | Descriptions | Percent | Description |
| 0 | Normal activity. Fully active, able to carry on all pre-disease performance without restriction. | 100 | Normal, no complaints, no evidence of disease. |
| | | 90 | Able to carry on normal activity; minor signs or symptoms of disease. |
| 1 | Symptoms, but ambulatory. Restricted in physically strenuous activity, but ambulatory and able to carry out work of a light or sedentary nature (e.g., light housework, office work). | 80 | Normal activity with effort; some signs or symptoms of disease |
| | | 70 | Cares for self, unable to carry on normal activity or to do active work. |
| 2 | In bed <50% of the time. Ambulatory and capable of all self-care, but unable to carry out any work activities. Up and about more than 50% of waking hours. | 60 | Requires occasional assistance, but is able to care for most of his/her needs. |
| | | 50 | Requires considerable assistance and frequent medical care. |

TABLE 1-continued

Performance Status Criteria

| ECOG Performance Status Scale | | Karnofsky Performance Scale | |
|---|---|---|---|
| Grade | Descriptions | Percent | Description |
| 3 | In bed >50% of the time. Capable of only limited self-care, confined to bed or chair more than 50% of waking hours. | 40 | Disabled, requires special care and assistance. |
| | | 30 | Severely disabled, hospitalization indicated. Death not imminent. |
| 4 | 100% bedridden. Completely disabled. Cannot carry on any self-care. Totally confined to bed or chair. | 20 | Very sick, hospitalization indicated. Death not imminent. |
| | | 10 | Moribund, fatal processes progressing rapidly. |
| 5 | Dead | 0 | Dead |

In addition, subjects ideally have normal organ and marrow function, for example: WBC of ≥3,000/uL; absolute neutrophil count of ≥1,500/uL; absolute lymphocyte count of >500/uL; platelet count of ≥100,000/uL; Hgb of ≥10 g/dl (patients can be transfused to reach this level); Hct of ≥24%; total bilirubin of <2 (unless due to Gilbert's disease) AST (SGOT)/ALT (SGPT) of <3; and creatinine of <2 mg/dl. A baseline CBC will be done within 14 days before the procedure. Ideally, the subject will have: WBC greater than 2000; platelet count greater than 50,000; Hgb greater than 8; and Hct greater than 24.

Ideally, subjects are negative for: HIV-1, HIV-2, hepatitis B surface antigen, hepatitis C antibody, HTLV 1 and 2, and syphilis. Subjects can be positive or negative for CMV and EBV, and can have a rheumatoid factor of <43 units/µL and an anti-nuclear Antibody value of <11 units/µL. If patients have had recent surgery, ideally they are fully recovered from the effects of that surgery.

Ideally, the subjects will not be: women who are pregnant or nursing; subjects who have had chemotherapy within 3 weeks or have had radiation therapy within 2 weeks; subjects receiving steroid therapy (other than replacement steroids and inhaled steroids within 2 weeks); subjects with known brain metastases unless treated with radiation therapy and/or surgery and shown to be stable ≥1 month after treatment; those having a history of multiple sclerosis, systemic lupus erythematosis, or myasthenia gravis; subjects with any form of primary or secondary immunodeficiency (such as HIV seropositive, Hepatitis C seropositive, or Hepatitis B antigen positive); subjects having uncontrolled intercurrent illness including, but not limited to: active infection, active bleeding (such as hemoptysis or GI bleeding), symptomatic congestive heart failure, unstable angina pectoris, cardiac arrhythmia, bronchospasm, hypertension, hyperglycemia or hypercalcemia. Subjects who might require systemic corticosteroids other than replacement steroids during the next three months are ideally not considered.

Baseline Leukapheresis

Subjects will undergo leukapheresis within two weeks of the start of lymphodepeltion to obtain PBMC for reconstitution and for immune monitoring. At least $1\times10^{10}$ PBMC will be obtained. Approximately 10 liters of blood will be processed over 3-6 hours. The median yield of PBMC from a 2.5 hour leukapheresis that processed a median of 7.7 liters was $8.35\times10^9$ PBMC, of which 25% are monocytes.

Calcium gluconate (10 ml) in 100 ml normal saline (NS) is infused at 0.5 ml/min or 30 ml/hr during the procedure. Subjects whose peripheral access is inadequate can have a temporary hemodialysis catheter placed under direct ultrasound guidance. The catheter will be removed after the leukapheresis procedure.

After pheresis, the product is separated into lymphocyte and monocyte fraction by elutriation with adapted MNC protocol (Rouard et al., *Transfusion* 43:481-7, 2003). Lymphocytes will be processed and frozen for later autologous reinfusion according to ARC standard procedure for Hematopoietic Progenitor Cell processing, storage and reinfusion. At the time of reinfusion, a sample of the product will be used for CBC with differential to determine the number of lymphocytes reinfused into each subject.

If mild symptomatic hypocalcemia occurs during leukapheresis (tingling of lips/face, numbness in extremities, muscle cramps), oral Tums will be given as needed. For subjects who become neutropenic and febrile, empiric antibiotic treatment with ceftazadime or imipenem can be given. Packed red blood cell transfusions are given if subjects have symptomatic anemia or if their Hgb less than 8 g/dl. Platelet transfusions can be given if the platelet count falls below 10,000 µL or at higher levels if evidence of bleeding is present.

Both CMV positive and CMV negative subjects can receive CMV prophylaxis (valgancyclovir 900 mg orally once per day) when the absolute lymphocyte count decreases below 500 per µL and continue until the lymphocyte count is consistently above this level.

G-CSF (granulocyte-colony stimulating factor) can be administered to subjects who are neutropenic with serious infections or to subjects with prolonged granulocytopenia.

A baseline CBC can be performed within 3 days of the procedure. Ideally, subjects who will receive the vaccine will have a WBC≥3,000; platelet count≥100,000; Hgb≥8 g/dl; and Hc greater than 24%

Chemotherapy

Prior to immunostimulation with DC exposed to DRibbles (or with isolated DRibbles or treated tumor cells producing DRibbles) and infusion of PBMCs, chemotherapy can be administered according to guidelines based on early adoptive immunotherapy trials (Dudley et al. *Science* 298:8504, 2002; Rosenberg and Dudley, *Proc. Natl. Acad. Sci. USA* 101:14639-45, 2004). Briefly, cyclophosphamide 60 mg/Kg/day IV over 30 minutes each day for 2 consecutive days (days −7 and −6) followed by fludarabine 25 mg/m²/day IV over 30 minutes for five days (days −5, −4, −3, −2, and −1) will be administered to the subject. Hydration and antiemetics (excluding dexamethasone) can be used at the treating physician's discretion, for example to prevent nausea.

Cyclophosphamide(2-[bis(2-chloroethyl)amino]tetrahydro-2H-1,3,2 oxazaphosphorine 2-oxide monohydrate) is a synthetic antineoplastic drug with the molecular formula $C_7H_{15}Cl_2N_2O_2P.H_2O$ and a molecular weight of 279.1. Lyophilized CYTOXAN® (cyclophosphamide for injection, USP) contains 75 mg mannitol per 100 mg cyclophosphamide (anhydrous) and can be reconstituted with sterile water or normal saline. For example, CYTOXAN® will be diluted in about 150 cc of normal saline and infused IV over 30-60 minutes. An added dose of IV fluids may help prevent bladder toxicity. Although the reconstituted cyclophosphamide is stable for six days under refrigeration, it contains no preservatives and therefore ideally is used within 6 hours.

CYTOXAN® Tablets (cyclophosphamide tablets, USP) are for oral use and contain 25 mg or 50 mg cyclophosphamide (anhydrous). Cyclophosphamide is well absorbed after oral administration with a bioavailability greater than 75%. The unchanged drug has an elimination half-life of 3 to 12 hours.

Fludarabine phosphate (FAMP) (9H-Purin-6-amine, 2-fluoro-9-(5-0-phosphono-D-arabinofuranosyl), molecular formula $C_{10}H_{13}FN_5O_7P$, is a synthetic nucleotide analogue of the antiviral agent viderabine. Also referred to in the literature as fludarabine phosphate, 2-fluoro-Ara-AMP, 2-fluoroadenine arabinoside-5-phosphate, 2-FAMP. For injection, 50 mg fludarabine phosphate is dissolved in 2 ml sterile water for injection, USP. The resulting solution contains 25 mg/ml of fludarabine phosphate. The drug can be further diluted with 5% Dextrose Injection USP or 0.9% Sodium Chloride USP. For example, Fludara for Injection should be prepared for parenteral use by aseptically adding Sterile Water for Injection USP. The pH range for the final product is 7.2-8.2. The resulting fludarabine phosphate solution can be diluted in 100 cc or 125 cc of 5% Dextrose Injection USP or 0.9% Sodium Chloride USP, and the resulting solution administered to the subject via IV over 30 minutes.

Reconstituted Fludara for Injection contains no antimicrobial preservative and thus should be used within 8 hours of reconstitution. Ideally, fludarabine is not administered unless the ANC is ≥1500 and the platelet count is ≥100,000 on the day of treatment.

Preparation of Dribbles and Dribble-Loaded Dendritic Cells (DC)

DRibbles generated from the MDA-MB-231 cell bank (Dols et al. *Hum. Gene Ther.* 14:1117-23, 2003) will be prepared. Previously, a working breast cancer cell bank (MDA-MB-231) that express multiple known antigens (Her2, Cycling B1) was used to vaccinate 36 women with breast cancers and up to $10^8$ cells were safely administrated (Dols et al *Hum. Gene Ther.* 14:1117-23, 2003). DRibbles can be generated from this cell bank due to the difficulty of establishing autologous breast cancer cell lines. One skilled in the art will appreciate that DRibbles can be generated from autologous breast cancer cells if such cells are sufficient in number, or if it is possible to grow such cells in culture.

DRibble production from MDA-MB-231 cells will be induced by overnight treatment with 20 nM Velcade® (bortezomib) (protease inhibitor). In some examples this will be performed under starvation conditions (for example in the presence of HBSS). If desired, such treated cells can be administered to the subject (to immunostimulate the subject) without subsequently isolating the DRibbles. If desired, DRibbles can be isolated as follows. Following a low-speed centrifugation, resulting DRibbles are harvested from the supernatant by centrifugation at 9,000 rpm (10,000 g) for 15 minutes. The resulting pellet containing DRibbles will be washed with PBS three times to remove the protease inhibitor. The protein content will be determined with RCA method after dissolving in 1% NP-PBS. The DRibbles will be diluted with PBS to a final concentration of 1 mg/ml and frozen in aliquots at −80° C. If desired, DRibbles can be used to directly immunostimulate the subject (for example at a concentration of 1-1,000 μg, such as 10 μg, 100 μg, or 1 mg), or used to load APCs (such as DC), and the loaded APCs administered to the subject as described below.

Monocytes will be enriched from apheresis products using the Elutra® (Gambro BCT) closed separation system. While keeping the centrifuge speed constant, fractions were collected with stepwise increase in flow rate. Typical purity and yield of this procedure are more than 90% and 70% respectively.

The monocyte fraction ($1-2\times10^9$ in 250 ml of CellGro® DC media, CellGenix USA) will be cultured in cell factories (Nalge Nunc) for 6 days. The expected yield will be 200-300 million immature DC. GM-CSF (100 U/ml) and IL-4 (10 ng/ml) will be used to culture monocytes for 6 days to generate DCs. DCs will be washed before freezing to remove GM-CSF and IL-4.

On day 6 of DC culture, DC are harvested and resuspended at $5\times10^6$ cells per ml in DC media and incubated with 10-50 μg/ml DRibbles from the breast cancer cell line MDA-MB-231 (see above) for 6 hours. Following the incubation with DRibbles, DC are washed in PBS twice, and frozen in $25\times10^6$ aliquots. The expected yield is 200 million antigen-loaded DC.

Vaccination

Beginning on day 0 (one day after the last dose of fludarabine), subjects are immunized subcutaneously with a total of $20\times10^6$ DRibble-loaded DC (or with 1-1000 μg isolated DRibbles or with at least 20 million (such as 20-200 million) treated tumor cells producing DRibbles) before the PBMC infusion. Briefly, DRibble-loaded DC (or isolated DRibbles or treated tumor cells producing DRibbles) prepared as described above are rapidly thawed (if previously frozen) at 37° C. dry bath and washed with PBS twice and resuspended in 2 ml of saline for injection. A total volume of 2 mL DC in 2 tuberculin syringes will be used for administration as two 1 ml injections of $10\times10^6$ DC in the subcutaneous tissue in two separate sites. Injections are administered within 2 hours of thawing. Vaccinations can be rotated among all extremities. The abdomen and flank can also be used. Subjects are observed for fifteen minutes after each vaccination.

The vaccinations are repeated every two weeks for five total vaccinations unless conditions for discontinuation are met (see below). Subjects will not be retreated if any acute systemic toxicity greater than grade 2 attributable to the vaccine administration occurs. Subjects are allowed to continue receiving vaccine for grade 2 toxicities commonly associated with the vaccine including skin rash, fever, malaise, adenopathy and local reactions. If severe local toxicity such as ulceration or sterile abscess occurs, the number of DC will be decreased in subsequent vaccines to 50% of initial dose. If the toxicity recurs at the lower dose, then the vaccines will be discontinued. Unexplained visual changes detected clinically will result in discontinuation of the vaccine because of the possibility that the vaccine induced a response to pigmented cells within the retina.

If manifestations of auto-immune disease occur (such as inflammatory arthritis, vasculitis, pericarditis, glomerulonephritis, erythema nodusum), then appropriate medical management will be offered including non-steroidal anti-inflammatory agents, steroids, or other immunosuppressive medications as dictated by the clinical situation and vaccination discontinued.

Autologous Peripheral Blood Mononuclear Cell Infusion

On Day 0, subjects are also infused with their previously frozen autologous PMBC. Premedication can include acetaminophen (650 mg) and diphenhydramine (50 mg) by mouth 30 minutes before the PBMC infusion. The minimum number of PBMCs that will be infused is $4\times10^9$. In one example, the maximum number of PBMCs infused is $10^{11}$. The PBMC will be infused IV push over five minutes for each 50 cc syringe. The cell infusions will be given through a large bore IV line suitable for a blood transfusion without a filter.

The subject is hydrated for 4 hours before and for 4-6 hours following the PBMC infusion to help protect against renal failure. Hydration will be adjusted to insure urine output of at least 100 ml/hr. Hydration will be achieved by infusing $D_5W\frac{1}{2}NS+20$ mEq KCl+50 mEq $NaHCO_3$ per liter at a rate of 150 ml/hr.

Vital signs will be obtained at baseline, after 20 cc have infused and at the end of the infusion. Thereafter, vital signs will be obtained every thirty minutes for two hours and then every hour for four hours. From the day after reinfusion until neutrophils recover to at least 1,000 µL and lymphocytes to at least 500/µL, subjects are monitored for infection.

Duration of Therapy

In the absence of treatment delays due to adverse events, treatment can continue until one or more of the following occurs: disease progression (subjects without progression can continue treatment for at least one year); intercurrent illness that prevents further administration of treatment; unacceptable adverse event(s); subject decides to terminate treatment; or changes in the subject's condition render the subject unacceptable for further treatment. In particular examples, the treatments are repeated, for example every 2 weeks, for example for up to a few years (such as up to 5 years).

Subjects will receive no additional vaccinations if they experience any of the following toxicities: grade 3 allergy/immunology, grade 3 hemolysis, grade 3 cardiac, grade 3 coagulation, grade 3 endocrine, grade 3 gastrointestinal, grade 4 infection, grade 3 metabolic, grade 3 neurology, grade 3 ocular, grade 3 pulmonary, and grade 3 renal.

Second Collection of PBMCs

If desired, subjects can undergo a second collection of mononuclear cells for analysis of immune function, such as approximately 2 weeks after the fifth vaccine. The product need not be processed for re-infusion into the subject. Approximately two weeks following the vaccination, leukapheresis for collection of PBMC will be performed over 2-3 hours. PBMCs will be collected at 1 ml/min, at <3% colorgram, and over a minimum of 2 hours. The procedure does not require intravenous hydration and is generally well tolerated.

Clinical Evaluations

A complete medical history, including previous cancer history and therapy, is obtained. A complete physical exam is performed, including height, weight and vital signs.

Tumors can be assessed as follows. A radiographic staging assessment of known sites of metastatic disease is performed within 4 weeks of day 1 chemotherapy. In addition, and MRI of the head with and without contrast can be performed.

Prior to each leukapheresis procedure, CBC parameters will be evaluated.

Approximately two weeks following the fifth vaccination, subjects can undergo re-staging imaging studies to evaluate anti-tumor response. Staging is repeated after every two additional vaccines (every two months). Subjects with stable disease or better can continue vaccination for one year (up to a total of 16 vaccines).

After all vaccinations are completed, subjects may be followed every 3 months for long-term toxicity and survival for the duration of their life.

Methods for Analysis of Tumors

Subjects can be reevaluated for response after the first five vaccinations, and then after every two vaccinations (every 2 months). In addition to a baseline scan, confirmatory scans can be done 4-8 weeks following initial documentation of objective response.

Response and progression can be evaluated using the international criteria proposed by the Response Evaluation Criteria in Solid Tumors (RECIST) Committee (JNCI 92(3):205-16, 2000) which are incorporated by reference. Changes in only the largest diameter (unidimensional measurement) of the tumor lesions are used in the RECIST criteria. Lesions are either measurable or non-measurable using the criteria provided below. The term "evaluable" in reference to measurability will not be used.

Evaluation of Lesions Response to Vaccine

For target lesions, a complete response (CR) is the disappearance of all target lesions. A partial response (PR) is at least a 30% decrease in the sum of the longest diameter (LD) of target lesions, taking as reference the baseline sum LD. Progressives disease (PD) is an observation of at least a 20% increase in the sum of the LD of target lesions, taking as reference the smallest sum LD recorded since the treatment started or the appearance of one or more new lesions. Stable disease (SD) is the observation of neither sufficient shrinkage to qualify for PR nor sufficient increase to qualify for PD, taking as reference the smallest sum LD since the treatment started.

For non-target lesions, a complete response (CR) is the disappearance of all non-target lesions and normalization of tumor marker level. An incomplete response can be the observation of Stable Disease (SD), the persistence of one or more non-target lesion(s) and/or maintenance of tumor marker level above the normal limits. Progressive Disease (PD) is the appearance of one or more new lesions and/or unequivocal progression of existing non-target lesions.

To be assigned a status of PR or CR, changes in tumor measurements can be confirmed by repeat assessments performed between 4 and 8 weeks after the criteria for response are first met. In the case of SD, follow-up measurements ideally satisfy the SD criteria at least once after study entry at a minimum interval of six to eight weeks.

The duration of overall response is measured from the time measurement criteria are met for CR or PR (whichever is first recorded) until the first date that recurrent or progressive disease is objectively documented (taking as reference for progressive disease the smallest measurements recorded since the treatment started).

The duration of overall CR is measured from the time measurement criteria are first met for CR until the first date that recurrent disease is objectively documented.

Stable disease is measured from the start of the treatment until the criteria for progression are met, taking as reference the smallest measurements recorded since the treatment started.

All subjects will be assessed for response to treatment. Each subject is assigned one of the following categories: 1) complete response, 2) partial response, 3) stable disease, 4) progressive disease, 5) early death from malignant disease, 6) early death from toxicity, 7) early death because of other cause, or 9) unknown (not assessable, insufficient data). Subjects in response categories 4-9 are considered as failing to respond to treatment (disease progression).

Endpoints (Immune Parameters, Toxicity Parameters, Tumor Responses)

Toxicity parameters will be measured primarily by counts of granulocytes and lymphocytes (number of cells per microliter). The amount of time to return to >200 lymphocytes/µL and 1000 neutrophils/µL is determined.

Several assays are known in the art that can be used to characterize T lymphocyte responses. Data from these assays are typically displayed as bivariate scatter plots on logarithmic scales, often referred to in the literature as "two-parameter histograms." Vertical and horizontal reference lines (calibrated statistical "cursors") divide the scatter plots into four quadrants, positive/positive events being displayed in the upper right quadrant. One primary endpoint, or criterion measure, for the immune parameters, is a percentage value (or frequency) represented by the number of $CD8^+$ T cells to the total number of gated $CD8^+$ T lymphocytes (expressed as a percentage) that make intracellular IFN-$\gamma$. Analyses can include pairwise comparisons of intra-patient (within-subject) scores (such as pre-vaccine vs. post-vaccine frequencies). These will be continuous random variables, typically small numbers, varying from 0.05% to 5.0%.

Anti-tumor immune responses are measured before and after treatment (such as 60 days post initial vaccination). T cells from leukophoresis products before and after treatment are isolated with MACS bead by negative selection. T cells are stimulated with DRibble/DC used for vaccine, or autologous tumor cells if available in presence of a Golgi blocker that allows accumulation of cytokines inside cells.

IFN-$\gamma$ production by T cells can be measured by intracellular staining techniques after cell surface staining with CD4 and CD8 antibodies. For example, T cells stimulated with a specific (breast cancer) and non-specific tumor cell (such as prostate or melanoma cells) can be stained with labeled antibodies for CD4, CD8, and IFN-$\gamma$. Using flow cytometry, the signals are detected to determine the percentage of CD4 and CD8 T cells produce IFN-$\gamma$ with or without stimulation are determined. The tumor-specific response is when CD8 and CD4 cells produce IFN-$\gamma$ in the presence of the breast tumor cells, but not the non-specific tumor cells.

EXAMPLE 23

Treatment of a Tumor by Administration of a Proteasome Inhibitor

This example describes methods that can be used to treat a tumor in a subject (such as a human or veterinary subject), wherein the method includes administration of one or more proteasome inhibitors to the subject, thereby producing DRibbles in vivo. In some examples, the method also includes administration of therapeutically effective amounts of other agents, such as agents that induce autophagy (such as rapamycin).

A subject having a tumor is administered one or more proteasome inhibitors, such as Velcade®, in an amount sufficient to stimulate or enhance production of DRibbles by the tumor in the subject. In particular examples, the proteasome inhibitor is administered in an amount that does not significantly cause apoptosis of the tumor cells, but instead permits an immune response via T-cells to treat the tumor. In a particular example, the subject is administered no more than 1 mg/m²/dose Velcade®, such as no more than 0.1 mg/m²/dose or no more than 0.01 mg/m²/dose Velcade®.

In addition to the proteasome inhibitor, other therapeutic agents can be administered to the subject, for example at a time before, during or after administration of the proteasome inhibitor. For example, tunicamycin or other agent that reduces glycosylation of proteins can be administered at a sub-lethal dose in combination with a proteasome inhibitor (or a time soon before or after administration of the proteasome inhibitor), for example to enhance production of DRibbles by tumor cells in the subject. In another or additional example, an immunostimulant or adjuvant, such as a cytokine, is administered to the subject, for example to enhance the immune response against the tumor-derived DRiPs, following the formation of DRibbles in the subject. In yet another example, one or more agents that inhibit PD-1 signaling (such as antibodies or siRNA molecules) are administered to the subject at therapeutically effective doses (see Example 14). In yet another example, one or more agents that induce autophagy are administered to the subject. For example, 20 mg/kg CCI-779 can be administered via i.v. infusion (for example in one or more doses, such as 1-5 doses). In yet another example, combinations of these other therapeutic agents are administered.

EXAMPLE 24

Treatment of a Tumor by Administration of Tumor-Derived DRibbles

This example describes methods that can be used to treat a tumor in a subject, wherein the method includes administration of tumor cell-derived DRibbles that were produced ex vivo.

Tumor cells can be obtained from the subject to be treated, or can be of the same tumor type by obtained from another subject (such as a tissue culture cell line). Methods of obtaining tumor cells are known in the art. The tumor cells are cultured using standard tissue culturing methods, under conditions that support viability of the cells. The cells are incubated in the presence of a proteasome inhibitor, such as 5 µg/ml MG132 or ALLM, or 20-1000 nM Velcade®, under conditions sufficient to block proteasome-mediated degradation of proteins, thereby allowing the tumor cells to produce DRibbles. For example, the tumor cells can be cultured with the proteasome inhibitor for 6-48 hours, such as overnight, at 37° C.

In particular examples, the tumor cells are also incubated under conditions that promote autophagy, for example by starving the cells or incubating the cells in amounts of rapamycin, $NH_4Cl$, or combinations thereof that promote autophagy of the tumor cells. For example, tumor cells treated with a proteasome inhibitor can be subsequently incubated under conditions that promote autophagy, such as conditions that starve the cells (for example overnight incubation in HBSS media), or incubation in the presence of 10-100 nM rapamycin or 10 mM $NH_4Cl$.

The cells can be co-incubated with tunicamycin or other agent (such as brefeldin A) that reduces glycosylation under sub-lethal conditions sufficient to enhance DRibble production. For example, cells can be incubated in the presence of 5 µg/ml MG132 or ALLM, or 20-1000 nM Velcade®, in combination with 5 µg/ml tunicamycin, for 6-48 hours at 37° C.

DRibbles produced by the tumor cells can be harvested as follows. Cells and culture supernatant are collected and whole cells and large cell debris removed by a low speed centrifugation (250 g for 10 minutes). The resulting supernatant is further centrifuged at a high speed (10,000 g for 15 minutes) to pellet DRibbles. The pellets (containing the DRibbles) are washed once by re-suspending in PBS (20 ml) and pelleting at high speed as above. The washed pellets are resuspended in 300 µl PBS (10 µl DRibble=1 million cells) and snap frozen in liquid nitrogen and kept at −80° C. in small aliquots until use. Alternatively, the ultracentrifugation method described in Example 16 can be used.

The tumor-derived DRibbles can be administered to a subject directly at a concentration of 1-1000 mg DRibbles per dose. The subject can receive multiple doses, depending on the response of the subject to the DRibble composition. In one example, the subject receives DRibbles every two weeks, over at least a 3 month period (such as for at least 6 months or at least 12 months). In another example, the subject receives DRibbles every two weeks for a month, then every month for at least one year.

In addition to the DRibble composition, the subject can receive other therapeutic agents at a time during, prior, or after administration of DRibbles. For example, the subject can also be administered an immunostimulant, anti-tumor agent (such as a chemotherapeutic agent), or combination thereof.

In yet another example, one or more agents that inhibit PD-1 signaling (such as antibodies or siRNA molecules) are administered to the subject at therapeutically effective doses (see Example 14).

EXAMPLE 25

Treatment of a Tumor by Administration of DRibble-Loaded APCs

This example describes methods that can be used to treat a tumor in a subject, wherein the method includes administration of APCs that have been loaded with tumor cell-derived DRibbles produced ex vivo.

DRibbles are produced from tumor cells using the methods described in Example 1, 15, or 16, and are used to load dendritic cells ex vivo. Dendritic cells are obtained from PBMCs as described in Example 22. On day 6 of DC culture, DC are harvested and resuspended at $5\times10^6$ cells per ml in DC media and incubated with 10-50 µg/ml DRibbles for 6 hours. Following the incubation with DRibbles, DC are washed in PBS twice, can be frozen in $25\times10^6$ aliquots. The expected yield is 200 million antigen-loaded DC.

At the time of administration, DRibble-loaded DC are rapidly thawed at 37° C. if needed, and washed with PBS twice and resuspended in 2 ml of saline for injection. The DRibble-loaded DC composition is administered to a subject directly at a dose of $20\times10^6$ DRibble-loaded DC, for example as two 1 ml injections of $10\times10^6$ DC in the subcutaneous tissue in two separate sites. The subject can receive multiple doses, depending on the response of the subject to the composition. In one example, the subject is administered the composition every two weeks, over a 3 month period.

In addition to the DRibble-loaded DC composition, the subject can receive other therapeutic agents at a time during, prior, or after administration of DRibble-loaded DC composition. For example, the subject can also be administered an immunostimulant (such as an adjuvant), anti-tumor agent (such as a chemotherapeutic agent), or combination thereof.

In yet another example, one or more agents that inhibit PD-1 signaling (such as antibodies or siRNA molecules) are administered to the subject at therapeutically effective doses (see Example 14).

EXAMPLE 26

Treatment of a Tumor by Administration of Tumor Cells Contacted with Proteasome Inhibitor and Autophagy Inducer This example describes methods that can be used to treat a tumor in a subject, wherein the method includes contacting tumor cells of the same type as present in the subject with one or more agents that inhibit the proteasome and one or more agents that induce autophagy.

Tumor cells are incubated in the presence of one or more agents that inhibit the proteasome and one or more agents that induce autophagy. The tumor cells are of the same type present in the subject. For example, if the subject has lung cancer, the tumor cells are the same type of lung cancer. In some examples, the tumor cells are obtained from the subject, for example biopsy material. In yet other examples, the tumor cells are obtained from another subject. Methods of obtaining tumor cells are known in the art.

In one example, tumor cells are incubated in the presence of one or more agents that inhibit the proteasome and one or more agents that induce autophagy ex vivo. For example, tumor cells of the same type present in the subject are cultured in the presence of one or more agents that inhibit the proteasome and one or more agents that induce autophagy. Incubation with the one or more agents that inhibit the proteasome and one or more agents that inhibit the proteasome can occur simultaneously, or one after the other. Such agents are used in an amount sufficient to stimulate or enhance autophagy and production of DRibbles by the tumor cells.

The tumor cells are cultured using standard tissue culturing methods, under conditions that support viability of the cells. In a specific non-limiting example, 5-20 million tumor cells (such as 10 million cells) are incubated in the presence of 20-1000 nM Velcade for at least six hours, washed, then incubated overnight in HBSS media (this starves the cells). If desired, the treated tumor cells can be cryopreserved prior to use (for example in $20\times10^6$ cells per aliquot). At the time of administration, treated tumor cells DRibble-loaded DC are rapidly thawed at 37° C. if needed, and washed with PBS twice and resuspended in 2 ml of saline for injection into the subject to be treated. Treated tumor cells (20-300 million, such as 5-20 million or 20-200 million cells) are administered to the subject (for example via intradermal or subcutaneous injection or via a pump). The subject can receive multiple doses, depending on the response of the subject to the composition. In one example, the subject is administered the composition every two weeks, over at least 3 months (such as at least 6 months or at least 12 months). In another example, the subject is administered the composition every 2 weeks and then monthly for 1 year. In another example, the subject is administered the composition every week, for example for at least 3 months, at least 6 months or at least 12 months. Particular dosages and dosing regimens can be determined by skilled clinicians.

In addition to the treated tumor cells, the subject can receive other therapeutic agents at a time during, prior, or after administration of tumor cells. For example, the subject can also be administered an immunostimulant (such as an adjuvant), anti-tumor agent (such as a chemotherapeutic agent), or combinations thereof.

EXAMPLE 27

Generation of DRibbles from Pathogen Infected Cells

This example describes methods that can be used to treat cells ex vivo infected with a pathogen (or a vector encoding a pathogen antigen) to generate DRibbles. Although particular pathogens and cells are described in this example, using this disclosure and other publicly known methods, one skilled in the art can use other combinations of cells and pathogens using routine methods.

Virus

In one example, the kidney cell line 293 (ATCC) is infected with adenovirus, for example in the form of an adenoviral vector. 293T cells will be infected with recombinant adenoviruses at M.O.I. of 10 at 37° C. for 4 hours.

In another example, human T cells are infected with HIV, for example in the form of an HIV vector. Cells (such as $2\times10^5$-$2\times10^6$ cells) are infected multiplicity of infection (MOI) of at least 20, such as at least 50, or at least 100 under conditions sufficient to permit infection of the cells by HIV, such as at 37° C. for at least 24 hours Bacteria In another example, macrophages are infected with bacteria, such as *M. tuberculosis*. *M. tuberculosis* (such as strains H37Rv (ATCC 27294) or Erdman (ATCC 35801)) are adjusted to $10^8$ bacteria/ml by passing the bacterial suspension through a 23-gauge needle 10 times and vortex agitating the suspension briefly. The suspension is allowed to rest for 5 minutes in a 15-ml polystyrene tube and 5 ml of the top is removed and used as the inoculum. The inoculum can be stained by the Ziehl-Neelson technique and observed by light microscopy to confirm that dispersed preparations are used. Viability of the bacteria can be confirmed by the LIVE-DEAD assay (Molecular Probes, Eugene, Oreg.). Monocyte-derived macrophages can be obtained from PBMCs using routine methods. For example, PBMCs isolated from heparinized blood on a Ficoll-Histopaque (Sigma Chemicals, St. Louis, Mo.) gradient are grown in the presence of RPMI 1640 supplemented with 20% autologous serum (for example in a 24-well tissue culture dish). Monocytes mature into macrophages after 3 to 4 days. Macrophage monolayers (such as about $5\times10^5$ cells) are incubated with *M. tuberculosis* (approximately $5\times10^5$-$10^6$ bacteria/monolayer) in RPMI 1640 with 10% autologous serum for at least 1 hour at 37° C. The monolayers can be washed to remove unbound extracellular bacteria.

Fungus

In another example, macrophages are infected with a fungus, such as a *Histoplasma* cell. Approximately $10^2$ to $10^5$ mycelial particles are exposed to $1\times10^5$ cells under conditions sufficient to permit infection of the cells by the fungus, such as at 37° C. for at least 12 hours, such as 24 hours.

Protozoa

In another example, erythrocytes are infected with protozoa, such as *Plasmodium* using routine methods (for example see Trager and Jensen, *Science* 193:673-5, 1976). For example, a culture of 1% parasitemia and 2% erythrocytes are incubated under conditions sufficient to permit infection of the erythrocytes by the protozoa, such as at 37° C.-38° C. at low-oxygen atmosphere (1-5% $O_2$, 3%-7% $CO_2$, balance $N_2$) for 18-24 hours. If desired, protozoa can be synchronized using standard methods known in the art (for example using 5% sorbitol or aphidicolin at 1.5 µg/ml).

Production of DRibbles

Infected cells are then exposed to a proteasome inhibitor. For example, cultured infected cells (such as about 30 million cells) can be treated with ALLM or MG132 (5 µg/ml) or with 20-1000 nM Velcade® for 6-48 hours to block proteasome-mediated degradation of proteins. In addition, tunicamycin (for example at 5 µg/ml) or other agent that decreases protein glycosylation can be co-incubated with the infected cells to enhance DRibble production. In some examples, the cells are then exposed to conditions that induce autophagy, such as incubation in HBSS media or 10-100 nM rapamycin (for example in the presence of 10 mM $NH_4Cl$ to reduce lysosome function) for 12-24 hours.

Following exposure of the cells to a proteasome inhibitor (and in some examples the auotphagy inducer), the cells producing DRibbles are administered to a subject to immunostimulate the subject to the pathogen or antigenic peptide encoded by the vector, for example as described in Example 28.

In some examples, the DRibbles are harvested as follows. Culture supernatant is collected and whole cells and large cell debris removed by a low speed centrifugation (250 g for 10 minutes). The resulting supernatant is further centrifuged at a high speed (10,000 g for 15 minutes) to pellet DRibbles. The pellets (containing the DRibbles) are washed once by re-suspending in PBS (20 ml) and pelleting at high speed as above. The washed pellets are resuspended in 300 µl PBS (10 µl DRibble=1 million cells) and snap frozen in liquid nitrogen and kept at −80° C. in small aliquots until use.

The resulting DRibbles can be administered to a subject to treat an infection or used to stimulated APCs ex vivo and the DRibble-stimulated APCs administered to the subject, for example as described in Example 28.

EXAMPLE 28

Administration of Immunostimulatory Agents to Treat Infection

This example describes methods of simulating an immune response against a pathogen by using the immunostimulatory agents (treated cells, isolated DRibbles, or DRibble-stimulated APCs) described in Example 27. DRibbles can be administered directly into a subject, or can be used to load APCs and the loaded APCs administered to the subject. Such methods can be used prophylacticly to prevent or reduce severity of a pathogen infection in the future, or can be used to treat a subject having a pathogen infection.

In one example, pathogen infected cells (or transduced cells expressing a peptide antigen) producing DRibbles due to incubation with a proteasome inhibitor, autophagy inducer, or both. For example, at least 10 million of such treated cells (such as at least 20 million, or at least 50 million, for example 10-200 million or 20-300 million treated cells) can be administered to a subject alone, or in the presence of a pharmaceutically acceptable carrier or a therapeutic agent, such as an anti-microbial compound (such as an antiviral or antibacterial agent). In another example, treated cells are administered in the presence of an adjuvant or other immunostimulant. Exemplary, non-limiting modes of administration include s.c., i.d., i.v., and i.p.

In one example, DRibbles are administered directly to a subject. For example, 1-1,000 µg (such as 10 µg, 100 µg, or 1 mg) DRibbles can be administered to a subject alone, or in the presence of a pharmaceutically acceptable carrier or a therapeutic agent, such as an anti-microbial compound (such as an antiviral or antibacterial agent). In another example, DRibbles are administered in the presence of an adjuvant or other immunostimulant. Examplary, non-limiting modes of administration include s.c., i.v., i.d, and i.p.

In another example, DRibbles are used to load APCs, which will stimulate naive T cells in vivo when administered to a subject. Although this example describes the use of DC as APCs, one skilled in the art will understand that other APCs can be used. DC can be generated from PBMCs obtained from the subject as described in Example 22. Alternatively, bone marrow derived DC can be prepared as generally described in Example 9 or 10.

DRibble-loaded dendritic cells are prepared as described in Example 22. Briefly, DC cultured at 2-6 million cells per ml of culture media are incubated with 10-100 µl/ml of DRibbles for at least 6 hours.

The resulting DRibble-loaded APCs can be washed prior to administration to the subject. DRibble-loaded APCs can be administered to a subject alone, or in the presence of a pharmaceutically acceptable carrier. In another example, DRibble-loaded APCs are administered in the presence of an adjuvant or other immunostimulant. Examplary, non-limiting modes of administration include s.c., i.v., i.d., and i.p. In one example, 5-50×10⁶ DRibble-loaded APCs are administered, for example in one or more unit doses.

EXAMPLE 29

Treatment of an Infection by Administration of a Proteasome Inhibitor

This example describes methods that can be used to treat an infection in a subject (such as a human or veterinary subject), wherein the method includes administration of a therapeutically effective amount of one or more proteasome inhibitors, autophagy inducers, or both, to the subject thereby producing DRibbles in vivo and treating the subject.

A subject having an infection is administered a proteasome inhibitor, such as Velcade®, in an amount sufficient to stimulate or enhance production of DRibbles by a pathogen-infected cell in the subject. In particular examples, the proteasome inhibitor is administered in an amount that does not significantly cause apoptosis of the infected cells, but instead permits an immune response via T-cells to treat the infection. In a particular example, the subject is administered no more than 1 mg/m²/dose Valcade®, such as no more than 0.1 mg/m²/dose or no more than 0.01 mg/m²/dose Velcade®.

In addition to the proteasome inhibitor, other therapeutic agents can be administered to the subject, for example at a time before, during or after administration of the proteasome inhibitor. For example, tunicamycin or other agent that decreases protein glycosylation can be administered at a sublethal dose in combination with a proteasome inhibitor (or a time soon before or after administration of the proteasome inhibitor), for example to enhance production of DRibbles by infected cells in the subject. In another or additional example, an immunostimulant, such as a cytokine, is administered to the subject, for example to enhance the immune response against the infected cell-derived DRiPs. In a particular example, the adjuvant is administered after the formation of DRibbles in the subject.

In yet another example, one or more agents that induce autophagy are administered to the subject. For example, 20 mg/kg CCI-779 can be administered via i.v. infusion (for example in one or more doses, such as 1-5 doses). In yet another example, combinations of these other therapeutic agents are administered.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. I therefore claim as my invention all that comes within the scope and spirit of these claims.

I claim:

1. Isolated defective ribosomal products (DRiPs) in blebs (DRibbles) produced using an ex vivo method comprising:
    contacting a tumor cell with a proteasome inhibitor under conditions sufficient for the cell to produce DRibbles;
    contacting the tumor cell with an amount of NH₄Cl sufficient to reduce lysosome-mediated protein degradation;
    optionally contacting the tumor cell with an agent that reduces glycosylation, with an autophagy inducing agent, or combinations thereof, under conditions sufficient to enhance production of DRibbles by the tumor cell; and
    harvesting DRibbles secreted by the tumor cell, thereby producing isolated DRibbles, wherein the DRibbles are isolated to at least 50% purity.

2. The isolate DRibbles of claim 1, wherein the conditions sufficient for the cell to produce DRibbles comprises incubation with an effective amount of the proteasome inhibitor that does not substantially induce apoptosis of the tumor cell.

3. The isolated DRibbles of claim 1, wherein the proteasome inhibitor comprises a reversible proteasome inhibitor.

4. The isolated DRibbles of claim 1, wherein the tumor cell is isolated from a subject, and wherein the subject is administered a therapeutically effective amount of a lymphodepletion agent prior to contacting the tumor cells with the proteasome inhibitor.

5. The isolated DRibbles of claim 1 wherein the tumor cell is contacted with an autophagy inducing agent, thereby producing intracellular DRibble autophagy bodies; and the method further comprises
    lysing the tumor cells; and
    collecting the intracellular DRibble autophagy bodies.

6. The isolated DRibbles of claim 1, wherein the tumor cell is a cancer cell.

7. The isolated DRibbles of claim 6, wherein the cancer cell is a breast cancer cell, lung cancer cell, hepatocellular carcinoma cell, renal cell carcinoma cell, or melanoma cell.

8. The isolated DRibbles of claim 6, wherein the cancer cell is a adenocarcinoma cell.

9. The isolated DRibbles of claim 1, wherein harvesting comprises separating DRibbles from the tumor cells, and collecting the DRibbles.

10. The isolated DRibbles of claim 1, wherein the DRibbles include less than 5% of whole cells.

11. The isolated DRibbles of claim 1, wherein the tumor cell is contacted with the autophagy inducing agent under conditions sufficient to substantially increase autophagy in the tumor cell.

12. The isolated DRibbles of claim 1, wherein harvesting DRibbles comprises:
- centrifuging the tumor cells under conditions sufficient to pellet the tumor cells but not the DRibbles;
- collecting a supernatant containing DRibbles;
- centrifuging the supernatant under conditions sufficient to pellet the DRibbles; and
- collecting the pellet containing DRibbles, thereby producing isolated DRibbles.

13. A composition comprising the isolated DRibbles of claim 1 and dimethyl sulfoxide (DMSO).

14. The isolated DRibbles of claim 6, wherein the cancer cell is a breast cancer cell.

15. The isolated DRibbles of claim 6, wherein the cancer cell is a lung cancer cell.

16. A kit, comprising:
- the isolated DRibbles of claim 1; and
- one or more chemotherapeutic or lymphodepletion agents.

17. A kit, comprising:
- the isolated DRibbles of claim 1; and
- an agent that inhibits tumor cells or stromal cells.

18. A composition, comprising:
- the isolated DRibbles of claim 1; and
- an antibody specific for a T-cell costimulatory molecule.

19. The composition of claim 18, wherein the antibody specific for a T-cell costimulatory molecule comprises anti-OX-40.

20. A composition, comprising:
- the isolated DRibbles of claim 1; and
- granulocyte-colony stimulating factor (GM-CSF).

21. The isolated DRibbles of claim 1, wherein the DRibbles are isolated to at least 90% purity.

22. An immunogenic composition comprising the isolated DRibbles of claim 1.

23. The immunogenic composition of claim 22, further comprising an anti-tumor chemotherapeutic agent, an immunostimulant, APCs that have been loaded with the DRibbles, or combinations thereof.

24. The immunogenic composition of claim 22, wherein the immunogenic composition is a vaccine.

25. The immunogenic composition of claim 22, further comprising an immunostimulatory agent.

26. A method of stimulating an immune response against one or more DRiPs in a subject, comprising:
- administering a therapeutically effective amount of the immunogenic composition of claim 22 to a subject, thereby stimulating an immune response against one or more DRiPs in the subject.

27. The method of claim 26, wherein the subject has a tumor.

28. The method of claim 27, wherein the subject is administered a therapeutically effective amount of a lymphodepletion agent prior to administering the immunogenic composition.

29. The method of claim 26, wherein administering the immunogenic composition to the subject comprises administration of at least three doses of the immunogenic composition over a period of at least 180 days.

30. A method of stimulating an immune response against a tumor cell in a subject, comprising:
- incubating the isolated DRibbles of claim 1 with an antigen presenting cell (APC) obtained from peripheral blood mononuclear cells (PBMCs) from the subject under conditions sufficient for the APC to present one or more DRiPs, thereby generating DRibble-loaded APCs; and
- administering a therapeutically effective amount of the DRibble-loaded APCs to the subject, thereby stimulating an immune response against one or more DRiPs.

31. The method of claim 30, wherein the tumor cells are obtained from the subject.

32. The method of claim 30, wherein the APC is a dendritic cell (DC).

33. A method of stimulating an immune response against a tumor cell in a subject, comprising:
- administering a therapeutically effective amount of the isolated DRibbles of claim 1 to the subject, thereby stimulating an immune response against one or more DRiPs.

34. The method of claim 33, further comprising administering an immunostimulant to the subject.

35. The method of claim 34, wherein the immunostimulant is an adjuvant.

36. The method of claim 34, wherein the immunostimulant comprises granulocyte macrophage-colony stimulating factor (GM-CSF).

37. The method of claim 33, wherein the cell is a mammalian tumor cell.

38. The method of claim 37, wherein the mammalian tumor cell is a cancer cell.

39. The method of claim 37, wherein the mammalian tumor cell is a benign tumor cell.

40. The method of claim 33, further comprising administering a therapeutically effective amount of a PD1 antibody or siRNA to the subject.

\* \* \* \* \*